United States Patent
Uchiyama et al.

(10) Patent No.: US 7,158,234 B2
(45) Date of Patent: Jan. 2, 2007

(54) OPTICAL SCANNING OBSERVATION APPARATUS

(75) Inventors: Akio Uchiyama, Saitama (JP); Akihiro Horii, Hachioji (JP); Shuhei Iizuka, Hachioji (JP); Tadashi Hirata, Hachioji (JP); Mitsuhiro Hara, Musashino (JP); Yoshiyuki Kumada, Komae (JP); Kazunari Tokuda, Hachioji (JP)

(73) Assignee: Olympus Corporation, Tokyo (JP)

( * ) Notice: Subject to any disclaimer, the term of this patent is extended or adjusted under 35 U.S.C. 154(b) by 251 days.

(21) Appl. No.: 10/808,857

(22) Filed: Mar. 25, 2004

(65) Prior Publication Data

US 2004/0181148 A1 Sep. 16, 2004

Related U.S. Application Data

(63) Continuation of application No. PCT/JP02/11283, filed on Oct. 30, 2002.

(51) Int. Cl.
*G01B 9/02* (2006.01)
*G01B 11/02* (2006.01)

(52) U.S. Cl. .................. 356/479; 356/511; 356/497

(58) Field of Classification Search .............. 356/479, 356/497, 511
See application file for complete search history.

(56) References Cited

U.S. PATENT DOCUMENTS 5,321,501 A * 6/1994 Swanson et al. ............ 356/479
6,069,698 A 5/2000 Ozawa et al.
6,134,003 A * 10/2000 Tearney et al. ............. 356/479
6,191,862 B1 * 2/2001 Swanson et al. ............ 356/479
6,687,010 B1 * 2/2004 Horii et al. ................. 356/479
2003/0004412 A1 * 1/2003 Izatt et al. .................. 356/450
2005/0168751 A1 * 8/2005 Horii et al. ................. 356/479

FOREIGN PATENT DOCUMENTS

| JP | 6-511312 | 12/1994 |
|---|---|---|
| JP | 7-243965 | 9/1995 |
| JP | 11-72431 | 3/1999 |
| JP | 11-148897 | 6/1999 |
| JP | 2000-126115 | 5/2000 |

* cited by examiner

*Primary Examiner*—Gregory J. Toatley, Jr.
*Assistant Examiner*—Patrick Connolly
(74) *Attorney, Agent, or Firm*—Scully, Scott, Murphy & Presser, P.C.

(57) ABSTRACT

Before performing observation with an optical scanning probe using a low-coherence light source and the like, a shutter is inserted in a reference light side optical path to create a state wherein interference light does not occur, in which state a reference member is set to a focal position of a converging optical system such that the output of a light detector is maximal by moving the reference member by a driving device at an observation light optical path side of an optical scanning probe, following which the shutter is opened, and the position of a mirror at the reference light side is moved and set such that the output of the light detecting means is maximal, thereby enabling the optical scanning observation apparatus to be set to a state of suitable optical properties, easily and smoothly.

23 Claims, 55 Drawing Sheets

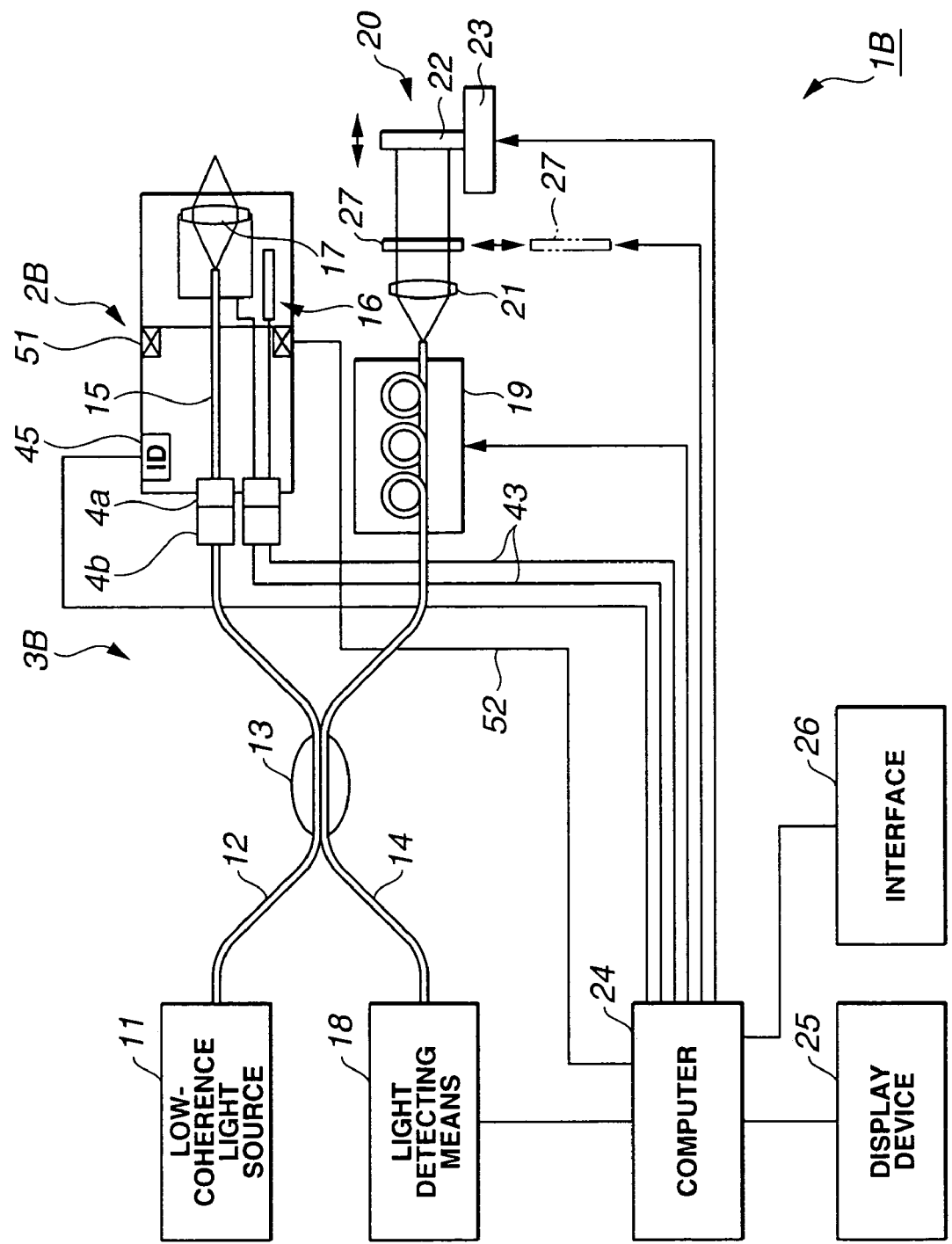

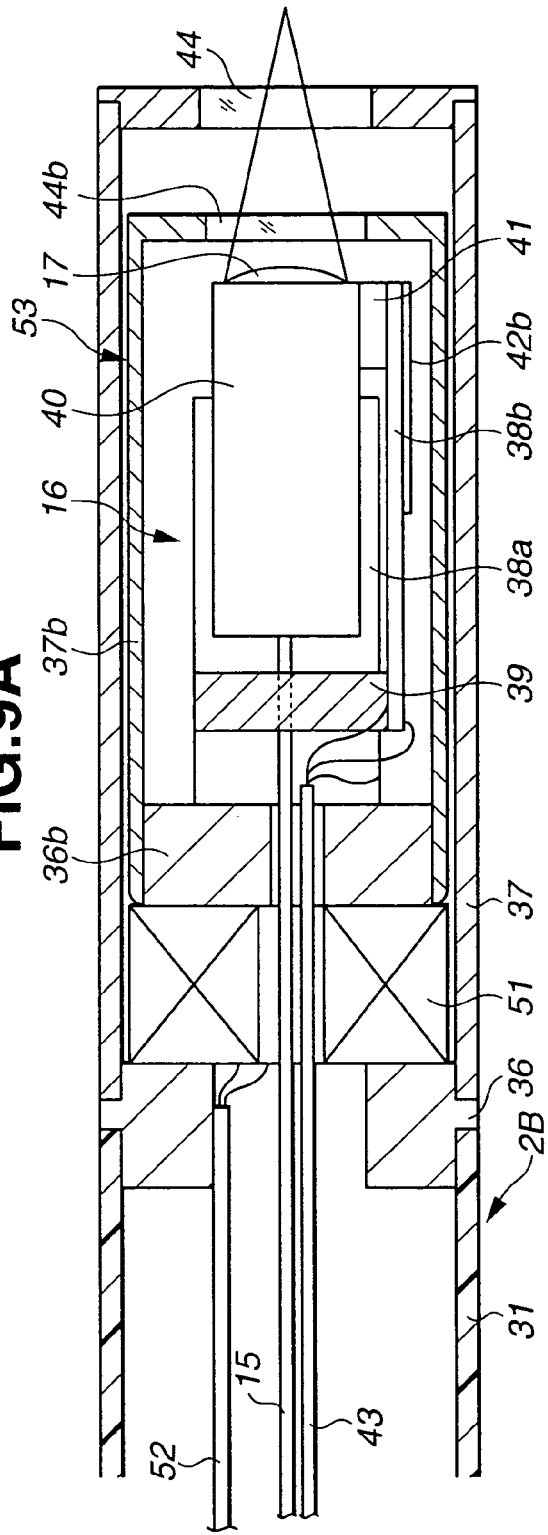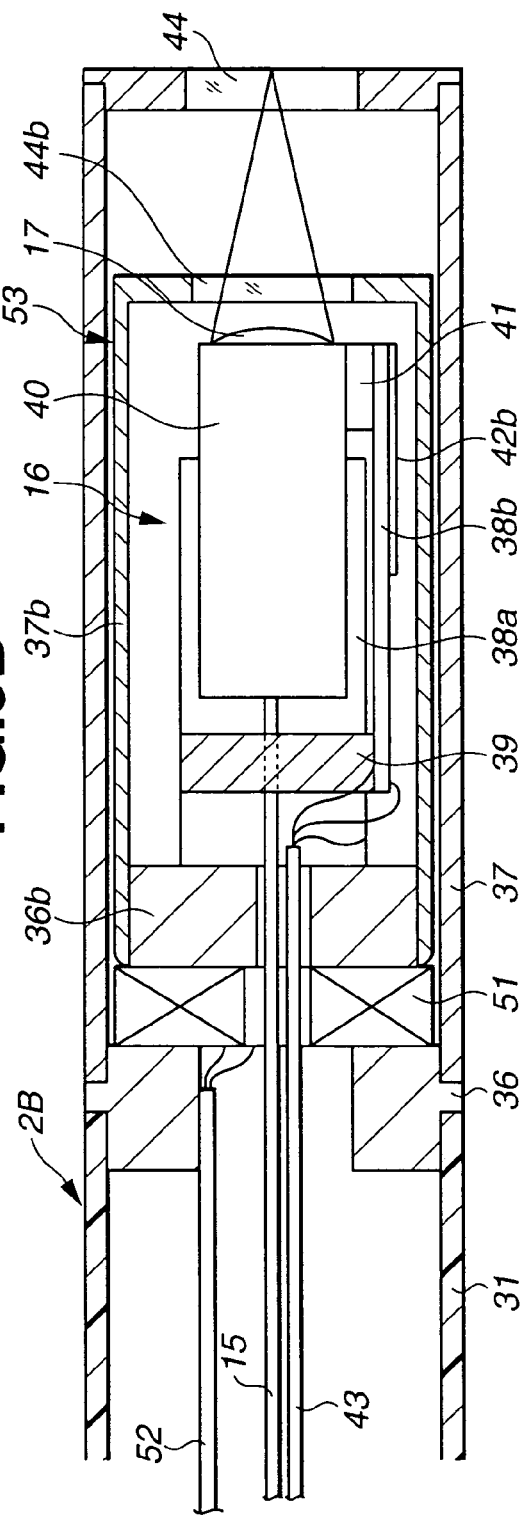

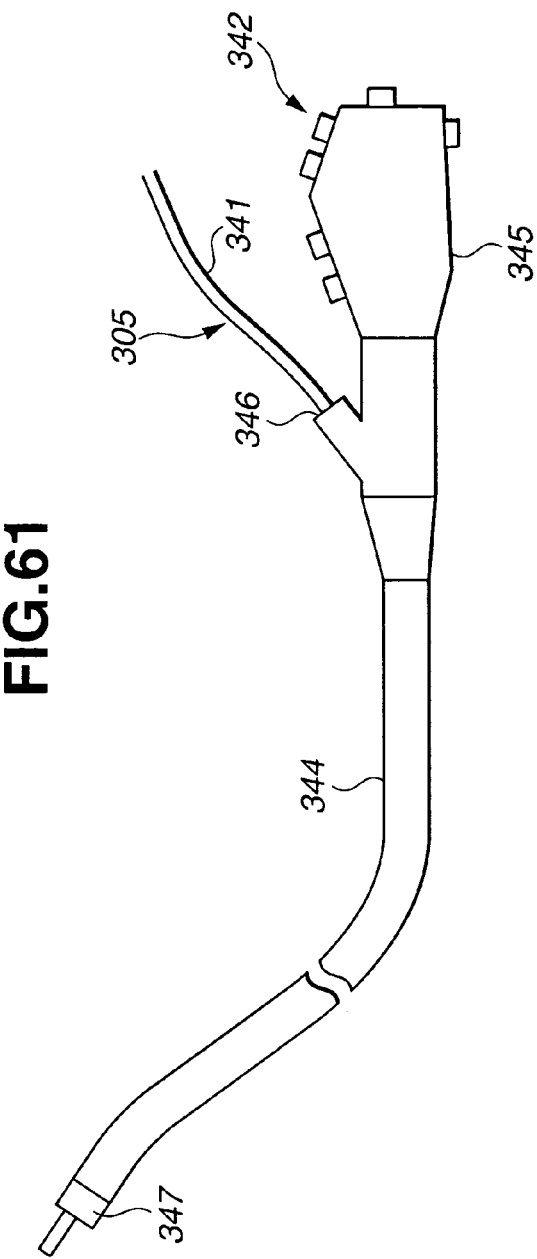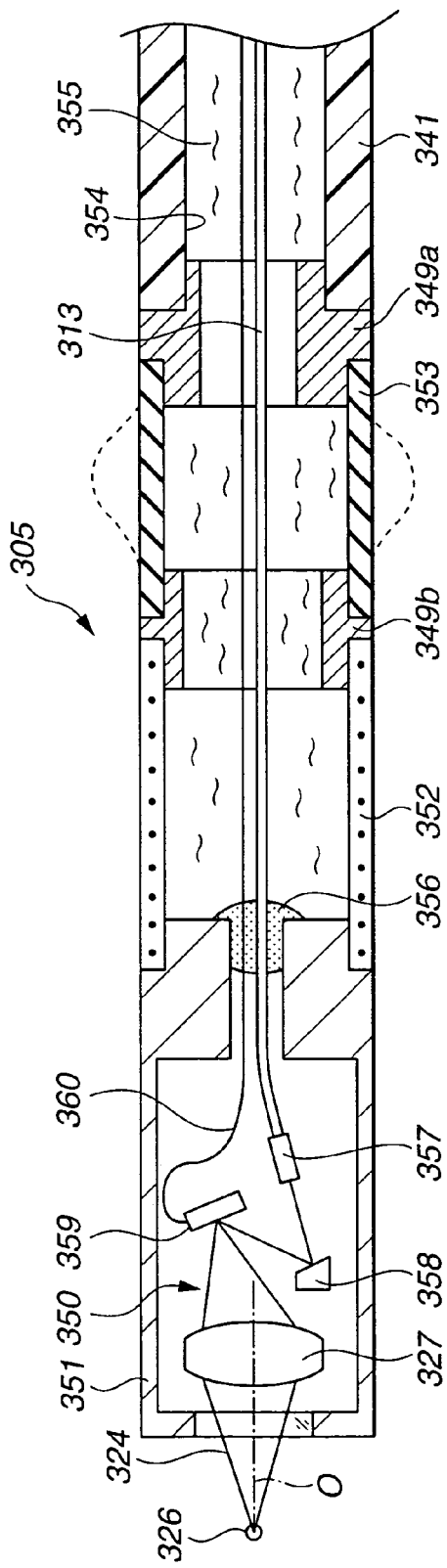

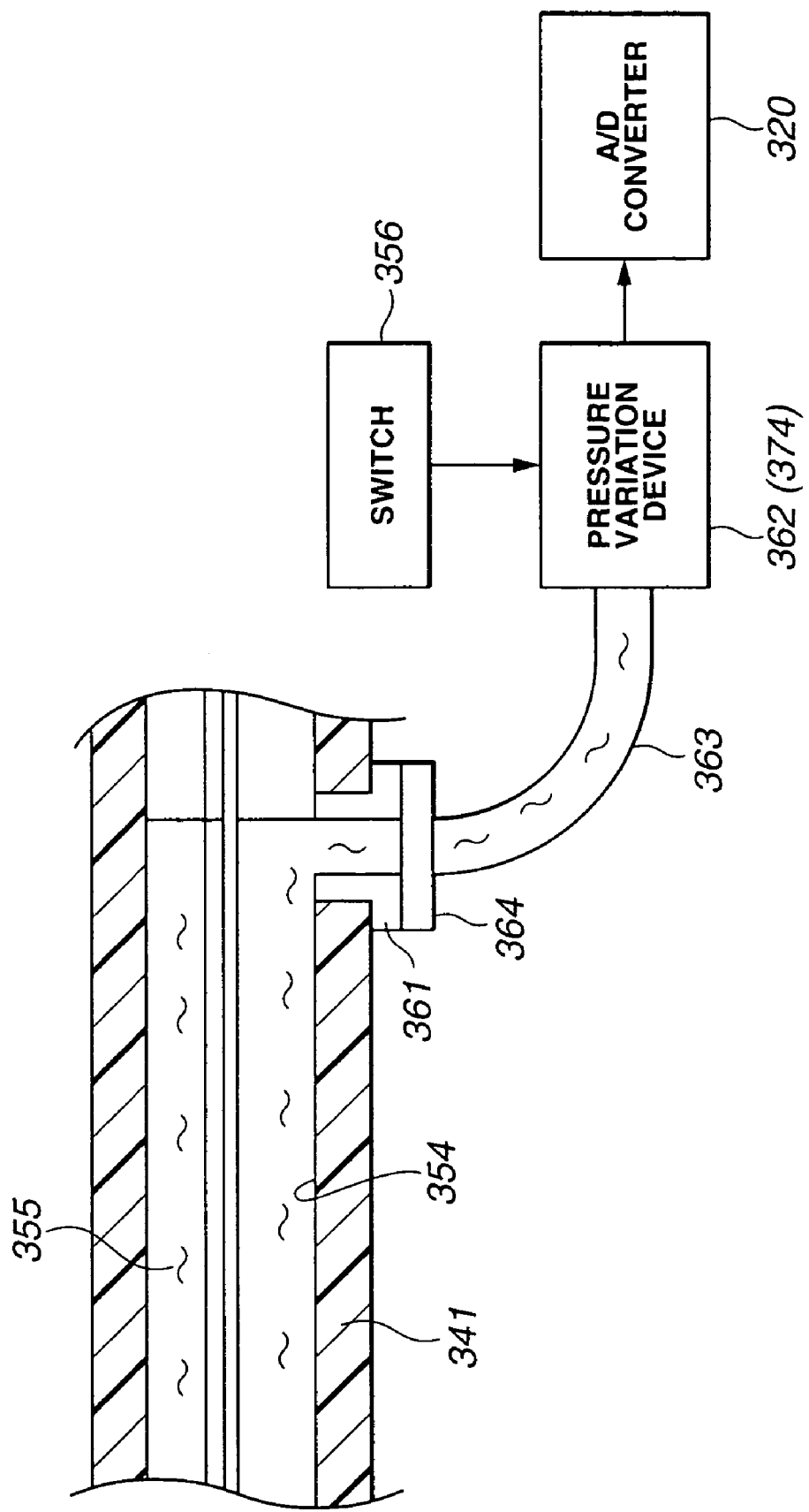

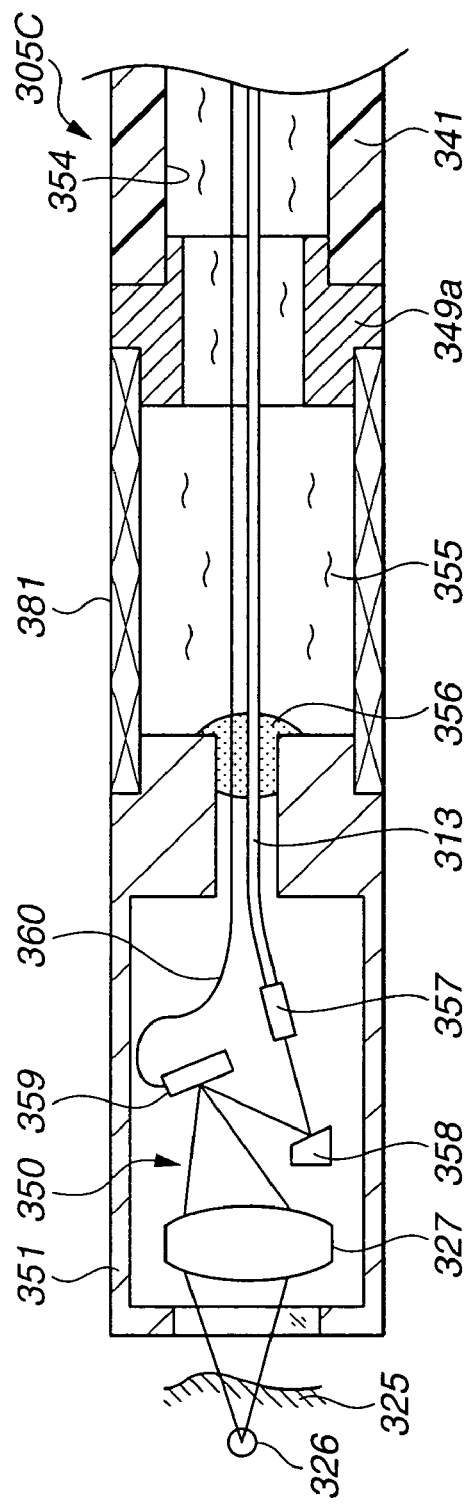
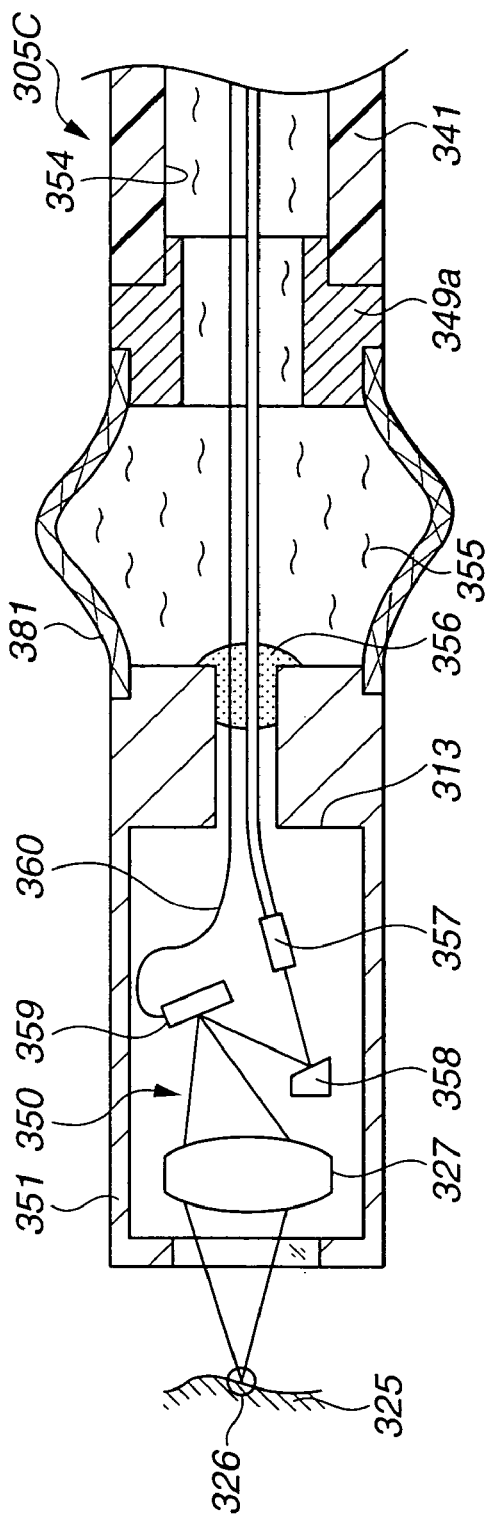

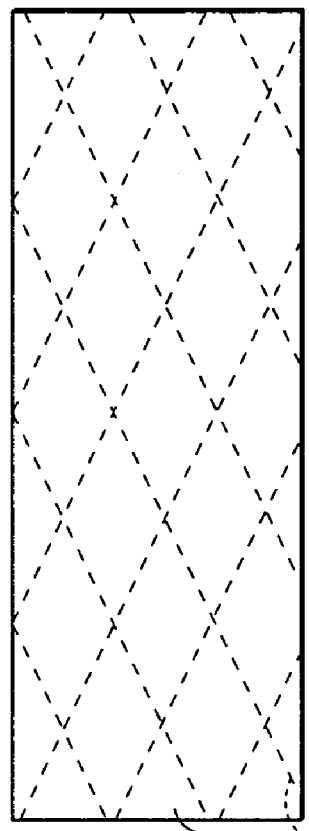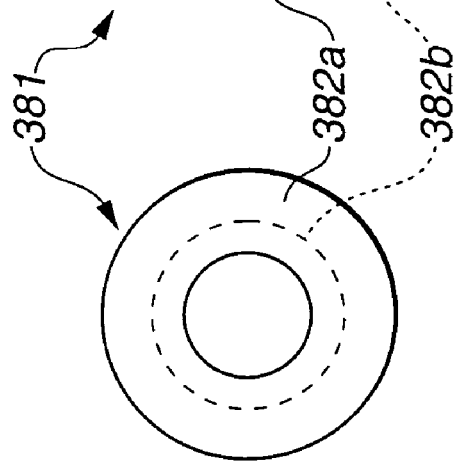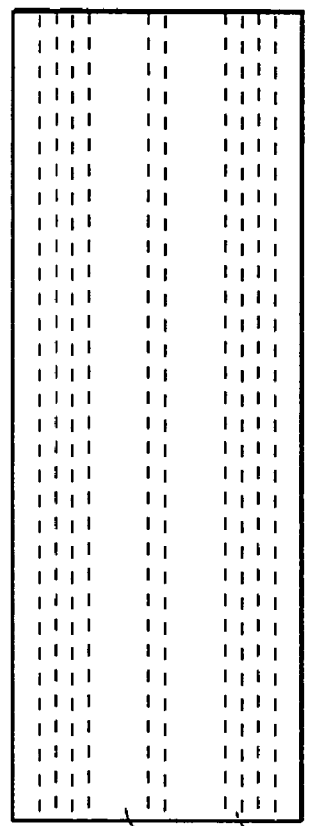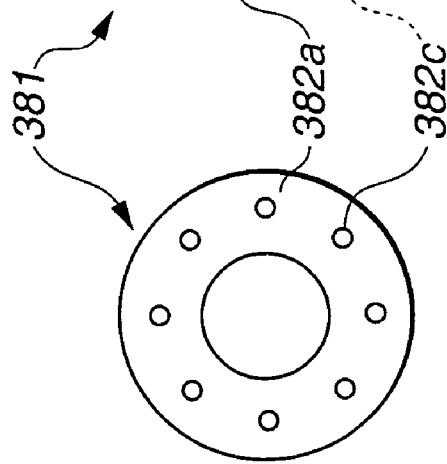

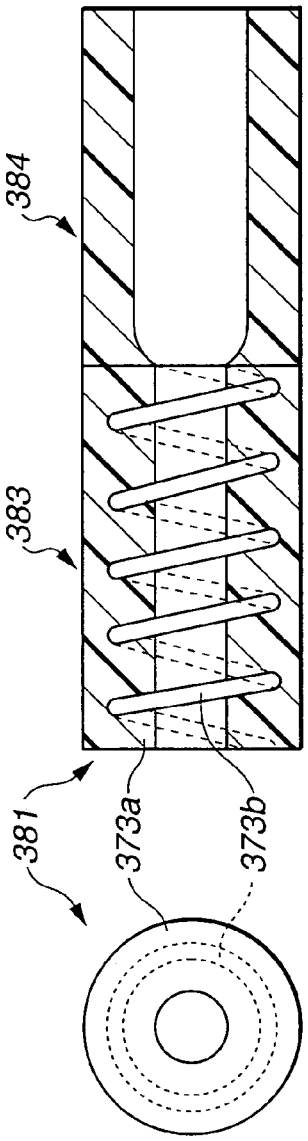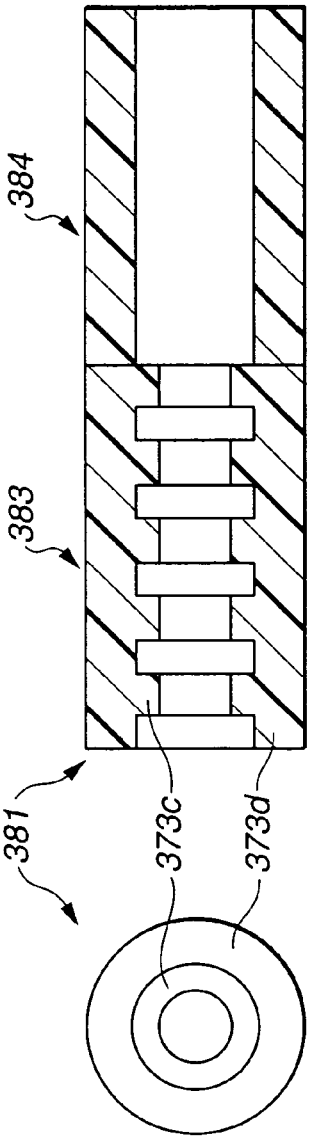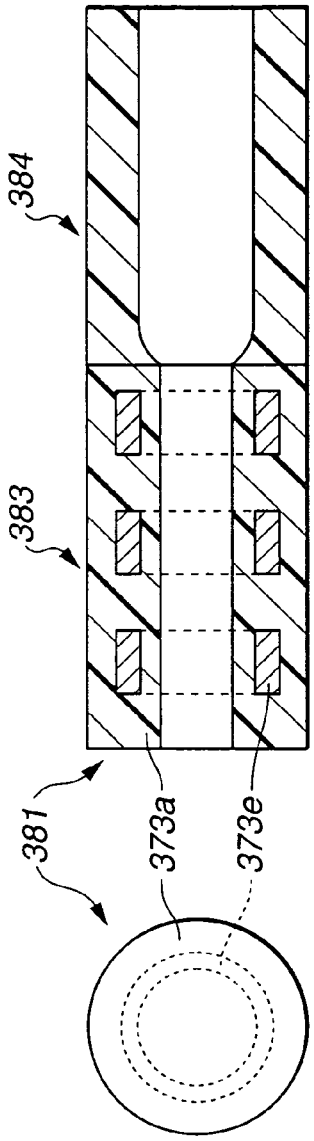

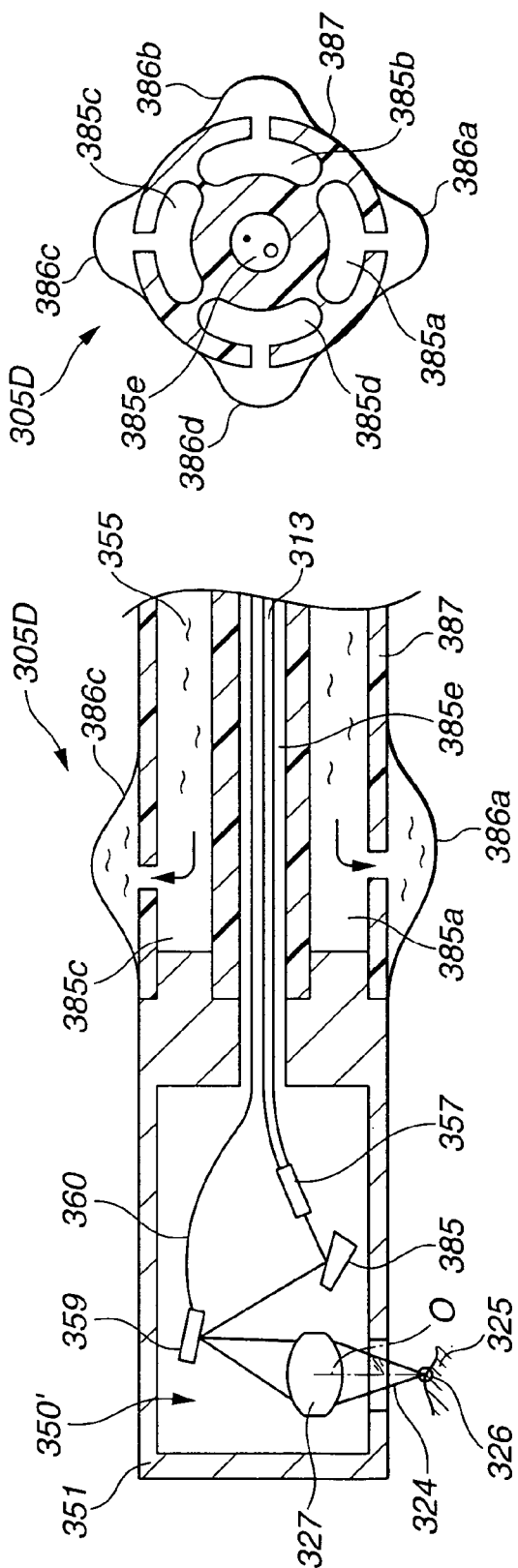

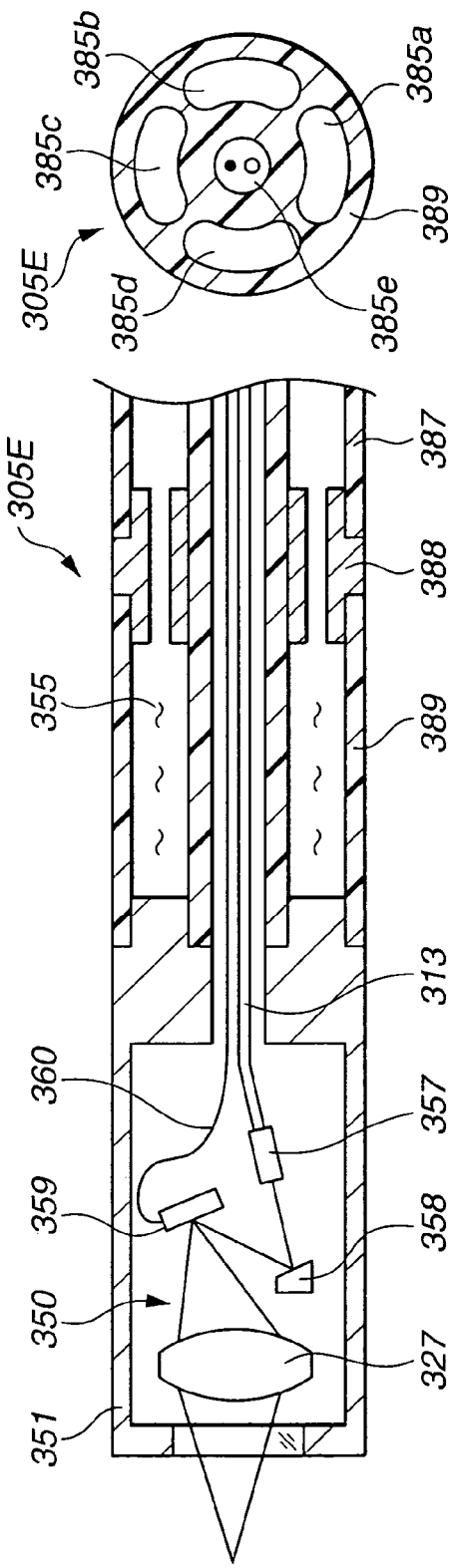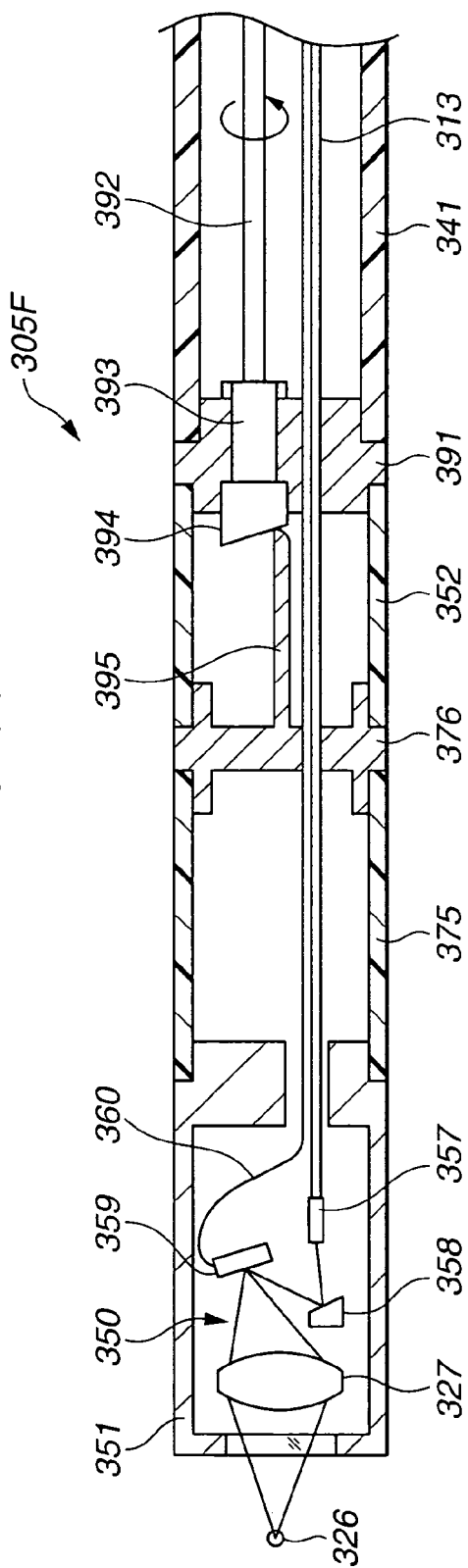

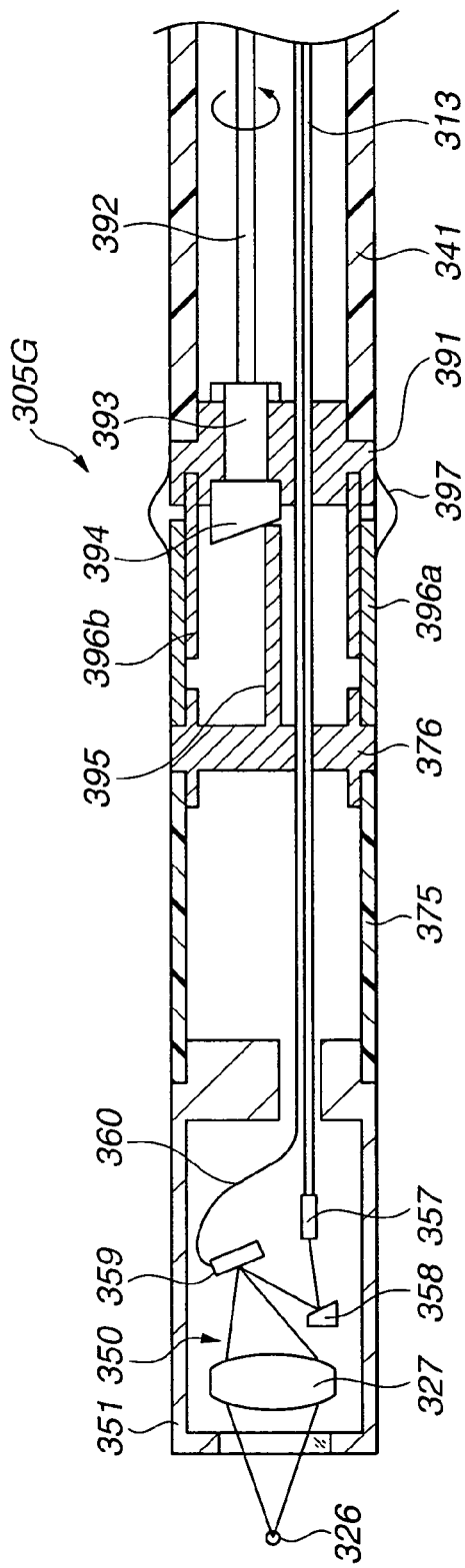

OPTICAL SCANNING OBSERVATION APPARATUS

CROSS REFERENCE TO RELATED APPLICATION

This application is a continuation application of PCT/JP02/11283 filed on Oct. 30, 2002 the disclosure of which is incorporated herein by its reference.

TECHNICAL FIELD

The present invention relates to an optical scanning observation apparatus which creates a tomographic image of a subject based on information of scattered light from the subject, using interference of low-coherence light and so forth.

BACKGROUND ART

In recent years, an interference-type optical scanning observation apparatus which can create a tomographic image of a subject using low-coherence light for diagnosis of body tissue has been proposed, for example in Japanese Unexamined Patent Application Publication No. 11-148897. With this conventional example, a detachable optical scanning probe is used to obtain a tomographic image of body tissue.

In the event of mounting a detachable optical scanning probe on an apparatus at a low-coherence light source side, the interference system must be adjusted since an image with an offset focal point will be obtained otherwise, so optical capabilities must be set in a suitable state such as allowing detection of interference light at the focal position, and so forth.

Also, in recent years, an optical tomographic imaging apparatus capable of obtaining optical information within the tissue for diagnosing body tissue has been proposed, besides an imaging apparatus for obtaining optical information of the surface state of the tissue.

Japanese Unexamined Patent Application Publication No. 2000-126115 discloses an optical scanning probe apparatus. A probe which has optical scanning means at the tip of the probe, and is capable of variation in the focal position in the depth-wise direction, so as to obtain an observation image along the depth-wise direction, is disclosed in this Japanese Unexamined Patent Application Publication No. 2000-126115.

Also, PCT Japanese Translation Patent Publication No. 6-511312 (corresponding to U.S. Pat. No. 5,321,501) discloses a technique for Optical Coherence Tomography (OCT) whereby a tomography image in the depth-wise direction of the body can be obtained using low-coherence interferometry.

Further, Japanese Unexamined Patent Application Publication No. 11-72431 (corresponding to U.S. Pat. No. 6,069,698) discloses an optical tomographic imaging apparatus capable of obtaining high-resolution optical tomographic images by combining the optical probe disclosed in Japanese Unexamined Patent Application Publication No. 2000-126115 with low-coherence interferometry.

However, with the preceding example, techniques for setting the optical capabilities to a suitable state are not disclosed.

Also, even in the event that the optical scanning probe is not detachable, an arrangement wherein optical capabilities can be set to a suitable state is desirable, for cases wherein the optical path length and the like of the light transmitting system changes due to change in temperature, and so forth.

Also, setting to a suitable optical property state for cases wherein the focal depth of the optical system for converging at the tip side of the scanning probe is shallow is also desired.

However, the probe disclosed in Japanese Unexamined Patent Application Publication No. 2000-126115 includes a focal point variation mechanism using a piezoelectric device in order to change the position of the focal point in the depth-wise direction, but the size of the focal point variation mechanism is large. Accordingly, the length of the hard portion at the tip of the probe becomes long, creating the problem that scanning and positioning within the body become difficult.

Also, FIG. 15 in Japanese Unexamined Patent Application Publication No. 2000-126115 discloses a method for varying the focal point using push-pull rods. However, this method cannot be realized with flexible and long probes which can be inserted through or built into endoscopes.

Further, Japanese Unexamined Patent Application Publication No. 2000-126115 discloses an embodiment for advancing and retreating a contacting member with the subject, as a focal position variation mechanism. However, this embodiment requires force of an amount for moving the subject or the probe itself, so the size of the actuator becomes great, producing the problem that the apparatus cannot be readily reduced in size. Also, force is applied to the subject itself, which is soft in nature, so there is the problem that fine positional control is difficult.

Moreover, an embodiment is also disclosed wherein only the converging means are advanced and retreated, but in the event of combining and using with low-coherence interference, there is the problem that the detection position from low-coherence interference and the converging position are offset, markedly deteriorating the detecting efficiency.

Also, Japanese Unexamined Patent Application Publication No. 2000-126115 discloses arrangements for advancing and retreating a contacting member with the subject, or advancing and retreating the converging means, as focal point moving variation mechanisms, but this requires moving objects with large load or mass, so changing the focal position quickly has been difficult.

Japanese Unexamined Patent Application Publication No. 11-72431 discloses an apparatus combining low-coherence light interference and a high-resolution optical system using a micro-optical scanner. This also discloses a configuration for oscillating a scan head having a micro-optical scanner, so as to scan the converging position in the depth-wise direction. However, there is the problem in combining with low-coherence interference in that the detection position from low-coherence interference and the converging position are offset, markedly deteriorating the detecting efficiency.

Accordingly, the present invention has been made in light of the above-described points, and it is an object thereof to provide an optical scanning observation apparatus and a setting method thereof capable of readily setting to a state wherein optical capabilities are suitable.

Also, it is an object of the present invention to provide an optical scanning observation apparatus wherein the tip hard portion is short, and has a focal point variation mechanism capable of precise control.

Further, it is an object of the present invention to provide an optical scanning observation apparatus capable of quick focal position variation.

Moreover, it is an object of the present invention to provide an optical scanning observation apparatus wherein the detection position from low-coherence interference accords with the converging position even if the focal position is varied, in combination with low-coherence interference.

DISCLOSURE OF INVENTION

The optical scanning observation apparatus according to the present invention comprises: a low-coherence light source; light separating means for separating light emitted from the low-coherence light source into an observation light optical path and a reference light optical path; optical path length variation means provided on at least one of the observation light optical path and reference light optical path; converging means provided on the other end side of the observation light optical path as to the light separating means; a light-receiving optical system for photo-reception of light, emitted from the converging means and irradiated on an object of measurement, which has been reflected or scattered; an observation light return optical path for transmitting light received by the light-receiving optical system; light joining means for joining observation light return optical path and the reference light optical path; and light detecting means for converting light from light joining means into electric signals; image-forming means for generating an image of the object to be observed from the signals detected by the light detecting means; display means for displaying an image; light transmission state changing means provided on the reference light optical path and having optical scanning means for scanning light on the object to be measured, for changing the interference state at the light joining means; a reference member capable of changing the distance as to the converging means at a position where irradiation of light is received from the converging means; focus position detecting means for determining a position as to the reference member and the converging means, based on signals detected by the light detecting means, in a state wherein the light transmission state changing means are operated and the transmission efficiency of the reference light optical path is reduced; and optical path length adjusting means for operating the optical path length variation means based on signals detected by the light detecting means, in a state wherein the light transmission state changing means are operated and interference occurs at the light joining means, such that the optical length of the optical path from the light separating means and passing through the observation light optical path, the converging means, the reference member position determined by the focus position detecting means, the light-receiving optical system, the observation light return optical path, and the light joining means, and that of the reference optical path, generally accord.

Accordingly, first, the reference member is set to the focal position of the converging means by the focal position detecting means in a state of reduced transmission efficiency of the reference light optical path, and further in this state, the state is set wherein interference light is detected and the optical path length is set such that the reference light side optical path and the converging means side optical path accord, thereby enabling the optical properties to be easily and smoothly set to a suitable state, and an optical scanning observation image with good image quality in the subsequent observation mode can be obtained.

With a method for setting a scanning observation apparatus according to the present invention comprising: a low-coherence light source; light separating means for separating light emitted from the low-coherence light source into an observation light optical path and a reference light optical path; optical path length variation means provided on at least one of the observation light optical path and reference light optical path; converging means provided on the other end side of the observation light optical path as to the light separating means; a light-receiving optical system for photo-reception of light, emitted from the converging means and irradiated on an object of measurement, which has been reflected or scattered; an observation light return optical path for transmitting light received by the light-receiving optical system; light joining means for joining observation light return optical path and the reference light optical path; light detecting means for converting light from the light joining means into electric signals; image-forming means for generating an image of the object to be observed from the signals detected by the light detecting means; display means for displaying an image; and optical scanning means for scanning light on the object to be measured; the method comprises: a first step for reducing the transmission efficiency of the reference light optical path; a second step for making reference to the output of the light detecting means with regard to the reference member, and positioning the reference member near the focal position of the converging means; a third step for restoring the transmission efficiency of the reference light optical path; and a fourth step wherein, with the optical length of the optical path from the light separating means and passing through the observation light optical path, the converging means, the reference member position determined by the focus position detecting means, the light-receiving optical system, the observation light return optical path, and the light joining means, as optical path A in a state wherein positioning of the reference member is determined in the second step, signals detected by the light detecting means are referred to, the optical path variation means are operated, and the optical length of the optical path A and the reference light optical path are generally accorded.

BRIEF DESCRIPTION OF THE DRAWINGS

FIG. 8 is a diagram illustrating the overall configuration of the optical scanning observation apparatus according to a second embodiment of the present invention;

FIG. 9A and FIG. 9B are cross-sectional diagrams showing the configuration of the tip side of an optical scanning probe with regard to a case wherein a piezoelectric device is not driven and a case wherein one is driven;

FIG. 61 is a diagram illustrating an optical scanning probe inserted through a channel of an endoscope;

FIG. 64 is a diagram illustrating the configuration at the tip side of the optical scanning probe;

FIG. 65 is a diagram illustrating the configuration around fluid supplying means (pressurized air supplying means) at the rear end side of the sheath;

FIG. 71A and FIG. 71B are diagrams illustrating cases wherein the tip side of the optical scanning probe according to a fourteenth embodiment of the present invention is not pressurized, and is pressurized, respectively;

FIG. 72A and FIG. 72B are diagram illustrating the configuration of the elastic member;

FIG. 73A and FIG. 73B are diagrams illustrating the structure of the elastic member according to a modification;

FIG. 74A and FIG. 74B are diagrams illustrating an integrated configuration of a moving portion and a fixed portion;

FIG. 75A and FIG. 75B are diagrams illustrating an integrated configuration of a moving portion and a fixed portion;

FIG. 76A and FIG. 76B are diagrams illustrating an integrated configuration of a moving portion and a fixed portion;

FIG. 77A and FIG. 77B are diagrams illustrating the configuration of the tip side of the optical scanning probe according to a fifteenth embodiment;

FIG. 78A through FIG. 78D are diagrams illustrating usage examples inserted through the channel;

FIG. 79A and FIG. 79B are diagrams illustrating the configuration of the tip side of the optical scanning probe according to a sixteenth embodiment;

FIG. 80 is a cross-sectional diagram illustrating the configuration of the tip side of the optical scanning probe according to a seventeenth embodiment;

FIG. 81 is a diagram illustrating the configuration of the tip side of the optical scanning probe according to a first modification;

FIG. 82 is a diagram illustrating the configuration of the tip side of the optical scanning probe using fixing means according to the modification;

BEST MODE FOR CARRYING OUT THE INVENTION

The following is a description of embodiments of the present invention with reference to the drawings.

First Embodiment

A first embodiment of the present invention will be described with reference to FIG. 1 through FIG. 7.

Figure 1:
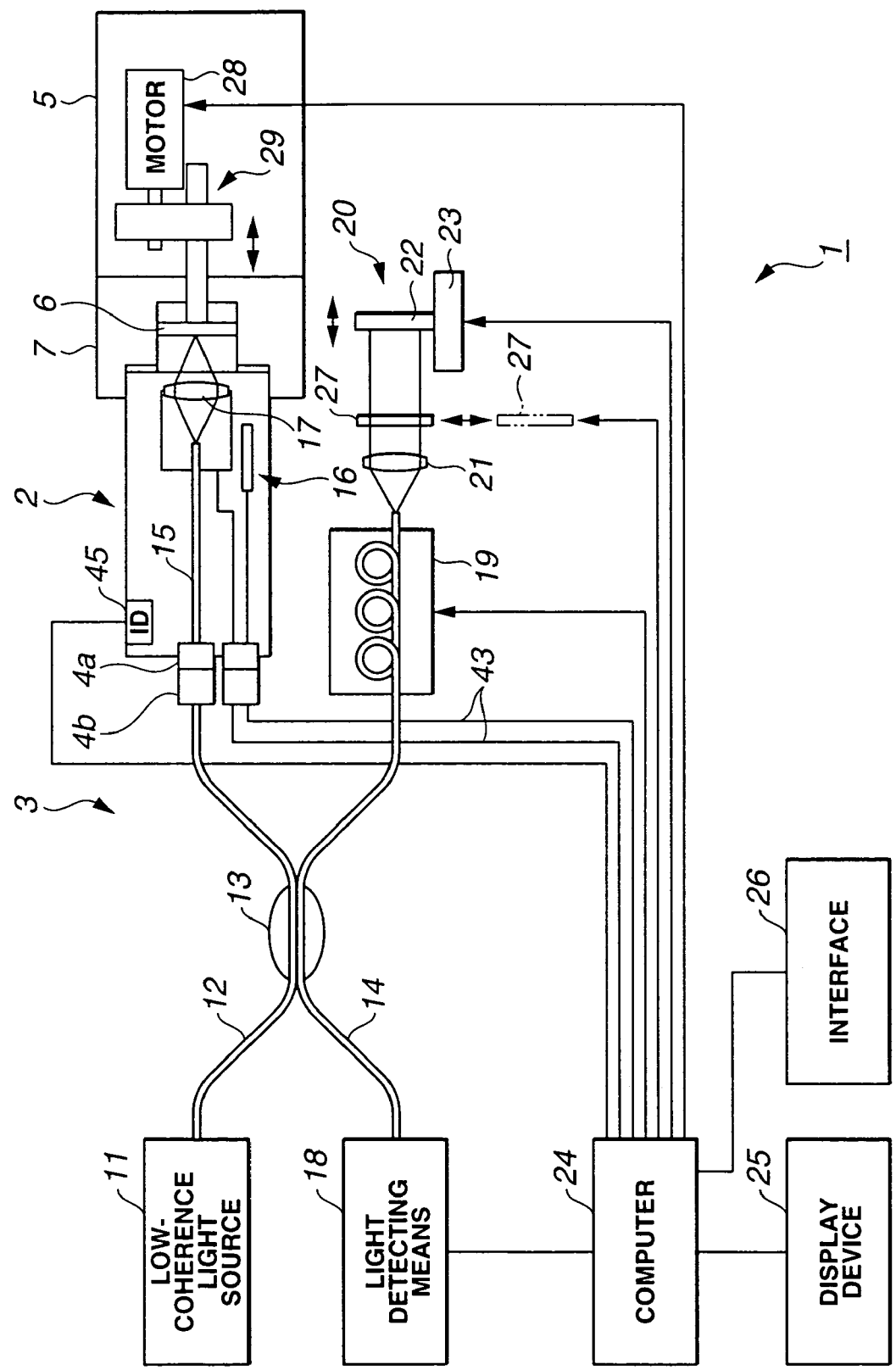
FIG. 1 is a diagram illustrating the overall configuration of the optical scanning observation apparatus according to a first embodiment of the present invention.

As shown in FIG. 1, an optical scanning observation device 1 according to the first embodiment of the present invention comprises an optical scanning probe 2 with optical scanning means built in, for converging and irradiating low-coherence light onto body tissue, and to receive the reflected light therefrom, and an optical scanning observation apparatus main unit (abbreviated as observation apparatus) 3 with an optical connector 4a of the rear end of the optical scanning probe 2 detachably connected for supplying low-coherence light to the optical scanning probe 2 and receiving and imaging return light from the optical scanning probe 2.

Also, with the present embodiment, an optical path length adjusting jig 7 with a reference member 6 capable of being driven (moved) by a driving device 5 is detachably mounted to the front end of the optical scanning probe 2.

A low-coherence light source 11 such as a super high-luminance light-emitting diode (hereafter, abbreviated as SLD) or the like is provided within the observation apparatus 3. The low-coherence light source 11 has a wavelength of 1300 nm for example, and has characteristics of low-coherence light wherein interference occurs only within a short distance range such as 17 μm for the coherence distance, for example. That is to say, following dividing this light into two and then joined again, for example, the light has properties so as to be detected as light where interference has occurred in the event that the difference between the length of the two optical paths from the divided point to the joined point is within a short distance range of around 17 μm, and in the event that the difference in the optical path length is greater, there is no interference exhibited.

The light from the low-coherence light source 11 is cast into one end of a (first) single mode fiber 12, and is carried to the other end (tip face) side.

The single mode fiber 12 is optically joined to a (second) single mode fiber 14 at an optical coupler unit 13 partway along. Accordingly, functions of splitting (dividing) into two at the optical coupler unit 13 and transporting are performed, and the divided light is joined at the coupler unit 13.

An optical connector receptacle 4b is provided on the tip side of the single mode fiber 12 (from the optical coupler unit 13), with an optical connector unit 4a of the optical scanning probe 2 detachably connected, and the light from the low-coherence light source 11 is transmitted (introduced) to a single mode fiber 15 inserted through this optical scanning probe 2.

Then, the transmitted light is converged and irradiated by secondary scanning at the subject (body tissue) side through a converging optical system 17 (configuring converging means) provided at a scanner unit 16 at the tip portion of the optical scanning probe 2.

Also, a part of the reflected light scattered on the surface or within the body tissue side is taken in, which returns to the single mode fiber 12 side through a reverse optical path, of which a part shifts to the single mode fiber 14 side by the optical coupler unit 13, and received by light detecting means 18 from one end of the single mode fiber 14, and then subjected to photo-electric conversion.

Also, an optical path length variation mechanism 20 for changing the optical path length for standard light (reference light) via a polarization adjuster 19 is provided further toward the tip of the single mode fiber 14 from the optical coupler unit 13. This optical path length variation mechanism 20 adjusts and sets so that the optical path length accords the light reflected at the focal position of the converging optical system 17 by the optical scanning probe 2, so as to vary the optical path length of the reference light by detecting interference with light at that portion.

The optical path length variation mechanism 20 comprises a collimator lens 21 at the tip of the single mode fiber 14, removed by the focal distance thereof and facing therewith, a mirror 22 (serving as a coherence gate) disposed facing the light formed onto a parallel light flux by the collimator lens 21, and a moving device 23 such as a moving stage or the like for moving and setting the mirror 22 in the optical axis direction.

The light detecting means 18 are connected to a computer 24 having functions for forming images, and the image signals imaged at the computer 24 are sent to a display device 25, and displayed as an image.

Also, an interface 26 is connected to the computer 24, enabling input of instructions or the like to the computer 24 from a keyboard or the like.

This computer 24 performs driving control of the scanner 16 of the optical probe 2, adjustment control of the polarization direction of the polarization adjuster 19, and control of (the moving device 23 of) the optical path length variation mechanism 20.

Also, with the present embodiment, in the event of connecting the optical scanning probe 2 to the observation apparatus main unit 3 and setting to an observation mode for obtaining optical scanning images, in a setting mode before this, setting is performed beforehand by a later-described adjustment mechanism, to a state of suitable optical properties, that is to say, adjusting and setting by the adjustment mechanism such that the reflected light at the focal position of the converging optical system 17 of the optical scanning probe 2 can be detected as interference light.

Accordingly, a shutter 27 is insertably provided to the optical path length variation mechanism 20. The shutter 27 is inserted into the optical path as shown by solid lines at the time of starting usage, and is retracted outside of the optical path (under control of the computer 24) as shown by two-dot broken lines following adjustment.

In the state that the shutter 27 is inserted into the optical path, the light irradiated from the tip of the single mode fiber 14 is shielded by the shutter 27, and is not irradiated into the tip of the single mode fiber 14. Note that in FIG. 1 (as well as with FIG. 8 and so forth), a comprehensible illustration is made with the shutter 27 inserted into the optical path and removed therefrom, but in reality, the same functions as inserting to and removing from the optical path can be obtained by opening and shutting the shutter 27.

Also, an optical path length adjusting jig 7 is attached to the tip of the optical scanning probe 2 so as to fit to the tip thereof, and a reference member 6 movable in the optical axis direction is disposed on the inner side of the an optical path length adjusting jig 7 facing the converging optical system 17.

The reference member 6 is moved in the optical axis direction of the converging optical system 17 by a feeding screw mechanism 29 using a motor 28. The rotational driving of the motor 28 is controlled by the computer 24.

As described later (as shown in FIG. 1), the shutter 27 is positioned within the optical path, the optical path length adjusting jig 7 is mounted on the optical scanning probe 2, the motor 28 is rotated, and the reference member 6 is set such that the intensity of the light detected by the light detecting means 18 in this case is the greatest. Also, the shutter 27 is retracted from the optical path in this state, and the position of the mirror 22 serving as a coherence gate is adjusted (set) by the moving device 23 so that the interference light is the greatest (maximal).

Figure 2:
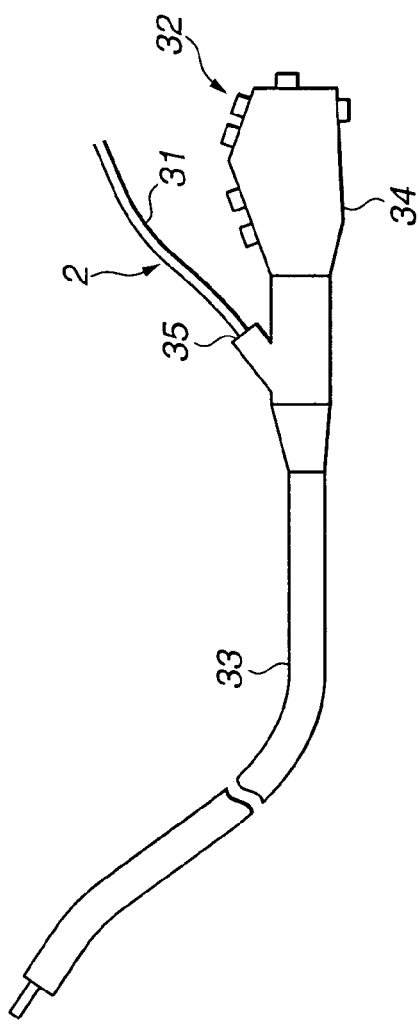
FIG. 2 is a diagram illustrating an endoscope through which an optical scanning probe is inserted.

As shown in FIG. 2, the optical scanning probe 2 is covered with a slender and flexible sheath 31, and can be inserted in a channel of an endoscope 32. The endoscope 32 has a slender insertion portion 33, and an operating unit 34 provided on the rear end of the insertion portion 33, with a treatment instrument insertion opening 35 which communicates with the channel provided on the insertion portion 33 provided near the front end of the operating unit 34, from which the optical scanning probe 2 can be inserted.

In the event that the user desires to inspect whether or not a diseased tissue, under observation with the endoscope 32, the tip side of the optical scanning probe 2 can be protruded from the channel tip, and set near the surface of the tissue which is the object of checking, thereby obtaining an image with the optical scanning probe 2.

Figure 3:
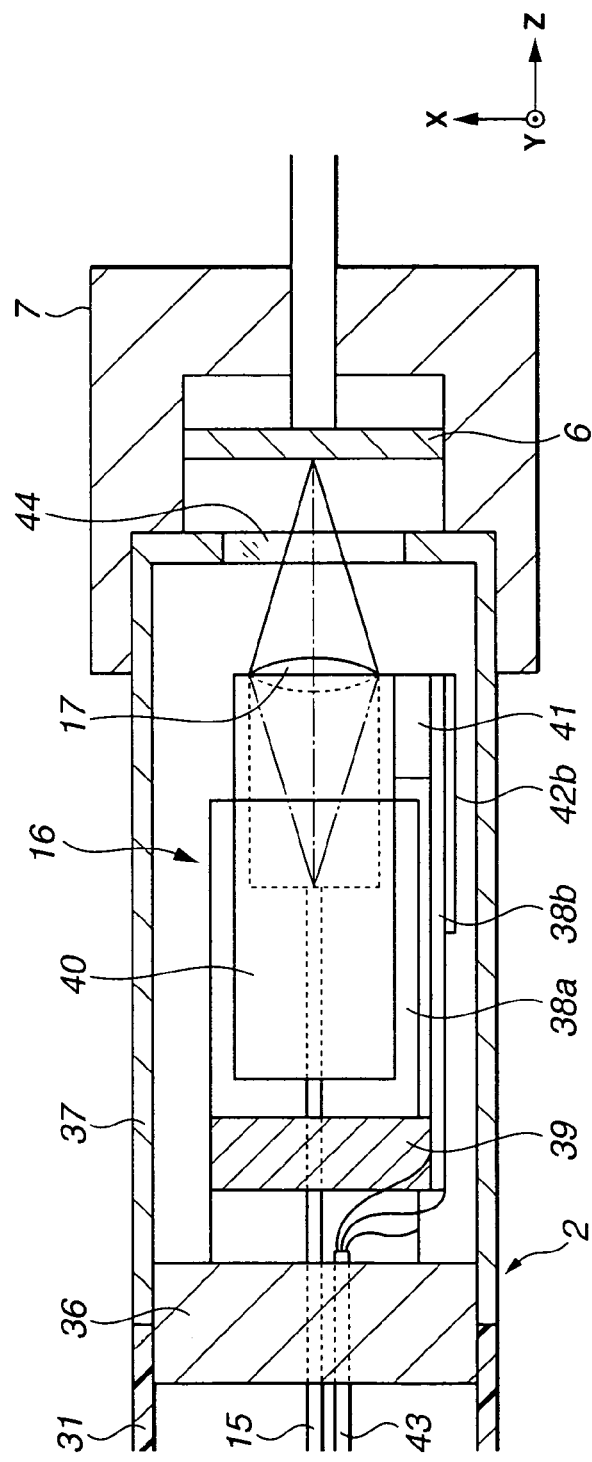
FIG. 3 is a cross-sectional diagram illustrating the configuration of the tip side of the optical scanning probe.

The single mode fiber 15 is inserted through the inner side of the sheath 31, the tip side configuration thereof shown in FIG. 3. Note that FIG. 3 illustrates the state wherein the optical path length adjusting jig 7 is attached.

The tip of the sheath 31 is connected to a cylindrical and hard top cover 37 by a hard base member 36.

Also, the base member 36 has attached thereto a deformable first thin plate 38a which makes up the scanner 16, with the rear end of a deformable second thin plate 38b intersecting the first thin plate 38a partway along the first thin plate 38a by a relay member 39.

A holder 40 to which the converging optical system 17 is attached is held to the tip of the second thin plate 38b by a connecting member 41.

Also, a plate-shaped first piezoelectric device (the rear side on the drawing in FIG. 2) is attached to the plate face of the first thin plate 38a, and a second plate-shaped piezoelectric device 42*b* is attached to the plate face of the second thin plate 38*b*. Then, (electrodes attached to the respective plate faces of) the first piezoelectric device and the second piezoelectric device 42*b* are connected to the computer 24 by a driving cable 43, allowing the first piezoelectric device and the second piezoelectric device 42*b* to be driven in a direction orthogonal to the converging optical system 17 by applying AC driving signals.

In FIG. 3, in the event of driving the second piezoelectric device 42*b* for example, the converging optical system 17 is driven in the vertical direction (the X direction on the coordinates system shown in FIG. 3) along with the holder 40. Also, in the event of driving the first piezoelectric device, the relay member 39 is driven in a direction perpendicular to the drawing in FIG. 3, and the converging optical system 17 is also driven in a direction perpendicular to the drawing (The Y direction on the coordinates system shown in FIG. 3).

That is to say, the light emitted from the converging optical system 17 can be two-dimensionally scanned on the XY plane. Note that the configuration of this scanner 16 is not restricted to that shown in FIG. 3, for example, various configurations illustrated in Japanese Patent Application No. 2000-292546 can be used.

Also, the opening portion opened facing the converging optical system 17 at the tip face of the cover 37 is covered with a protective glass cover 44.

Also, with the present embodiment, an ID unit 45 (see FIG. 1) which generates identification information (abbreviated as ID) unique to the optical scanning probe 2 is provided to the optical scanning probe 2, and the ID of the ID unit 45 is read by the computer 24.

The computer 24 makes reference to the optical properties of the optical scanning probe 2 from the ID, and thus can determine an adjustment range and the like necessary for setting to a state of optimal optical properties, and set to a state of optimal optical properties quicker than with a case of no making reference to the ID.

Figure 4A:
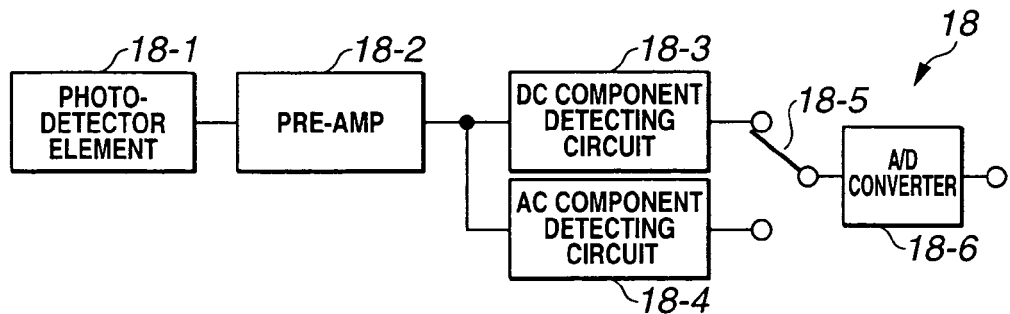
FIG. 4A is a block diagram illustrating the configuration of light detecting means.

FIG. 4A illustrates the configuration of light detecting means 18.

The light detecting means 18 comprise a photo-detector element 18-1, a pre-amp 18-2 for amplifying signals obtained by photo-electric conversion at the photo-detector element 18-1, a DC component detecting circuit 18-3 for detecting DC components of signals amplified at the pre-amp 18-2, an AC component detecting circuit 18-4 for detecting AC components of the signals amplified at the pre-amp 18-2, a switch 18-5 for selecting output signals from the DC component detecting circuit 18-3 and the AC component detecting circuit 18-4, and an A/D converter 18-6 for performing A/D conversion of signals selected at the switch 18-5, with the digital signals output from the A/D converter 18-6 being input to the computer 24.

Note that the switch 18-5 is switched over by the computer 24. In the setting mode, switching is performed to the DC component detecting circuit 18-3 side at first, and to the AC component detecting circuit 18-4 side later, the same as the observation mode.

Figure 4B:
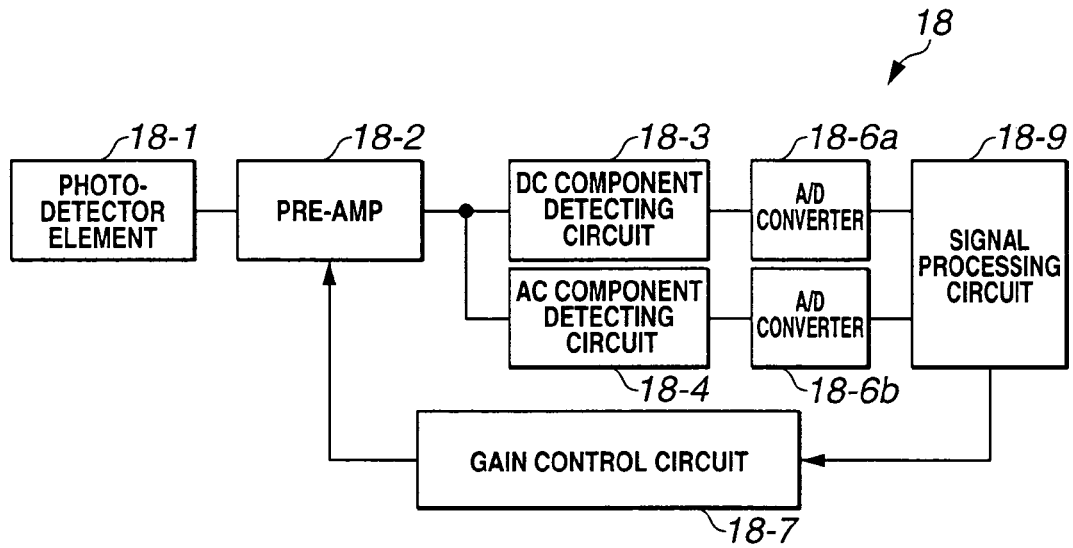
FIG. 4B and FIG. 4C are each block diagrams illustrating the configuration of light detecting means according to a modification.

A configuration such as the first modification shown in FIG. 4B may be used instead of the configuration in FIG. 4A.

In FIG. 4B, the configuration in FIG. 4A is not provided with the switch 18-5, but rather the output of the DC component detecting circuit 18-3 is subjected to A/D conversion with an A/D converter 18-6*a* and input to a signal processing circuit 18-7, and the output of the AC component detecting circuit 18-4 is subjected to A/D conversion with an A/D converter 18-6*b* and input to a signal processing circuit 18-9. Further, the signal processing circuit 18-9 adjusts the gain of the pre-amp 18-2 through the gain control circuit 18-7 according to the input signal level.

Figure 4C:
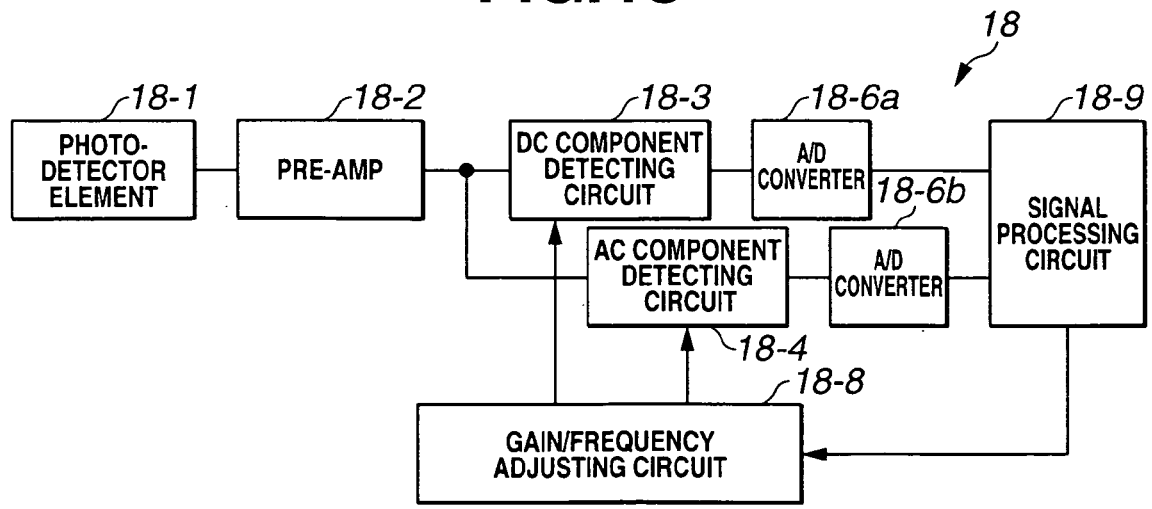

Also, a configuration such as the second modification shown in FIG. 4C may be used instead of the configuration in FIG. 4B.

In FIG. 4C, with the configuration in FIG. 4B, the signal processing circuit 18-9 adjusts the frequency for detecting the gain and AC component of the DC component detecting circuit 18-3 and AC component detecting circuit 18-4 with a gain/frequency adjusting circuit 18-8 instead of the gain control circuit 18-7, according to the signal levels input.

Next, the operation of the present embodiment will be described with reference to the flowchart shown in FIG. 5.

First, as shown in FIG. 1, the optical scanning probe 2 is connected to the observation apparatus main unit 3. Upon turning on the electric power, the computer 24 reads in the ID of the ID unit 45 provided to the optical scanning probe 2, as indicated by step S1.

Next, as indicated in step S2, the optical path length adjusting jig 7 is attached to the optical scanning probe 2. Subsequently, as shown in step S3, input of instructions for starting optical path adjustment is made from a keyboard or the like to the computer 24.

Accordingly, as shown in step S4, the computer 24 inserts the shutter 27 into the optical path of the optical path length variation mechanism 20. That is to say, the shutter 27 is closed. Accordingly, the light emitted from the tip of the single mode fiber 14 is shielded by the shutter 27, so that the light emitted from the tip of the single mode fiber 14 does not return to the tip thereof again. That is to say, the state is set to one where interference does not occur.

Subsequently, the computer 24 sends a driving signal to the motor 28, and the motor 28 is rotated so as to move the reference member 6 in the optical axis direction of the converging optical system 17, and processing is performed for setting the reference member 6 to a state wherein the signal intensity detected by the DC component detecting circuit 18-3 of the light detecting means 18 in that state is greatest (maximal).

Figure 6:
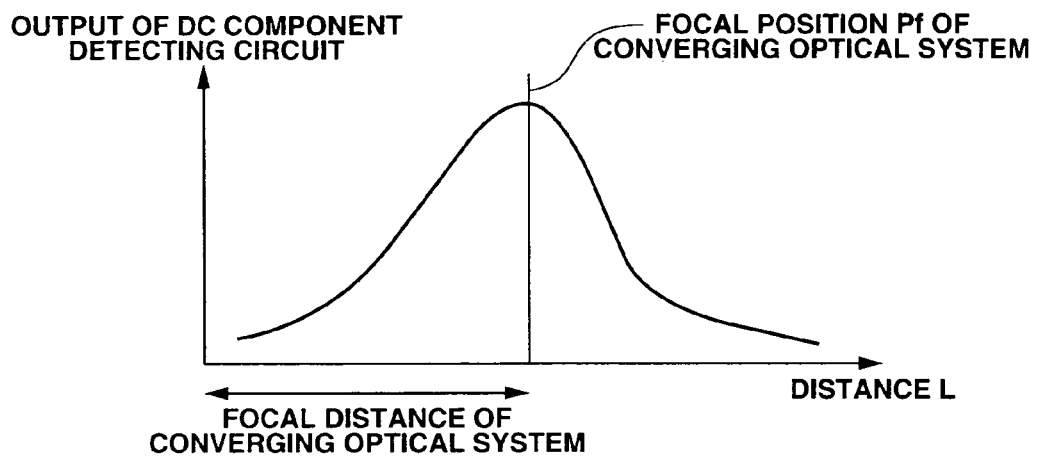
FIG. 6 is a diagram illustrating output properties of a DC component detecting circuit in the event that an optical path length adjusting jig is moved in the state that the shutter is closed in step S4 in FIG. 5.

The signal intensity detected by the DC component detecting circuit 18-3 is the greatest at the point that the reference member 6 of the optical path length adjusting jig 7 is set to the focal position Pf of the converging optical system 17 as shown in FIG. 6. In FIG. 6, the horizontal axis indicates the distance L from the converging optical system 17 to the surface of the reference member 6 of the adjusting jig 7, and the vertical axis indicates the output of the DC component detecting circuit 18-3.

That is to say, as shown in step S5, the position of the surface of the reference member 6 of the optical path length adjusting jig 7 is made to accord the focal position Pf of the converging optical system 17.

Thus, the position of the surface of the reference member 6 of the optical path length adjusting jig 7 is set to the focal position Pf of the converging optical system 17, following which the shutter 27 is opened as shown in step S6, i.e., the shutter 27 is set outside of the optical path. Accordingly, the light emitting from the tip of the single mode fiber 14 returns to the tip hereof again. That is, set to a state where interference occurs.

Next, the computer 24 sends control signals to the moving device 23 of the optical path length variation mechanism 20, moves the mirror 22 in the optical axis direction, and sets the mirror 22 at a position where the detection output of the AC component detecting circuit 18-4 of the light detecting means 18 in that state is greatest (maximal).

Upon changing the optical path length of the optical path length variation mechanism 20 side, in the event that the optical path length of the going path and return path for the optical scanning probe 2 side in a state wherein the position of the surface of the reference member 6 is set to the focal position of the converging optical system 17 of the optical scanning probe 2 side, and the optical path length of the going path and return path wherein reference light is reflected off of the mirror 22 in the optical path length variation mechanism 20 side and returns, are within the range of distance (coherence length) where there is interference with low-coherence light, and the interference light is detected by the AC component detecting circuit 18-4. The AC component detecting circuit 18-4 detects the AC component thereof by detection of AC component passing through a filter, or the like.

That is to say, as indicated in step S7, the optical path length of the reference light for the optical path length variation mechanism 20 side is made to accord the optical length wherein the converging optical system 17 of the optical scanning probe 2 is at the focal position Pf, and the position of the mirror is set to determine the optical path length of the reference light such that it can be detected as interference light (according with the optical path length of the optical scanning probe 2 side).

In the event of bringing the cover glass 44 into contact with the body tissue for observation, better adjustment can be performed by filling the space between the reference member 6 and the cover glass 44 with a substance having a refractive index close to that of the organism. A substance having a close refractive index may be water or oil or gel, and one with a refractive index of around 1.3 to 1.5 is desirable.

Thus, adjustment can be performed in a precise manner by adjusting after matching the refractive index on the space between the reference member 6 and the cover glass 44 as to the object of measurement.

Subsequently, this setting mode ends, and the flow proceeds to the observation mode. That is to say, the optical path length adjusting jig 7 is removed, and the optical scanning probe 2 is inserted through the channel of the endoscope 32 and used.

In this case, the converging optical system 17 is two-dimensionally scanned by the scanner 16, and only the light reflected at the focal position of the converging optical system 17 is input to the small tip face of the single mode fiber 15 set at a position confocal with the focus position thereof, and the light thereof is detected as signals of interference light where there has been interference with the reference light at the optical path length variation mechanism 20 side by the AC component detecting circuit 18-4 of the light detecting means 18.

The signals are stored in memory or the like of the computer 24, correlated with scanning information. Interference light signals corresponding to each scanned portion are imaged on the computer 24, and displayed as an image on the display device 25.

According to the present embodiment, a suitable optical properties state can be easily and smoothly set by the above-described setting mode, before making transition to the observation mode where actual observation is performed.

That is to say, with the setting mode, the going and returning optical path length (optical path length of the observation light side) for the optical scanning probe 2 in the state of the focal position Pf of the converging optical system 17, and the going and returning optical path length for the reference light, are accorded within the coherence length range of that light, and easily and smoothly set.

Accordingly, in the observation mode, observation images can be obtained in a state of suitable optical properties, i.e., in a state of high resolution at the focal position Pf.

Figure 7A:
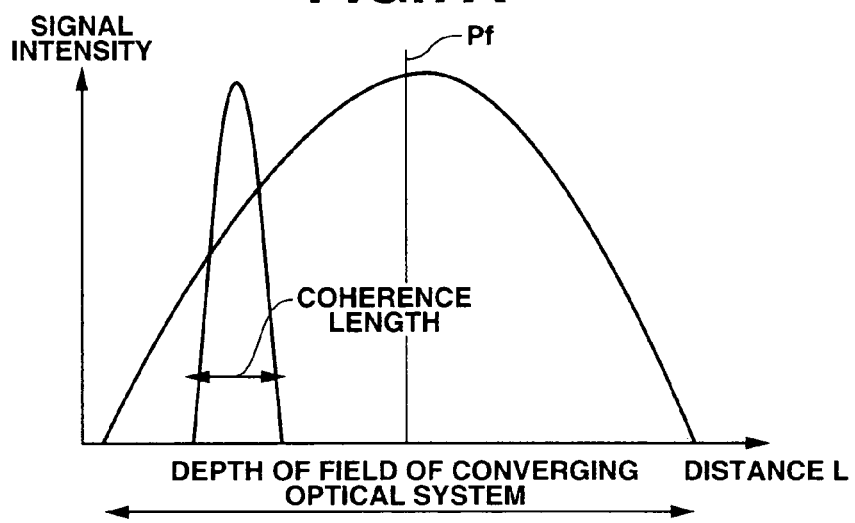
FIG. 7A and FIG. 7B are explanatory diagrams of adjustment precision permitted in the event that the coherence length of low-coherence light and the depth of field of the converging optical system differ.
Figure 7B:
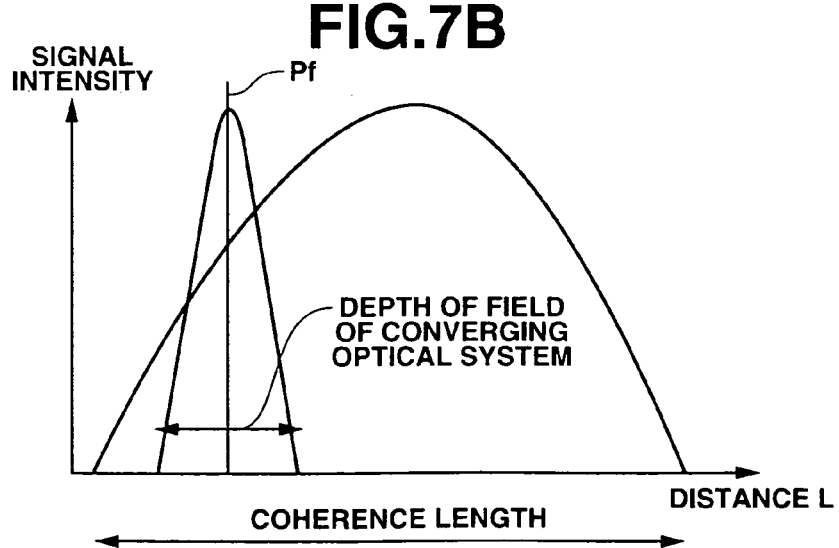

In the above description, description has been made that the surface of the reference member 6 of the optical path length adjusting jig 7 is set to the focal position Pf of the converging optical system 17, and the optical path length of the optical path length variation mechanism 20 side is made to accord the optical length in the state of the focal position Pf of the converging optical system 17, but in reality, cases shown in FIG. 7A and FIG. 7B can be conceived.

With FIG. 7A, the coherence length is short, and in the event that the depth of field of the converging optical system 17 is long in comparison therewith, setting the coherence length to around within the distance range of the depth of field of the converging optical system 17 (the optical path length by positional setting of the mirror 22 at the optical path length variation mechanism 20 side) is sufficient.

Also, FIG. 7B is a case opposite to that in FIG. 7A, wherein the coherence length is long, and in the event that the depth of field of the converging optical system 17 is short in comparison therewith, setting the position of the reference member 6 of the optical path length adjusting jig 7 side to around within the distance range of the coherence length is sufficient. It is needless to say that the best arrangement is to select a position where both cases can reach a peak.

Note that with the setting mode in the above description, description has been made that the reference member 6 is set while shielded by the shutter 27 so that no interference light occurs, but this may be performed using means which reduce light instead.

Also, in the description above, in FIG. 2 for example, description was made that of the light emitted from the small tip face of the single mode fiber 14, only the light reflected at the focal position (Pf) confocal with this tip face by the converging optical system 17 thereby can return to the tip face, but an arrangement may be made wherein a state close to this confocal relation is set so as to observe observation images.

That is to say, strictly setting conditions for satisfying a confocal relationship reduces the intensity of the light obtained, which may deteriorate the S/N, and there are cases wherein an observation with essentially good S/N can be obtained by setting conditions close to the confocal relation (e.g., widening the size of the tip face of the single mode fiber 14, so that light can be detected in the event that other confocal relation conditions are slightly departed from).

Also, the fiber used for the optical scanning probe 2 has been described as being a single mode fiber 14, but the present invention is not restricted to this, and may use a multi-mode fiber instead.

Also, the optical scanning probe 2 has been described as being insertable through a channel in the endoscope 32, but instead, the optical scanning probe 2 may be provided to the endoscope 32.

Also, with the setting mode in the above description, the surface position of the reference member 6 has been described as being set to the position where the intensity of the reflection light thereof as a mirror face reflecting light is greatest (maximal) in the event of according the surface of the reference member 6 to the focal position Pf of the converging optical system 17, but an arrangement may be made wherein reflecting portions and non-reflecting portions are formed in a repeating striped manner on the surface thereof, which is scanned by light with the scanner 16, and the reflected light thereof is detected, so as to set the surface position of the reference member 6 at a state wherein the amplitude of the contrast signal from the reflecting portions and the non-reflecting portions is greatest (maximal) for the detection output by the light detecting means 18.

Also, in the event of setting the position of the mirror 22 of the optical path length variation mechanism 20 side as well, an arrangement may be made wherein scanning is performed with light by the scanner 16, and in that state the mirror 22 is set at a position wherein the amplitude of the contrast signals is greatest (maximal).

Second Embodiment

Next, a second embodiment of the present invention will be described with reference to FIG. 8 through FIG. 11. FIG. 8 illustrates the configuration of an optical scanning observation apparatus 1B according to the second embodiment.

The optical scanning observation apparatus 1B is the optical scanning observation apparatus 1 shown in FIG. 1 having a configuration wherein the optical path length adjusting jig 7 and the driving device 5 are not necessary. The optical scanning observation apparatus 1B comprises an optical scanning probe 2B and an observation apparatus main unit 3B, with no optical path length adjusting jig 7 nor driving device 5 provided to the observation apparatus main unit 3B.

Instead, a piezoelectric device 51 is provided to the optical scanning probe 2B, functioning so that the tip thereof is movable in the optical axis direction of the converging optical system 17, and the piezoelectric device 51 is connected to the computer 24 with a cable 52, so that the piezoelectric device 51 can be driven by the computer 24 in the setting mode.

FIG. 9A and FIG. 9B illustrate the configuration at the tip side of the optical scanning probe 2B, FIG. 9A illustrates a state wherein a piezoelectric device 51 is not driven, for example, and FIG. 9B illustrates a state wherein the piezoelectric device 51 is driven and the piezoelectric device 51 portion is shrunk.

The optical scanning probe 2B basically has the tip side of the optical scanning probe 2 shown in FIG. 3 in a double structure, so that the inner side portion thereof can be moved in the optical axis direction of the converging optical system 17 with the piezoelectric device 51.

That is to say, with the optical scanning probe 2 shown in FIG. 3, the rear end of the scanner 16 was attached at the base member 36 fixing the sheath 31 and cover 37, but with the optical scanning probe 2B shown in FIG. 9, a hollow piezoelectric device 51 is attached to a base member 36 fixing a sheath 31 and a cover 37 (with a single mode fiber 15 or driving cable 43 passed therethrough), and the rear end of a scanner 16 for scanning the holder 40 is attached to the piezoelectric device 51 through a second base member 36b.

The end potion of a cable 52 is connected to the electrodes on both faces of the piezoelectric device 51 (facing each other on the optical axis direction of the converging optical system 17), driving signals are applied from the computer 24 for example, the piezoelectric device 51 shrinks in the optical axis direction of the converging optical system 17 according to the level thereof, and the focal position of the converging optical system 17 moves backwards by the shrinking thereof.

Also, a second cover 37b is attached to the second base member 36b, and a second cover glass 44b is attached to the opening at the font end of the cover 37b.

The portion covered by this cover 37b is a movable portion 53. Note that the second cover 37b is not always necessary.

Figure 10:
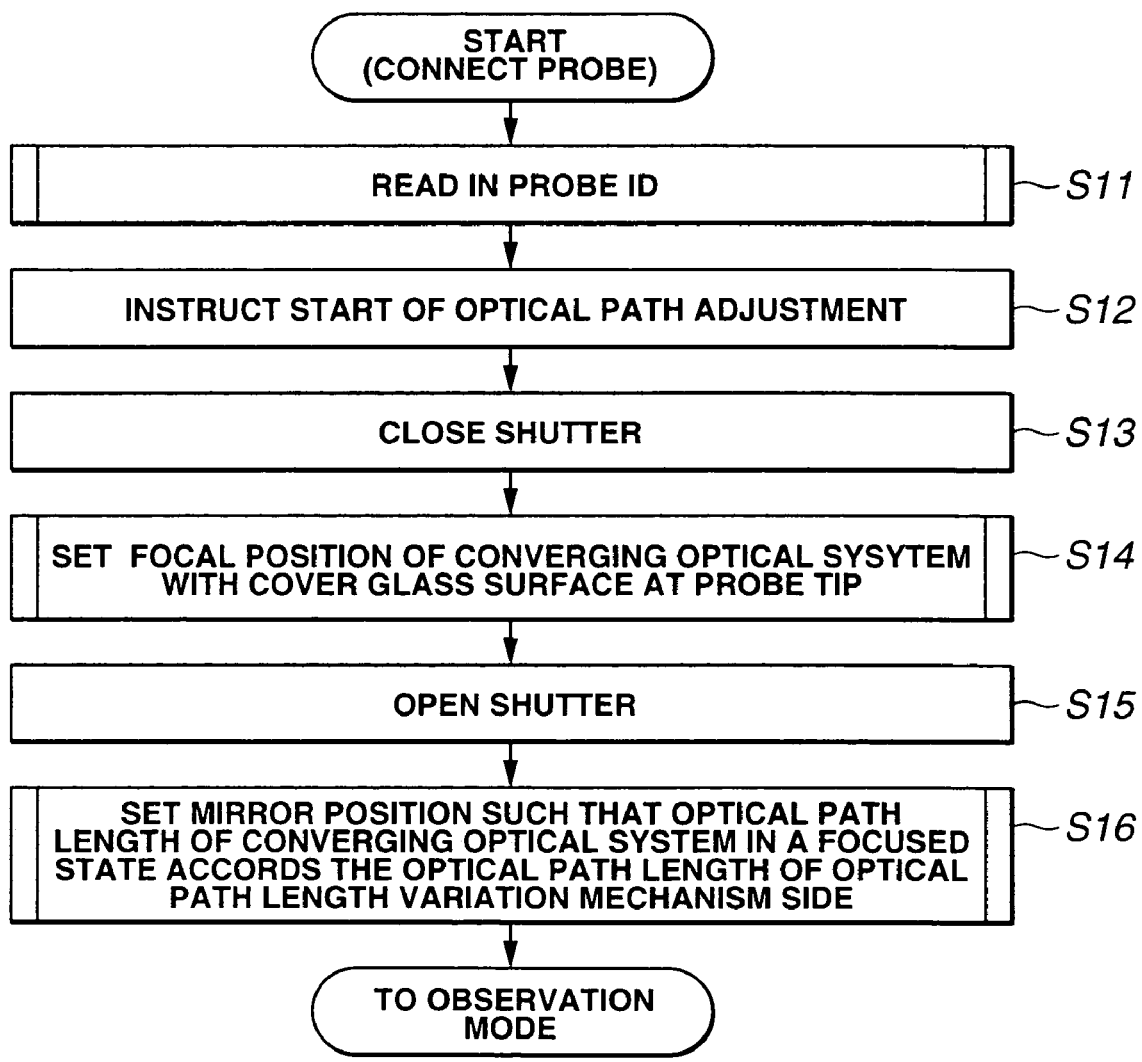
FIG. 10 is a flowchart illustrating the processing procedures for setting the second embodiment to a state wherein optical properties are suitable.

Next, the operations of the present embodiment will be descried with reference to the flowchart in FIG. 10.

Figure 5:
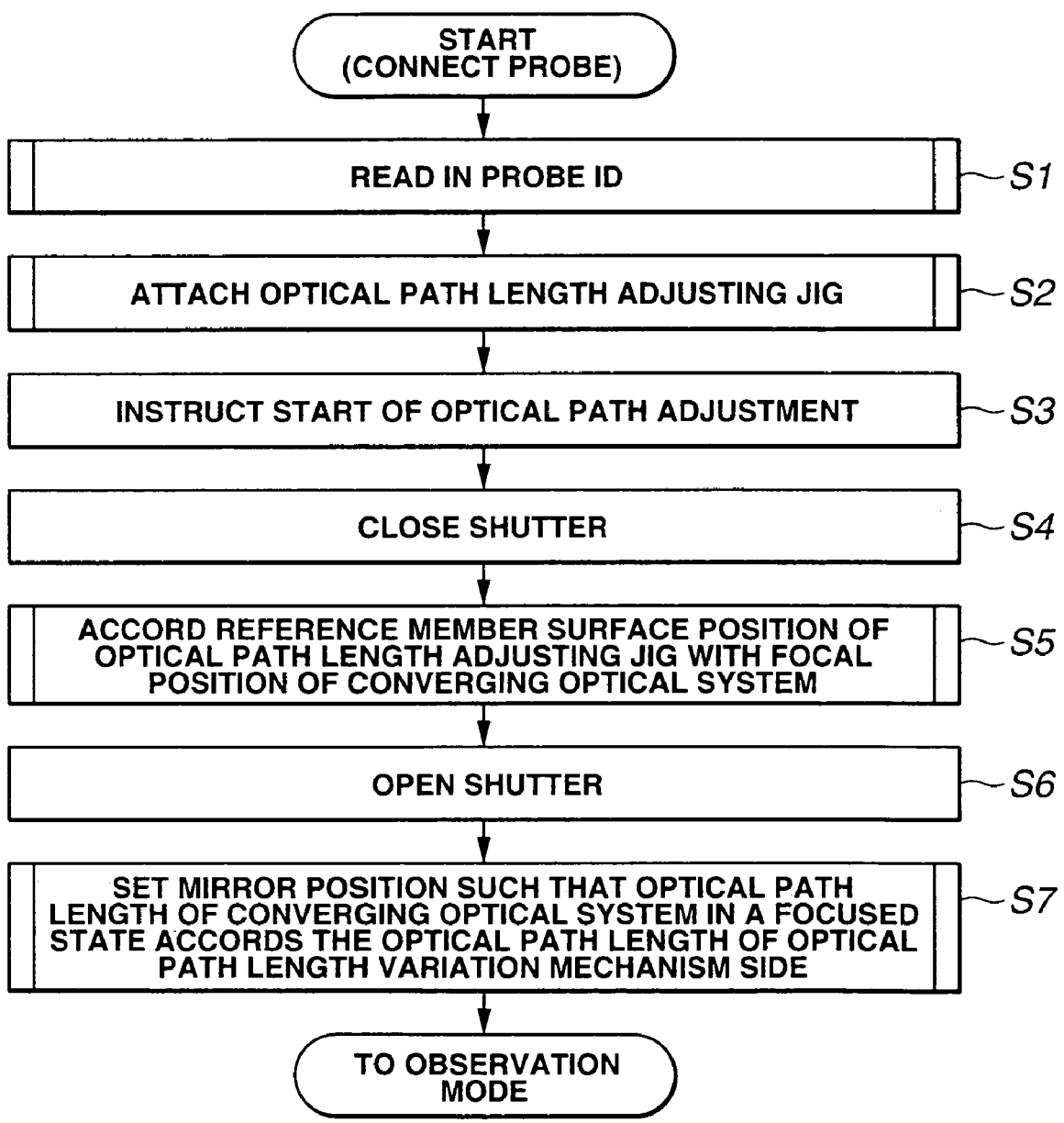
FIG. 5 is a flowchart illustrating the processing procedures for setting the first embodiment to a state wherein optical properties are suitable.

The processing in the flowchart in FIG. 10 omits the processing of step S2 in the processing in FIG. 5, and processing (step S14) for setting the focal position of the converging optical system 17 to the surface position of the cover glass 44 of the tip of the optical scanning probe 2B by driving the piezoelectric device 51 is performed instead of step S5.

Accordingly, the operations thereof will be described briefly. Upon the optical scanning probe 2B being connected to the observation apparatus main unit 3B and turning on the electric power, the ID of the probe is read in step S11 in the same way as described in FIG. 5, and next the instructions for starting optical path adjustment are made in step S12. As indicated in step S13, the computer 24 then closes the shutter 27, so that interference light is not detected.

The computer 24 then transmits a driving signal to the piezoelectric device 51, so as to gradually shrink the piezoelectric device 51, whereby the focus position of the converging optical system 17 moves toward the converging optical system 17 side on the optical axis, and at this time sets a state wherein the output of the DC component detecting circuit 18-3 of the light detecting means 18 is greatest.

Upon the converging optical system 17 being moved and the focal position thereof being set at the surface position of the cover glass 44 at the tip (of the optical scanning probe 2B), this creates a state wherein reflected light at the surface thereof is detected, and in this state the output of the DC component detecting circuit 18-3 of the light detecting means 18 is greatest.

That is to say, this processing is processing for setting the focal position of the converging optical system 17 to the position of the surface of the cover glass 44 at the tip of the optical scanning probe 2B, as indicated in step S14.

Following this processing being performed, the shutter 27 is opened, and placed in a state where the interference light is detected, as indicated in step S15.

As indicated in step S16, the position of the mirror 22 is set such that the optical path length at the optical path length changing mechanism side accords the optical path length for reflected light returning from the focal position with the focal position of the converging optical system 17 set at the position of the surface of the cover glass 44.

That is to say, the position of the mirror 22 is set to a state wherein the output of the AC component detecting circuit 18-4 of the light detecting means 18 is greatest while moving the mirror 22.

Following ending of this processing, the processing of the setting mode ends, and the flow can proceed to the observation mode.

Note that in this case, the surface of the cover glass 44 is the focal position, so in order to set the focal position at a desired distance from the surface of the cover glass 44, signals of a corresponding level are applied to the piezoelectric device 51, and the mirror 22 is moved and set in a direction away by a distance equal to that distance.

As can be understood from this description, with the present embodiment, the optical path length adjusting jig 7 can be made unnecessary, and the focal position of the converging optical system 17 can be set changeably in the depth-wise direction, and the optical path length of the optical path length variation mechanism 20 side may also be made variable synchronously therewith, so as to obtain optical scanning images in the depth-wise direction.

That is to say, with the present embodiment, two-dimensional images can be obtained by scanning the converging optical system 17 with the scanner 16, and three-dimensional images can be obtained by driving the piezoelectric device 51 to scan in the depth-wise direction, as well.

Figure 11:
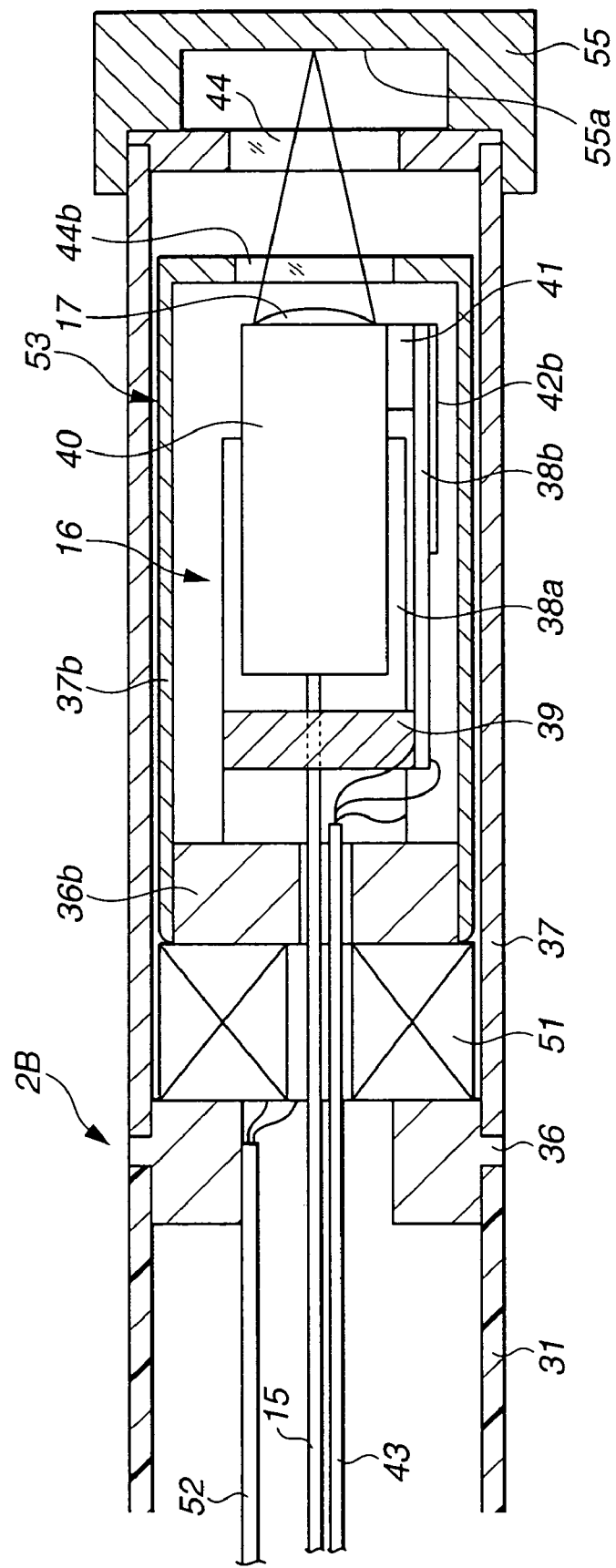
FIG. 11 is a cross-sectional diagram illustrating an optical scanning probe with an adjusting jig attached.

With the above-described description, the focal position of the converging optical system 17 has been described as being able to be set at the surface position of the cover glass 44 by shrinking the piezoelectric device 51, but in the event that the range of variation with the piezoelectric device 51 is narrow, an arrangement may be made wherein an adjusting jig 55 shaped like a cap is attached to the tip face of the optical scanning probe 2B as shown in FIG. 11, and the focal position of the converging optical system 17 is set at a reference face 55a on a recessed portion of the adjusting jig 55.

In this case, an optical scanning image is obtained in a state wherein the position of the reference face 55a distanced from the tip face of the optical scanning probe 2B is the focal position.

Third Embodiment

Figure 12:
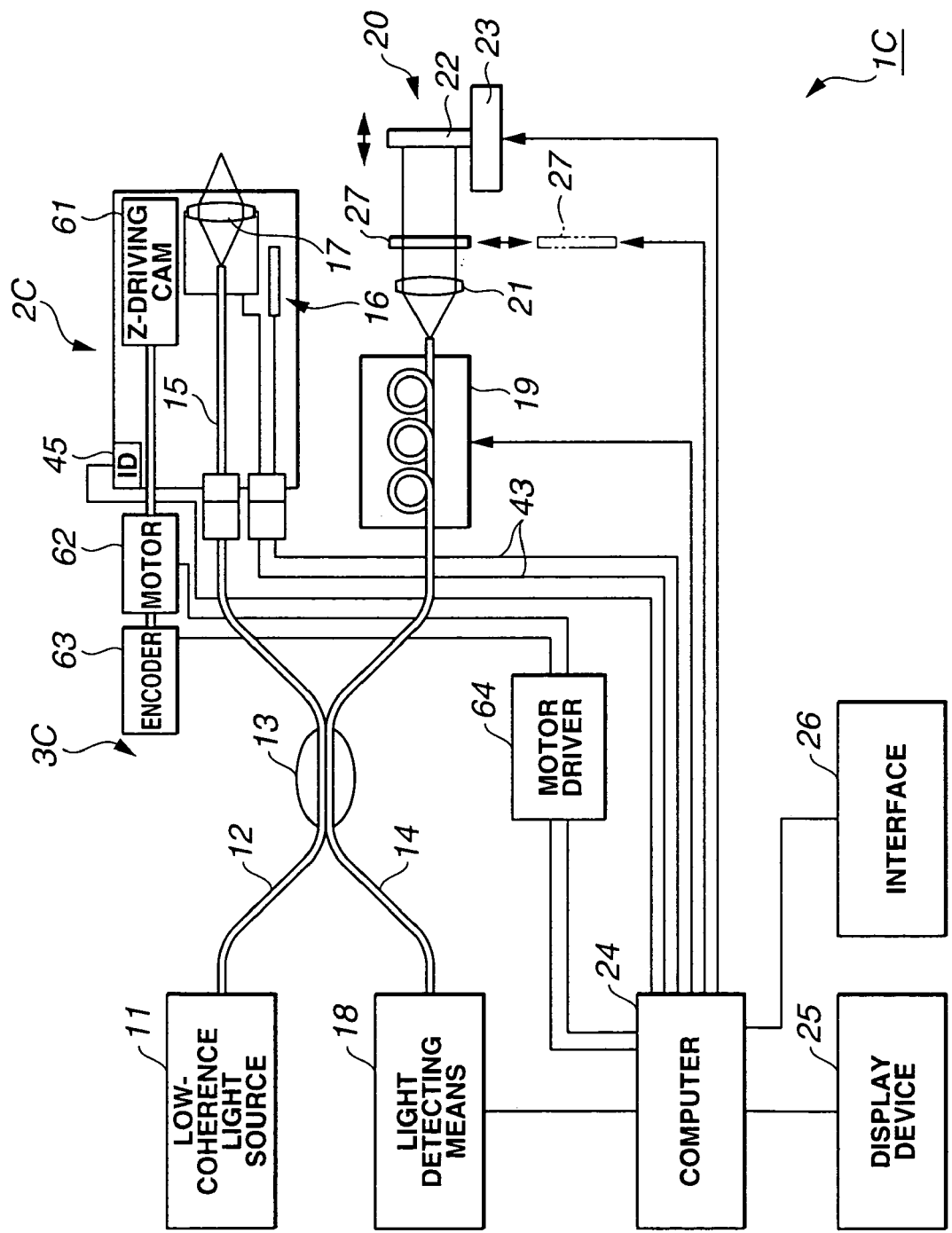
FIG. 12 is a diagram illustrating the overall configuration of an optical scanning observation apparatus according to a third embodiment of the present invention.

A third embodiment of the present invention will be described with reference to FIG. 12 through FIG. 15. FIG. 12 illustrates an optical scanning observation apparatus 1c according to the third embodiment of the present invention. The optical scanning observation apparatus 1C comprises an optical scanning probe 2C and an observation apparatus main unit 3C.

This optical scanning probe 2C is provided with a Z-driving cam 61 instead of the piezoelectric device 51 in the optical scanning probe 2B in FIG. 8, so that the tip side including the converging optical system 17 is movable, with the Z-driving cam 61 being driven by a motor 62 provided toward at the close side thereof. Also, the rotational shaft of the motor 62 is connected to an encoder 63. The motor 62 and the encoder 63 are connected to the computer 24 via the motor driver 64.

The motor 62 is driven by the motor driver 64 under control of the computer 24, and the output signals of the encoder 63 for detecting the rotational position thereof are input to the computer 24 via the motor driver 64.

Figure 13:
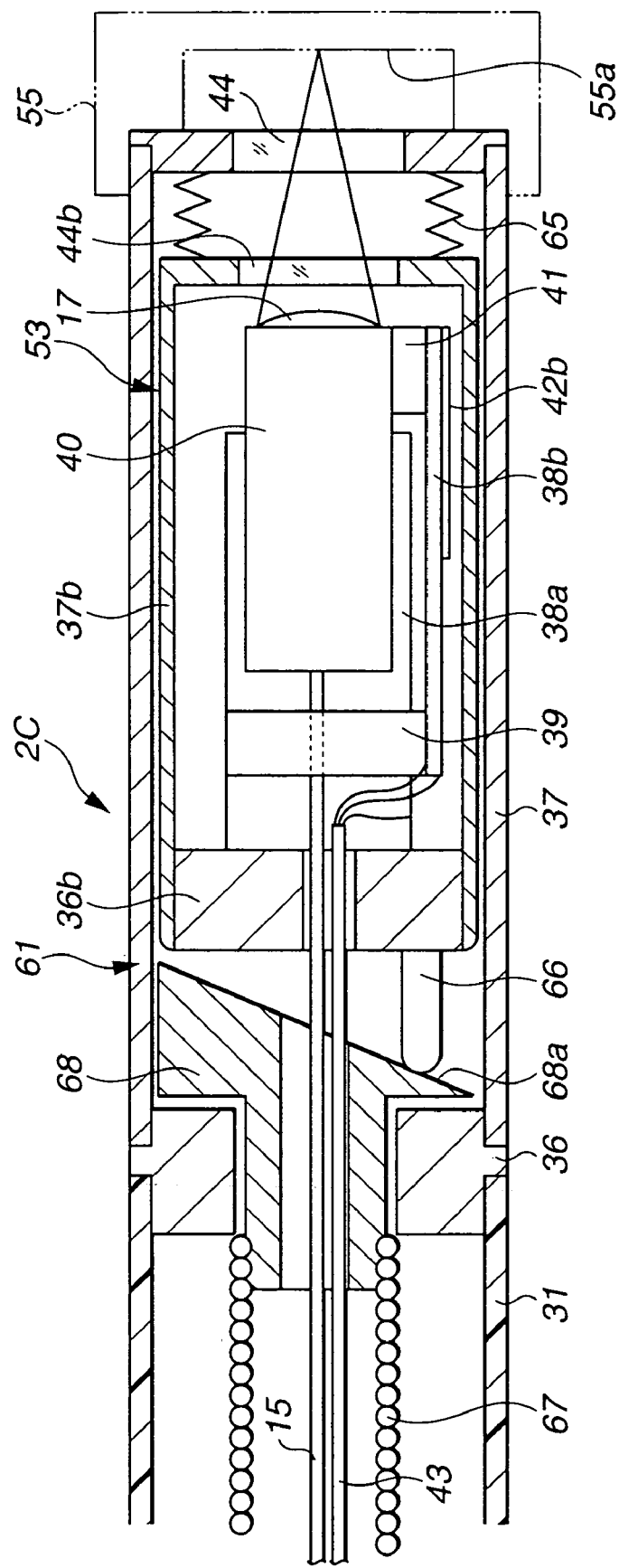
FIG. 13 is a cross-sectional diagram illustrating the configuration of the tip side of the optical scanning probe.

FIG. 13 illustrates the configuration at the tip side of the optical scanning probe 2C. The movable portion 53 described in FIG. 9 is provided on the tip side of this optical scanning probe 2C, and the tip face of the movable portion 53 is pressed backwards by a spring 65, with a pin 66 protruding backwards from the back end face of the movable portion 53.

Also, a flexible shaft 67 which is linked to the rotational shaft of the motor 62 and is rotably driven is inserted through the sheath 31, a rotating member 68 provided with a inclined face 68a formed by diagonally notching the tip face thereof is attached on the tip of the flexible shaft 67, with this rotating member 68 being rotably supported by the base member 36.

The movable portion 53 is pressed backwards by the spring 65, and accordingly the pin 66 supports the state of the inclined face 68a of the rotating member 68 being pressed. Upon the rotating member 68 being rotated by the motor 62 through the flexible shaft 67, the pin 66 is pressed by the inclined face 68a of the rotating member 68 and the movable portion 53 moves so as to advance or retreat in the optical axis direction of the converging optical system 17, i.e., in (the Z-axial direction on the coordinates system in FIG. 3, that is, in the depth-wise direction toward the subject).

By the movable portion 53 repeating the advancing and retreating motion in the optical axis direction of the converging optical system 17, the focal position of the converging optical system 17 also moves in the optical axis direction by an amount the same as the advancing and retreating of the movable portion 53. The focal position of the converging optical system 17 at the time of this moving can move as far as behind the tip surface of the cover glass 44.

In the event that the range of movement is narrow, attaching a jig 55 such as indicated by the dotted line in FIG. 13 enables movement of the focal position in a range including the surface of the jig 55, i.e., a range including the reference face 55a.

Figure 14:
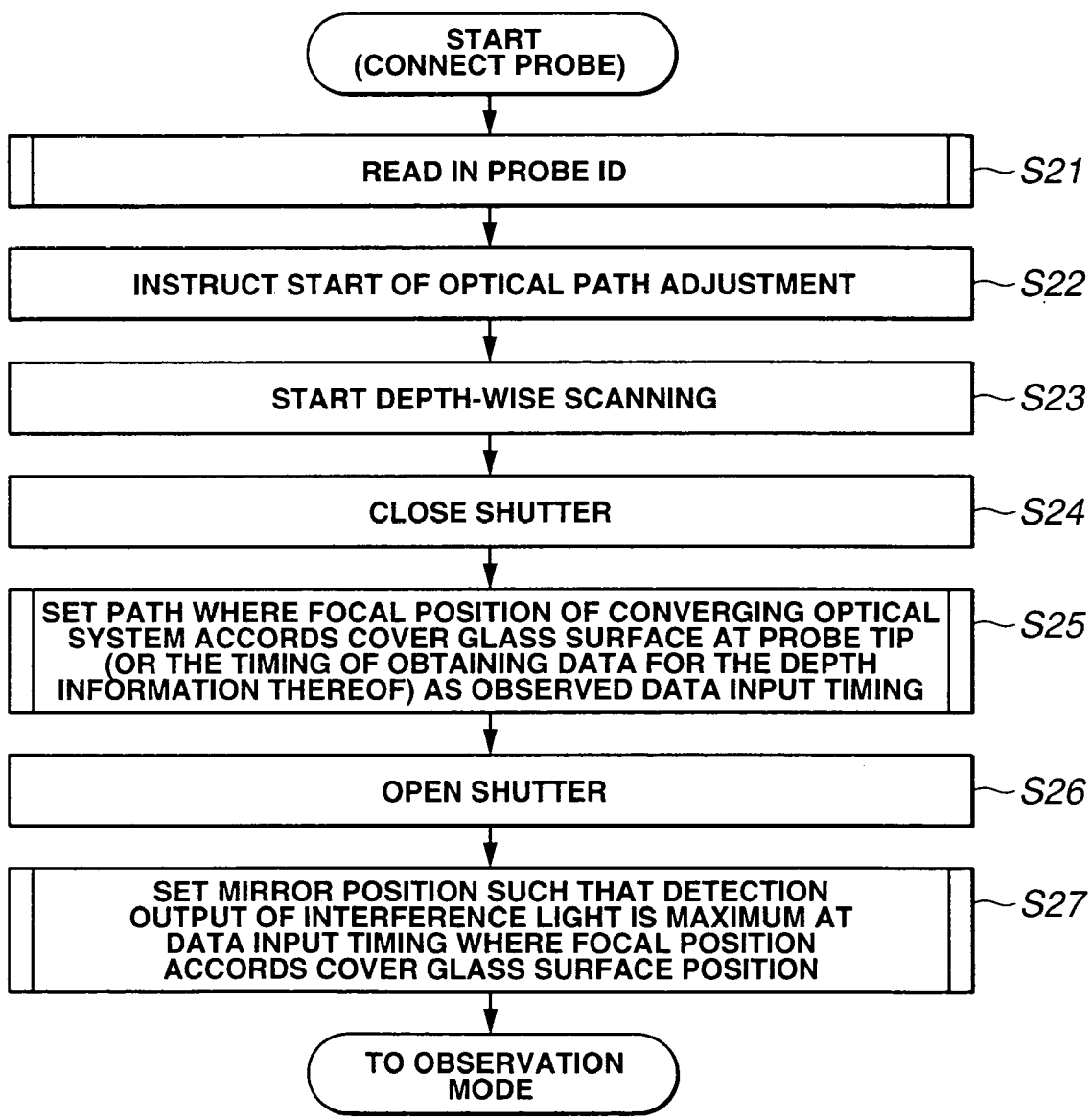
FIG. 14 is a flowchart illustrating the processing procedures for setting the third embodiment to a state wherein optical properties are suitable.

FIG. 14 illustrates a flowchart of the operations of the present embodiment. Upon the optical scanning probe 2C being connected to the observation apparatus main unit 3C and turning on the electric power, the ID of the optical scanning probe 2C is read in step S21. Next, the instructions for starting optical path adjustment are made in step S22.

The instructions start rotation of the motor 62 and scanning of the converging optical system 17 in the optical axis direction (also referred to as depth-wise direction), as well as the movable portion 53, as indicated in step S23. Also, as indicated in step S24, the shutter is closed by control of the computer 24, so that interference light is not detected.

The depth of the state wherein the output of the DC component detecting circuit 18-3 of the light detecting means 18 is greatest or the timing of the depth thereof is detected by the output of the encoder 63. That is to say, at the point that the focal position of the converging optical system 17 accords the surface position of the cover glass 44, the output of the DC component detecting circuit 18-3 is the greatest, and the timing at that time can be detected from the output of the encoder 63.

That is to say, as indicated in step S25, processing is performed so as to set the depth where the focal position of the converging optical system 17 accords the surface position of the cover glass 44 of the tip of the optical scanning probe 2C (or the input timing of data for the depth information thereof) is set to the input timing for observation data.

Subsequently, the shutter 27 is opened as indicated in step S26, and as indicated in the subsequent step S27, the position of the mirror 22 is set so that the output of the AC component detecting circuit 18-4 of the light detecting means 18 (i.e., the detection output of interference light) is greatest at the input timing for data where the focal position of the converging optical system 17 accords the surface position of the cover glass.

Subsequently, the flow proceeds to the observation mode.

Figure 15:
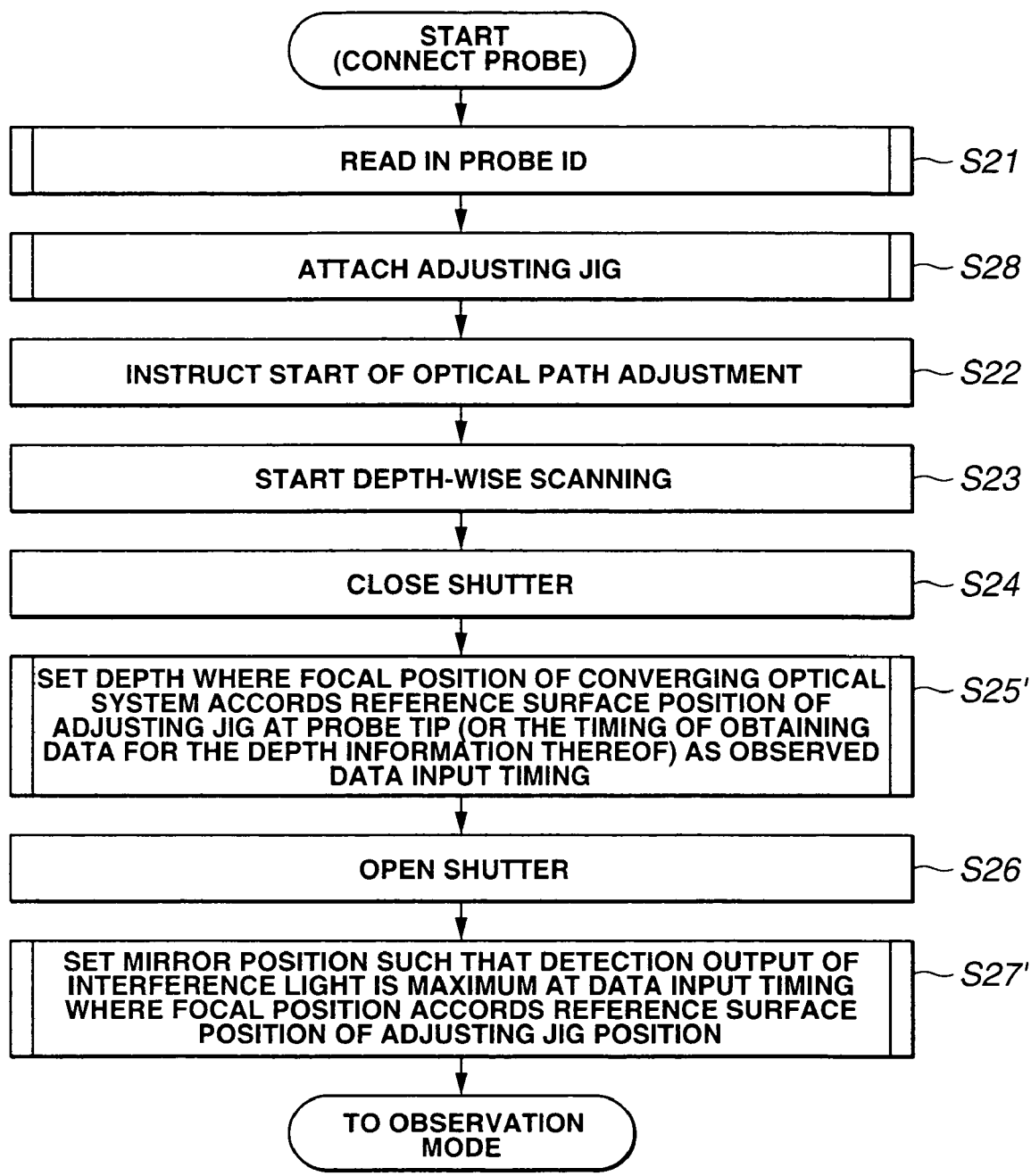
FIG. 15 is a flowchart illustrating the processing procedures for setting to a state wherein optical properties are suitable using the adjusting jig.

On the other hand, in the event that the moving range is narrow and the adjustment jig 55 is used, the processing indicated in FIG. 15 is performed. The processing shown in FIG. 15 is performing the processing for attaching the adjusting jig 55 between the steps S21 and S22 in FIG. 14 (step S28).

Also, step S25' is performed instead of step S25 in FIG. 14. This step S25' is equivalent to substituting the surface position of the cover glass 44 at the probe tip in step S25 with the reference face 55a of the adjustment jig 55. Also, step S27 in FIG. 14 is changed as indicated by step S27' in FIG. 15, in the same way. Here as well, the surface position of the cover glass 44 at the probe tip is substituted with the reference face 55a of the adjustment jig 55.

According to the present embodiment, inputting the output of the light detecting means 18 in an optimal optical state by output of the encoder 63 allows a two-dimensional image to be obtained with regard to the subject in a focused state in the same way as with the second embodiment, and changing the position of the mirror 22 with the optical path length variation mechanism 20 also enables a three-dimensional image to be obtained in the same way as described with the second embodiment.

Fourth Embodiment

Figure 16:
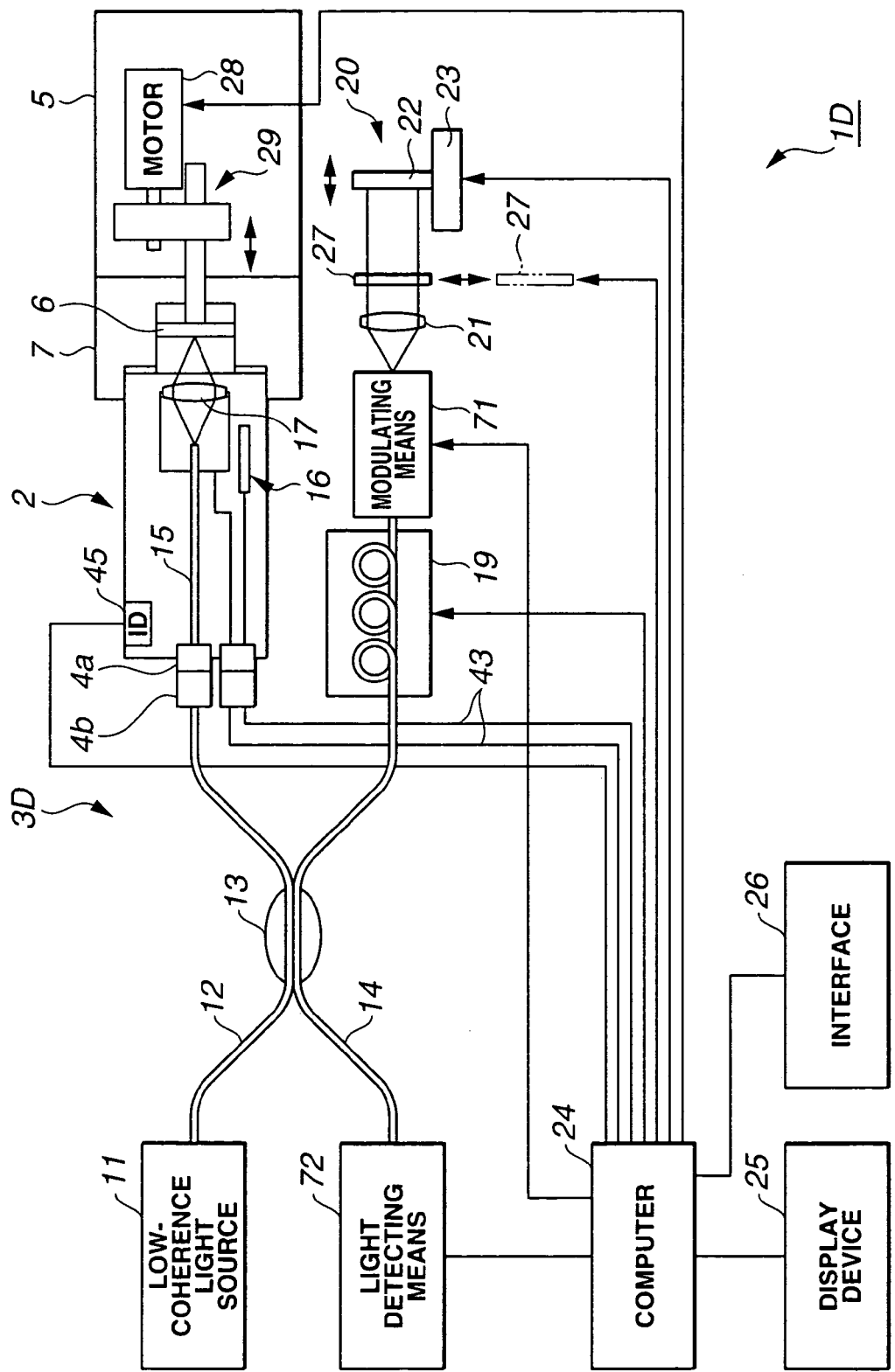
FIG. 16 is a diagram illustrating the overall configuration of an optical scanning observation apparatus according to a fourth embodiment of the present invention.

Next, a fourth embodiment of the present invention will be described with reference to FIG. 16 and FIG. 17. FIG. 16 illustrates an optical scanning observation apparatus 1D according to the fourth embodiment of the present invention. This optical scanning observation apparatus 1D comprises the optical scanning probe 2 and an observation apparatus main unit 3D.

The observation apparatus main unit 3D according to the present embodiment has modulating means 71 between the tip of the single mode fiber 14 shown in FIG. 1 and the optical path length variation mechanism 20, for performing modulation, and is controlled so as to perform modulation operations by the computer 24 in the observation mode or event of using the reference light at the optical path length variation mechanism 20 side.

Figure 17:
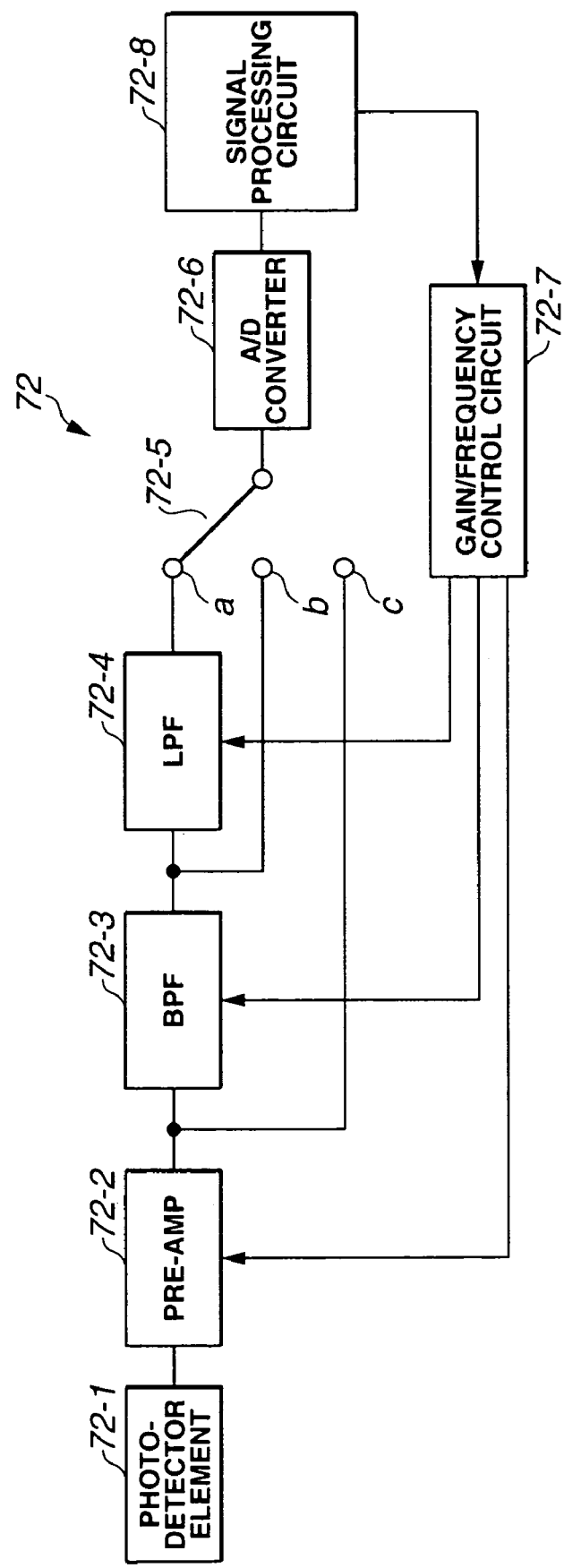
FIG. 17 is a block diagram illustrating the configuration of light detecting means.

Light detecting means 72 in this case are configured as shown in FIG. 17.

The light detecting means 72 shown in FIG. 17 comprise a photo-detector element 72-1 for receiving light irradiated from the end face of the single mode fiber 14, a pre-amp 72-2 for amplifying signals obtained by photo-electric conversion at the photo-detector element 72-1, a band-pass filter 72-3 (abbreviated as BPF) for passing frequency components of the signals with frequency below the modulating frequency of the modulating means 71 amplified at the pre-amp 72-2, a low-pass filter 72-4 for detecting envelope signal components which have passed through the band-pass filter 72-3, i.e., for detecting low-frequency components, a switch 72-5 for selecting between contacts a, b, and c, to which have been connected the output of the pre-amp 72-2, the output which has passed through the band-pass filter 72-3, and the output which has passed through the low-pass filter 72-4, an A/D converter 72-6 for performing A/D conversion of signals selected at the switch 72-5, a signal processing circuit 72-8 where the output from the A/D converter 72-6 is input, and a gain/frequency control circuit 72-7 for controlling the gain of the pre-amp 72-2, band-pass filter 72-3, and low-pass filter 72-4, based on the output from the signal processing circuit 72-8.

The band-pass filter 72-3 and low-pass filter 72-4 form means for demodulating the modulating means 71. In the event of using the modulating means 71, the a and b of the switch 72-5 are switched over as appropriate.

In the event of closing the shutter 27 and performing optical path adjustment, this is set to contact c, and is adjusted so that the output thereof is greatest. Note that the control of switching of the switch 72-5 is performed by the computer 24. Other configurations are the same as with FIG. 1.

With the present embodiment, the reference light side is modulated by the modulating means 71, so setting of the optical path length for the reference light and detection of interference light in the observation mode can be performed in a state wherein the light component interfering with the modulated reference light has a good S/N.

Figure 18:
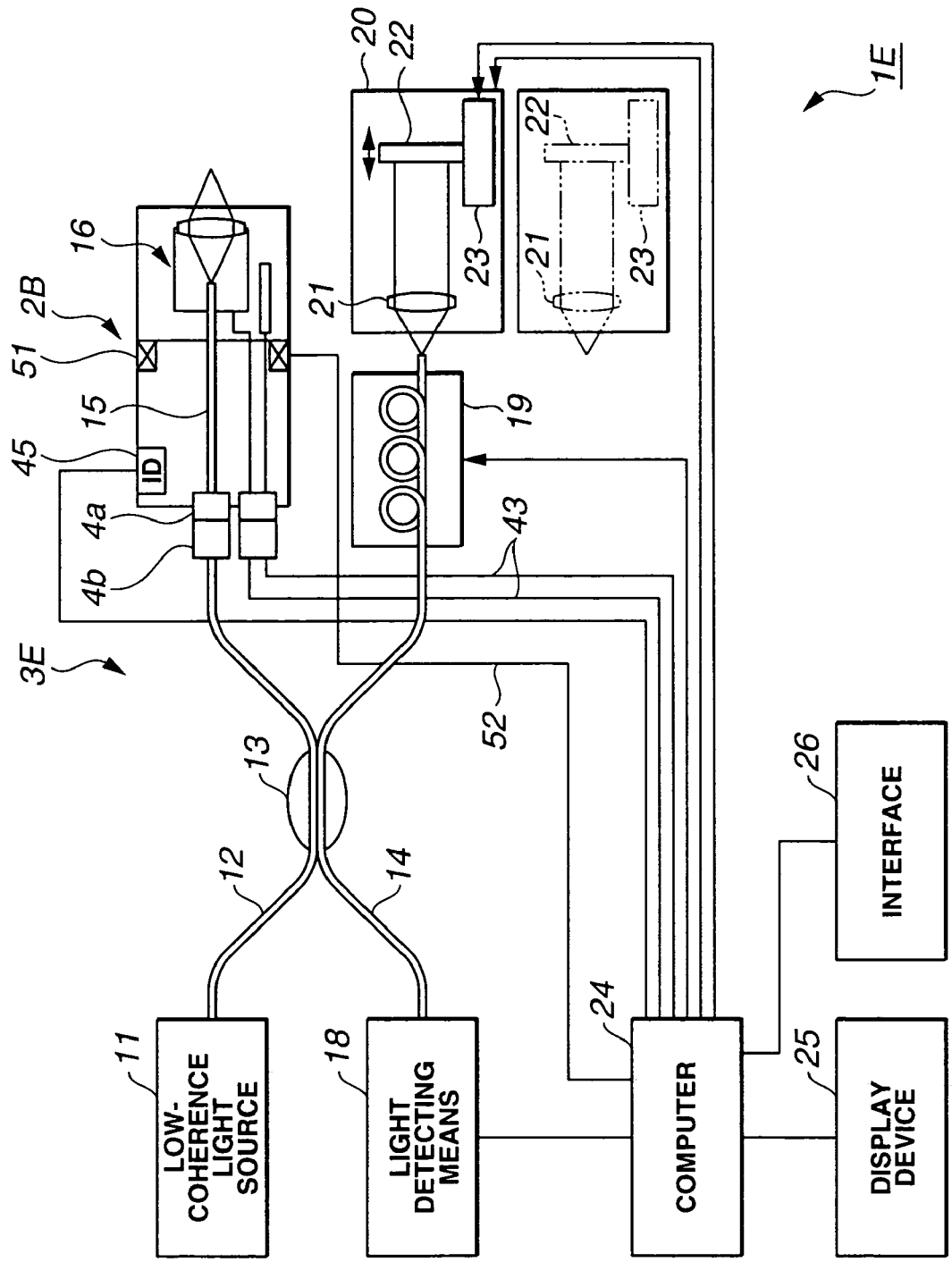
FIG. 18 is a diagram illustrating the overall configuration of an optical scanning observation apparatus according to a modification.

FIG. 18 illustrates an optical scanning observation apparatus 1E according to a modification. In FIG. 8 for example, the shutter 27 of the optical path length variation mechanism 20 can open and close, but with this optical scanning observation apparatus 1E, the optical path length variation mechanism 20 itself is detachable from the optical path at the tip of the single mode fiber 14, thereby forming an apparatus main unit 3E wherein the shutter 27 is unnecessary.

That is to say, in FIG. 8, the shutter 27 is retracted from (and extended into) the optical path in the setting mode by the computer 24, but in FIG. 18, the optical path length variation mechanism 20 is retracted from (and extended into) the optical path. In FIG. 18, the state wherein the optical path length variation mechanism 20 is extended into the optical path is illustrated with solid lines, and the state of retraction therefrom is indicated by two-dot broken lines.

Note that the modification in FIG. 18 has been applied to the apparatus shown in FIG. 8, but may be applied to other apparatuses as well.

Also, a light reducing filter or the like wherein the intensity of returning reflected light is reduced may be used instead of the shutter 27.

The following is a description of multiple embodiments of the optical scanning observation apparatus (also called optical imaging apparatus) according to the present invention, with reference to the drawings.

Fifth Embodiment

Figure 19:
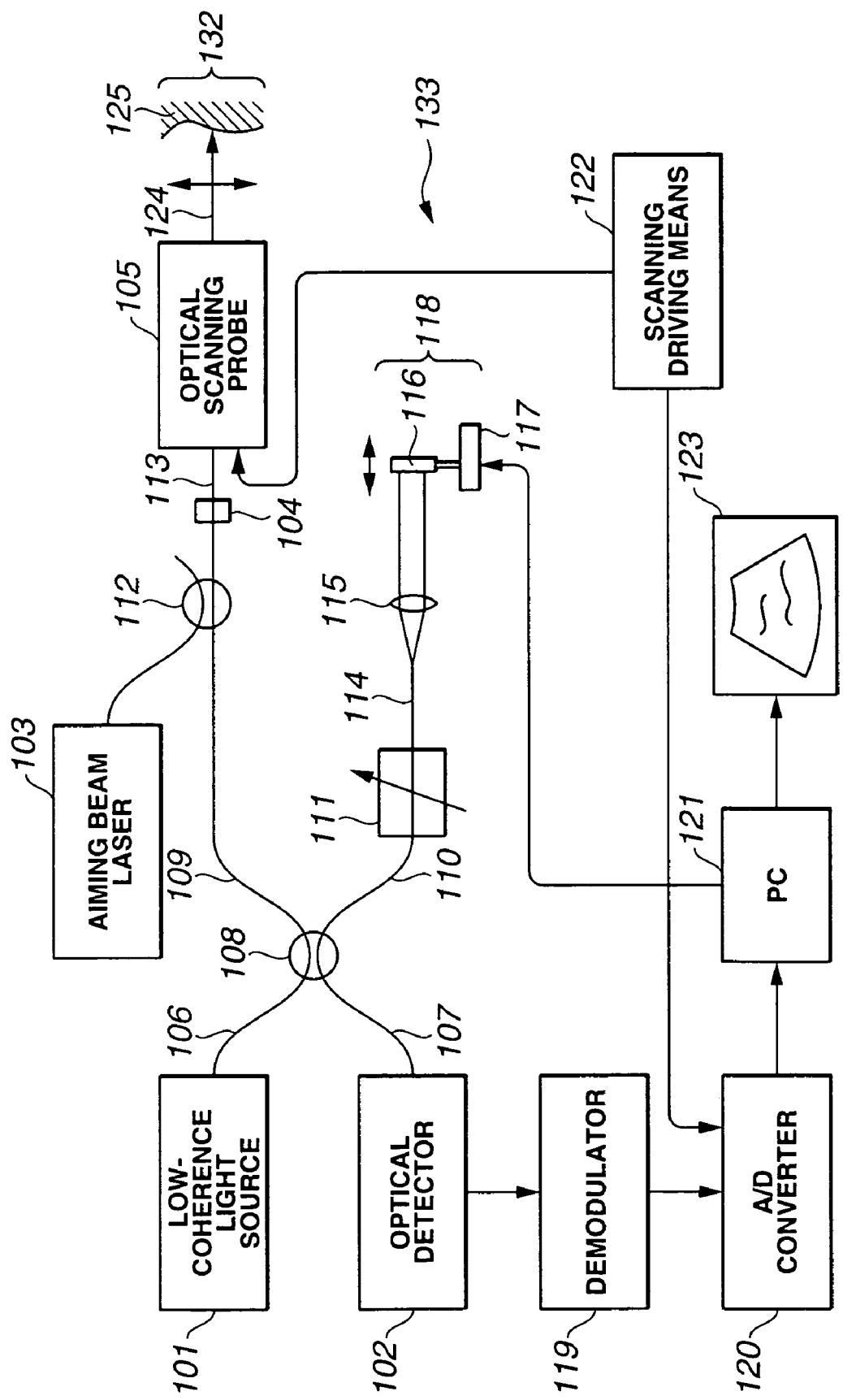
FIG. 19 is a configuration diagram illustrating the configuration of an optical scanning observation apparatus according to a fifth embodiment of the present invention.

First, the configuration of the optical scanning observation apparatus according to a fifth embodiment will be described with reference to FIG. 19 and FIG. 20. FIG. 19 illustrates the configuration of the optical scanning observation apparatus according to the fifth embodiment, and FIG. 20 illustrates a schematic configuration of the tip of an optical scanning probe 105.

In FIG. 19, near-infrared low-coherence light irradiated from a low-coherence light source 101 is guided to a first optical fiber 106, and is branched into a third optical fiber 109 and a fourth optical fiber 110 by an optical coupler 108 having four input/output. Visible laser light emitted from an aiming beam laser 103 is multiplexed at the third optical fiber 109 by an optical coupler 112. The third optical fiber 109 is connected to a fifth optical fiber 113 by an optical connector 104, and transmits low-coherence light to the optical scanning probe 105.

Figure 20:
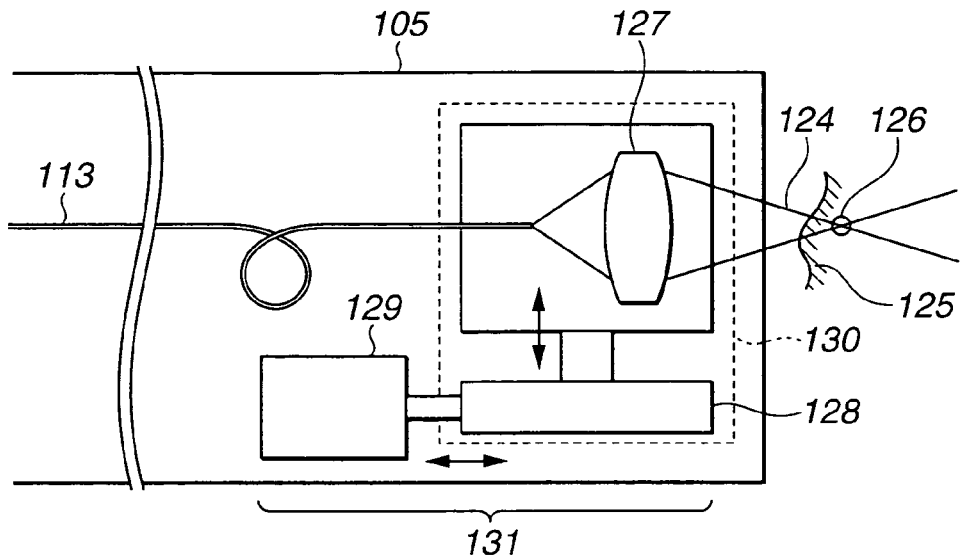
FIG. 20 is a diagram illustrating a schematic configuration of the tip of the optical scanning probe.

The configuration of the tip portion of the optical scanning probe 105 is shown in FIG. 20. Low-coherence light emitted from the fifth optical fiber 113 end portion is focused at an observation point 126 within the object of observation 125 as observation light (observation beam) 124 by a condenser lens 127. An object unit 130 made up of the fifth optical fiber 113 end portion and the condenser lens 127 has optical scanning means 128, and scans the object of observation 125 which is the subject while moving the observation light 124 and the observation point 126 two-dimensionally. Also, the object unit 130 is connected to depth-wise direction scanning means 129 serving as focal point moving means, and can scan the observation point 126 in the depth-wise direction of the object of observation. The optical scanning means 128 and the depth-wise direction scanning means 129 are driven by scanning driving means 122 shown in FIG. 19. That is to say, the focal point moving means move the condenser lens 127 and the depth-wise direction scanning means 129 integrally in the optical axis direction.

The optical scanning probe 105 has a slender and flexible tube shape, and accordingly can be readily inserted in a body cavity directly or by endoscope, or by blood vessel. This can also be configured as an endoscope itself having an observation optical system.

The fourth optical fiber 110 is connected to a frequency shifter 111, and the output of the frequency shifter 111 is introduced to a sixth optical fiber 114. Examples of frequency shifters 111 which can be used are phase-modulation means including acousto-optical devices (AOM), electro-optical device (EO), piezoelectric devices provide with fiber loops, and so forth.

The light emitted from the edge of the sixth optical fiber 114 passes through a collimator lens 115 and is guided to a movable mirror 116. The movable mirror 116 can be moved in the optical axis direction of the emitted light by mirror driving means 117. The edge of the sixth optical fiber 114, the collimator lens 115, movable mirror 116, and the mirror driving means 117, make up optical path length adjusting means 118.

The second optical fiber 107, which is the remaining terminal of the optical coupler 108 is connected to an optical detector 102. Preferably single mode fiber, low-order multimode fiber capable of sufficiently maintaining coherence, polarization-maintaining fiber, and so forth, can be used for the first optical fiber 106, the second optical fiber 107, the third optical fiber 109, the fourth optical fiber 110, the fifth optical fiber 113, and the sixth optical fiber 114.

The near-infrared low-coherence light emitted from the low-coherence light source 101 is guided to the first optical fiber 106, and is branched into the third optical fiber 109 and fourth optical fiber 110 by the optical coupler 108. The light guided to the third optical fiber 109 is guided to the optical scanning probe 105 by the optical connector 104 and the fifth optical fiber 113, and is emitted as observation light 124 to the object of observation 125.

Scanning by the observation light 124 and the observation point 126 is performed on the object of observation 125 by the optical scanning means 128 and the depth-wise direction scanning means 129. The reflected light or scattered light from the object of observation 125 at the observation point 126 returns to the fifth optical fiber 113 through the condenser lens 127, and returns to the third optical fiber 109, retracing the path. The path of this light is the body side 132.

In the same way, the low-coherence light branching to the fourth optical fiber 110 is subjected to frequency transition at the frequency shifter 111, and passes through the sixth optical fiber 114 and is emitted at the collimator lens 115, the light irradiated into the collimator lens 115 is converted into generally parallel light, and is guided to the movable mirror 116. The light reflected off at the movable mirror 116 is guided again to the sixth optical fiber 114 by the collimator lens 115, and returns to the fourth optical fiber 110. The path of this light is the reference side 133.

The two lights of the body side 132 and the reference side 133 are mixed by an optical coupler 108. In the event that the optical path length of the body side 132 and the optical path length of the reference side 133 accord within the range of coherence length of the low-coherence light source 101, interference light which has passed through the second optical fiber 107 and which fluctuations of frequencies equal to or double the amount of frequency transition at the frequency shifter 111, is detected by the optical detector 102. Now, information from the observation point 126 can be constantly obtained as interference light by adjusting the position of the moveable mirror 116 in the optical axis direction by the mirror driving means 117 of the optical path length adjusting means 118 so that the optical path length of the reference side 133 and the optical path length up to the observation point 126 of the body side accord.

The detected interference light is converted into electric signals by the optical detector 102. The electric signals are supplied to the demodulator 119. Extracting signals near frequencies of equal, double, or higher orders of the frequency transition at the frequency shifter 111, with the demodulator 119, enables signals from the observation point 126 to be detected with a higher S/N ratio by optical heterodyne detection. Scanning is performed by moving the observation point 126 of the observation light 124 generally perpendicularly and in the depth-wise direction, two-dimensionally by the scanning driving means 122. Synchronously with the control signals for the scanning, the demodulator 119 signals are acquired by a personal computer (hereafter abbreviated as PC) 121 corresponding to scan position signals of the observation point 126 from the scanning driving means 122, via an analog-digital (A/D) converter 120. Displaying the demodulated signals corresponding to the scan position signals of the observation point 126 by luminance on the display 123 of the PC 121 allows a two-dimensional tomographic image in the depth-wise direction of the object of observation 125 to be obtained.

Next, the optical scanning probe 105 will be described in detail with reference to FIG. 21 through FIG. 27.

Figure 21:
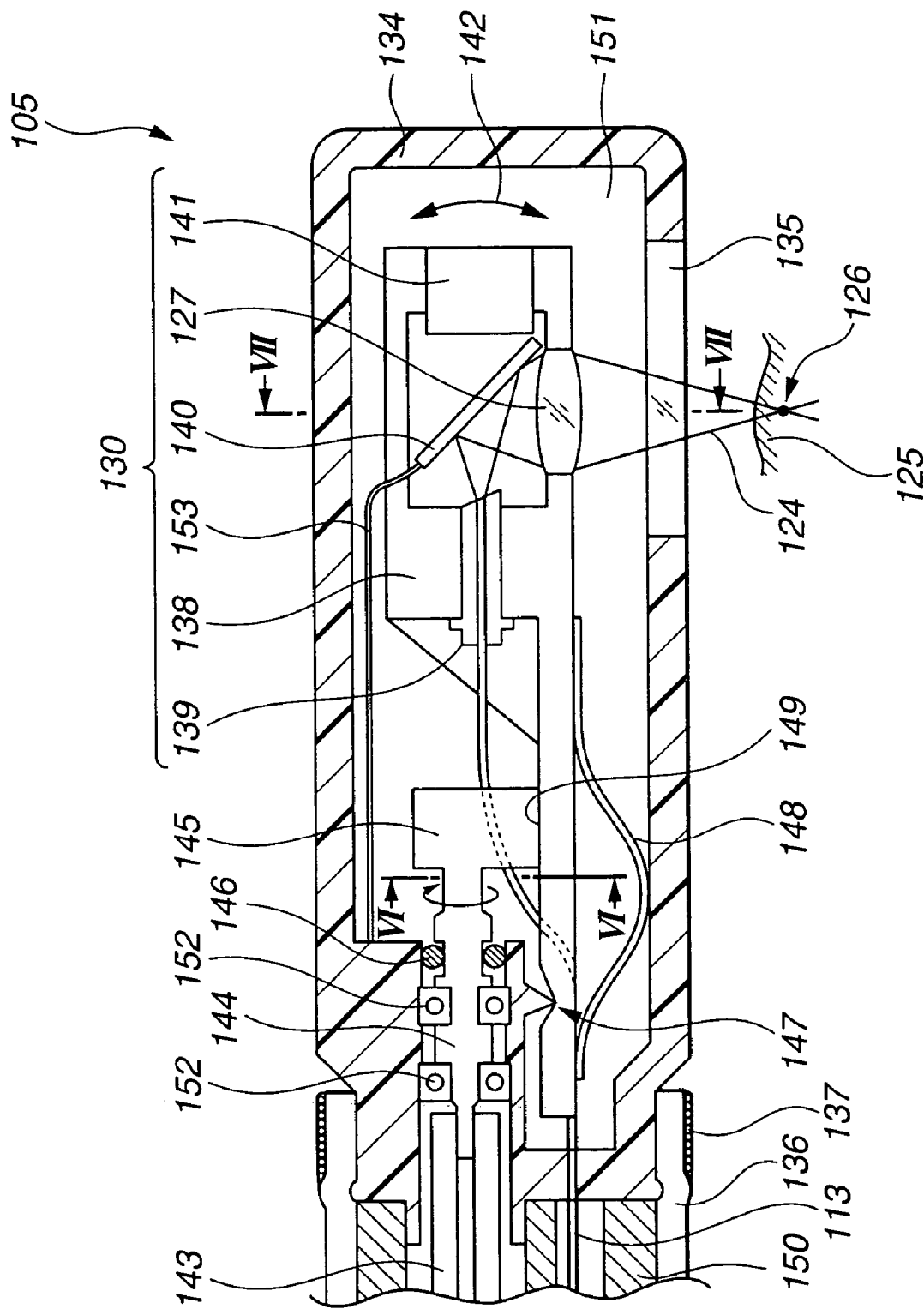
FIG. 21 is a cross-sectional diagram illustrating a detailed configuration of the tip portion of the optical scanning probe.

FIG. 21 is a cross-sectional diagram illustrating the configuration of the tip portion of the optical scanning probe 105. The object unit 130 described in FIG. 20 is configured of the condenser lens 127, fifth optical fiber 113 and a ferrule 139 for fixing the end thereof, a scanning mirror 140, a magnet 141, and a lens frame 138. The light emitted from the end of the fifth optical fiber 113 fixed by the ferrule 139 has the direction thereof changed by the scanning mirror 140, is converged by the condenser lens 127 so as to become observation light 24, and is converged at the observation point 126. The scanning mirror 140, magnet 141, and condenser lens 127 configure optical scanning means 128 shown in FIG. 20. The scanning mirror 140 is oscillated by a driving current via a driving cable 153, deflecting the observation light 124, so the observation point 126 moves, and the object of observation 125 can be scanned in a direction generally perpendicular to the optical axis shown in the drawing.

Figure 23:
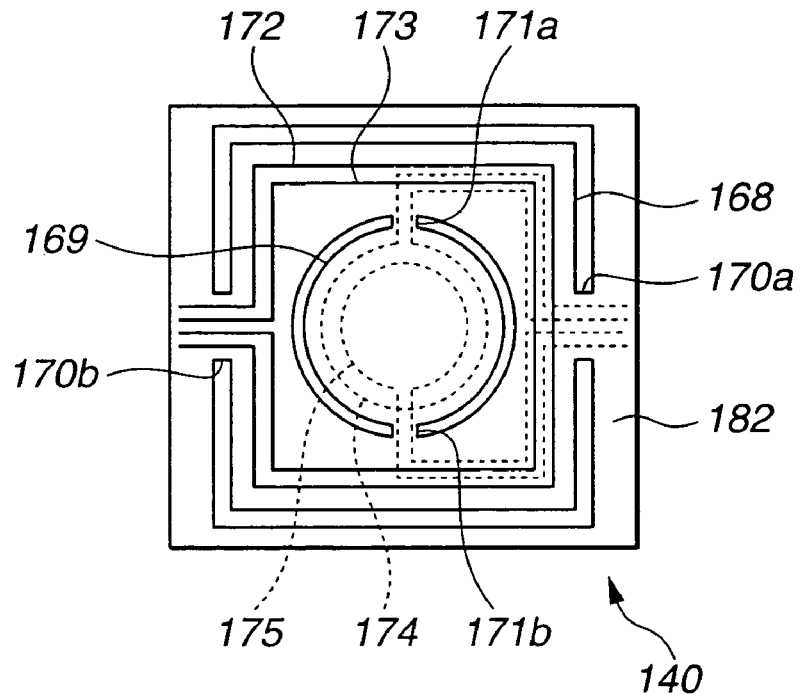
FIG. 23 is a diagram illustrating a detailed configuration of the scanning mirror.

FIG. 23 is a diagram for describing the detailed configuration of the scanning mirror 140. The scanning mirror 140 is preferably formed of silicon, and can be manufactured with the same process as manufacturing semiconductors. With the scanning mirror 140, an X-axial oscillating mirror 169 which actually reflects the light is resiliently held to a Y-axial oscillating plate 168 by intorelance portions 171a and 171b. The X-axial oscillating mirror 169 oscillates incident light so as to scan the Y-axial oscillating plate 168 in an X-axial direction. The surface of the X-axial oscillating mirror 169 is a reflecting face, and an X-axial driving coil 174 and an X-axial detecting coil 175 are provided on the rear side thereof, as indicated by dotted lines. Applying electricity to the X-axial driving coil 174 generates rotational force as to the magnetostatic field generated by the magnet 141, and the X-axial oscillating mirror 169 oscillates. Also, oscillating the X-axial detecting coil 175 as to the magnetostatic field generated by the magnet 141 generates electromotive force, and the speed of oscillation can be monitored by detecting the electromotive force.

In the same way, the Y-axial oscillating plate 168 is elastically held to a supporting frame 182 by intorelance portions 170a and 170b. A Y-axial driving coil 172 and a Y-axial detecting coil 173 are provided on the surface of the Y-axial oscillating plate 168. Applying electricity to the Y-axial driving coil 172 generates rotational force as to the magnetostatic field generated by the magnet 141, and the Y-axial oscillating plate 168 oscillates. Also, oscillating the Y-axial detecting coil 173 as to the magnetostatic field generated by the magnet 141 generates electromotive force, and the speed of oscillation can be monitored by detecting the electromotive force.

Accordingly, electricity is applied to the X-axial driving coil 174 and the Y-axial driving coil 172, and control is performed while monitoring the electromotive force generated by applying electricity with the X-axial detecting coil 175 and the Y-axial detecting coil 173, and the X-axial oscillating mirror 169 is oscillated in the two directions of freedom of X and Y, thereby deflecting the observation light 124 and the observation point 126, so the object of observation 125 can be scanned in the two-dimensional direction.

The tip of the optical scanning probe 105 is covered with a hard housing 134, with an observation window 135 formed of a transparent material such as glass disposed at the portion where the observation light 124 is transmitted. The housing 134 is connected to a resin sheath 136 formed of a pliable tube with a winder joint 137. The sheath 136 is a flexible outer cylinder provided over the entire length of the probe. Focal point moving means are configured by the object unit 130 being supported so as to oscillate on a pivot 147 serving as a fulcrum. A leaf spring 148 presses a lens frame 138 against a rotating cam 145 at a plane of contact 149, and also presses the housing 134 and lens frame 138 together at the pivot 147.

The rotating cam 145 is fixedly connected to a rotating shaft 144, and the rotating shaft 144 is rotably supported by a bearing 152 provided to the housing 134. The rotating cam 145 and the rotating shaft 144 make up a displacement conversion mechanism. The rotating shaft 144 is connected to a flexible shaft 143 serving as force transmitting means. The flexible shaft 143 is provided in the axial direction of the optical scanning probe 105. Accordingly, the rotations of the flexible shaft 143 are converted into movement on the depth-wise direction of the object of observation 125, and the object unit 130 moves.

Figure 24:
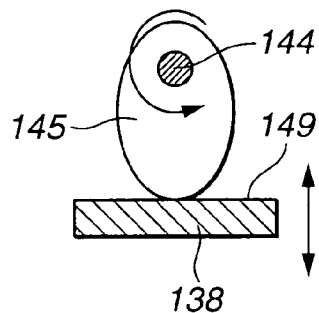
FIG. 24 is a cross-sectional diagram of a portion where a rotating cam and a lens frame are in contact with a contact face on the VI—VI cross-section in FIG. 21.

FIG. 24 is a cross-sectional view of the portion where the rotating cam 145 and the lens frame 138 are in contact at the plane of contact 149, as viewed from the direction of the arrow at the dotted line portion indicated by VI in FIG. 21. As shown in FIG. 24, the rotating cam 145 is eccentric as to rotating shaft 144. The lens frame 138 is pressed toward the rotating cam 145 side by the leaf spring 148, so upon the rotating shaft 144 rotating, the lens frame 138 oscillates vertically, i.e., in a direction generally orthogonal to the optical axis of the fifth optical fiber 113 by the rotating cam 145. The vertical motion at this time is magnified using the principle of leverage with the pivot 147 as the fulcrum, and the object unit 130 moves in the vertical direction indicated by the arrow 142. The observation point 126 also moves in the vertical direction, accordingly.

Combining the two-dimensional scanning as to the optical axis of the observation point 126 described above, and the vertical movement perpendicular to the two-dimensional plane, enables the object of observation to be scanned there-dimensionally. Consequently, a three-dimensional image can be obtained by obtaining information of reflected light or scattered light by the observation point from the low-coherence interference corresponding to the scanning. Of course, an arrangement may be made wherein the driving of the scanning mirror 140 is restricted to one-dimensional direction, and scanning the one-dimensional direction and the two directions of the vertical direction allows a two-dimensional tomographic image to be obtained.

Also, a refractive index rectifying fluid 151 which has generally the same refractive index as that of the body is sealed into the housing 134. In order to prevent liquid leakage of the scanning mirror 140, the lens frame 138, the ferrule 139, the magnet 141, the driving cable 153, and the condenser lens 127 are sealed by adhesion, so as to be watertight. Also, a watertight seal of an o-ring 146 is provided to the rotating shaft 144, and the refractive index rectifying fluid 151 is thus sealed into the housing 134.

Figure 25:
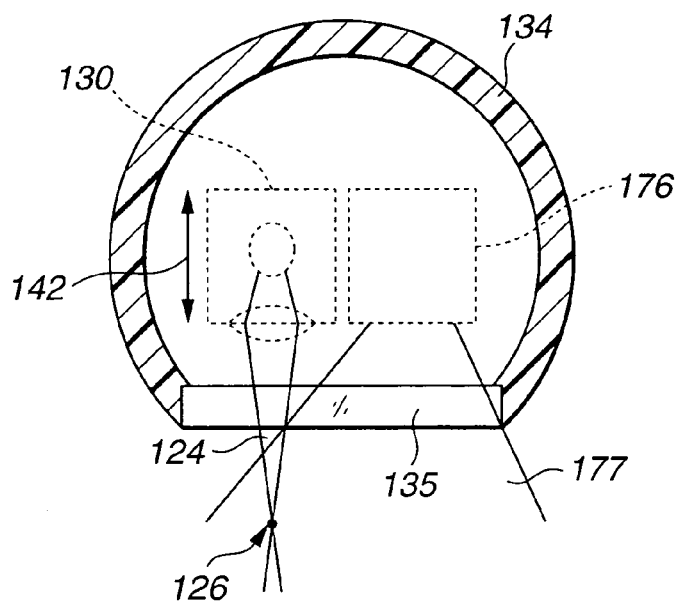
FIG. 25 is a cross-sectional diagram including the observation point of the optical scanning probe on the VII—VII cross-section in FIG. 21.

FIG. 25 is a cross-sectional diagram including the observation point 126 of the optical scanning probe 105 as viewed from the direction of the arrow at the dotted line portion indicated by VII in FIG. 21. An image pick-up unit 176 is provided generally parallel to the object unit 130.

Figure 26:
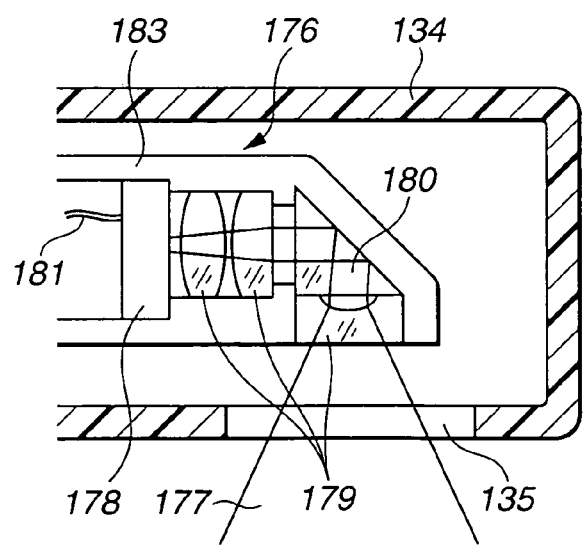
FIG. 26 is a cross-sectional diagram of an image pick-up unit.

FIG. 26 is a cross-sectional diagram of an image pick-up unit 176. The image pick-up unit 176 is configured of a lens group 179, prism 180, CCD 178, CCD signal cable 181, and image pick-up unit frame 183. The light within the observation range 177 is imaged on the CCD 178 by the lens group 179 and prism 180, so the field view range of the observation range 177 is observed. As shown in FIG. 25, the object unit 130 and image pick-up unit 176 are provided so that the observation point 126 is included in the observation range 177 of the image pick-up unit 176, and the field view range of the observation light 124 and the image pick-up unit 176 is included in the range of the shared observation window 135. In other words, the shared observation window 135 is used for light within the field view range of the observation light 124 and the image pick-up unit 176. In this case, as shown in FIG. 19, an aiming beam which is visible light is introduced for the observation light 124, so the endoscope field of view and the position of the optical tomographic image observation range can be understood in a correlated manner. That is to say, the optical scanning range by the optical scanning means is contained in the observation range by the image pick-up means of the endoscope. Also, the CCD 178 has sensitivity regarding near-infrared light outside of the visible light range as well, so a non-visible light aiming beam may be used for the aiming beam instead. Further, a low-coherence light source with a wavelength in the sensitivity range of the CCD 178 allows the optical tomographic image observation range to be confirmed without using the aiming beam laser 103.

Figure 27:
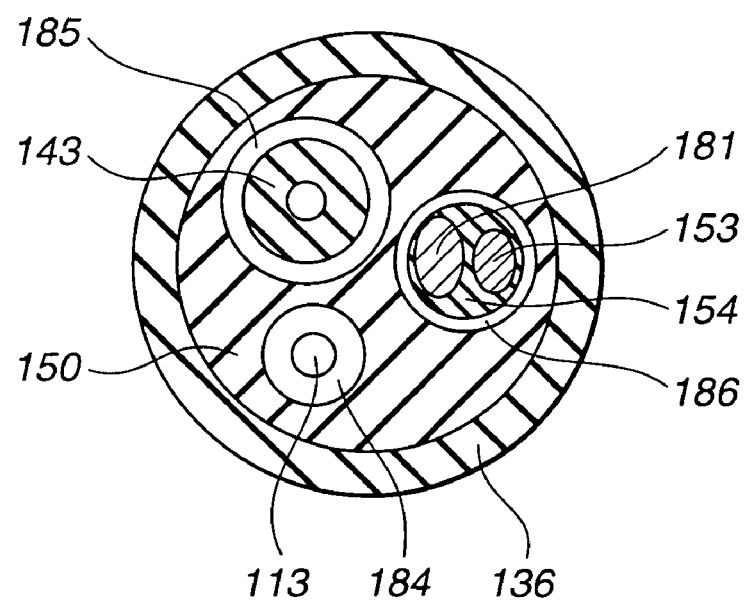
FIG. 27 is a cross-sectional diagram of a sheath portion of the optical scanning probe.

FIG. 27 is a cross-sectional diagram of the sheath 136 of the optical scanning probe 105. The interior of the sheath 136 is provided with a multi-lumen tube 150 with generally the same diameter as the hollow space within the sheath. The multi-lumen tube 150 has three through holes. The fifth optical fiber 113 is inserted through the first through hole 184. The flexible shaft 143 is inserted through the second through hole 185. A signal cable 154 bundling the CCD signal cable 181 and the scanning mirror driving cable 153 is inserted through the third through hole 186. Using the multi-lumen tube 150 is advantageous since ease of assembly improves, and installation density improves. Also, multiple single tubes may be used instead of the multi-lumen tube 150.

Figure 22:
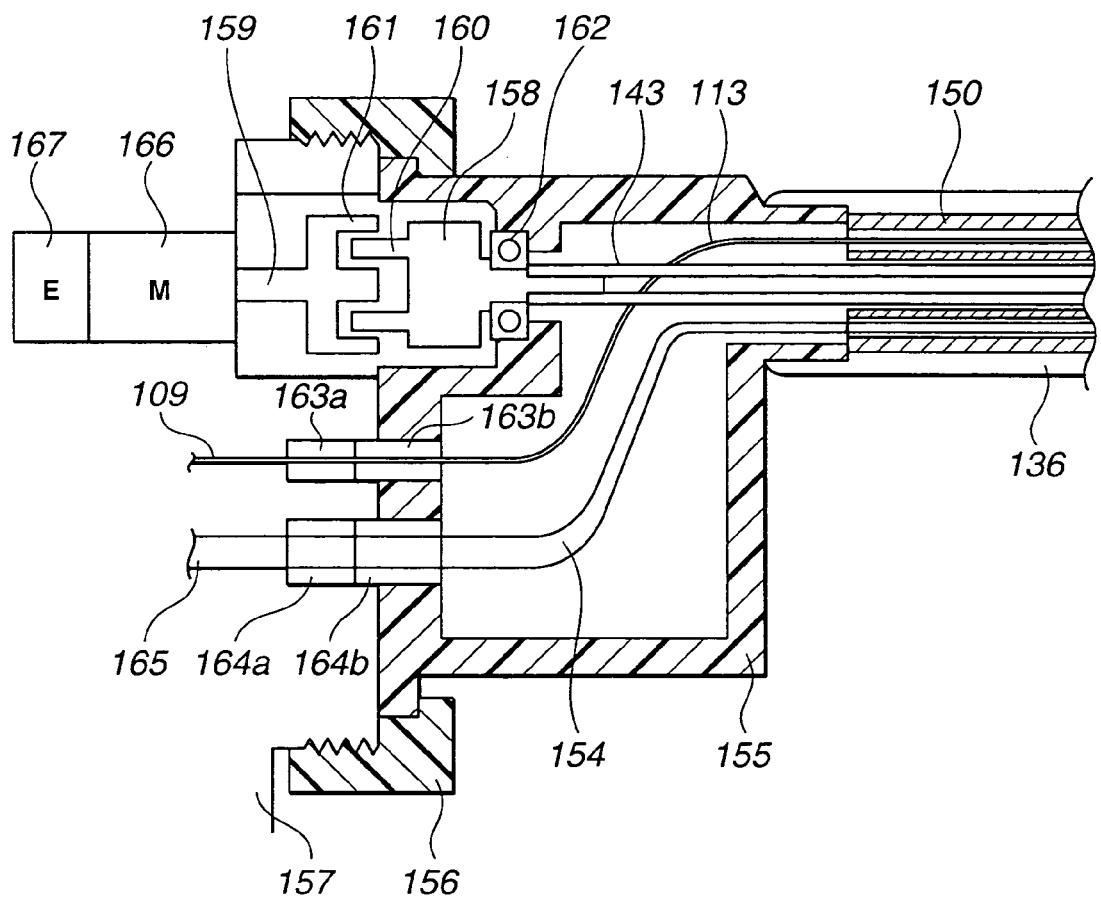
FIG. 22 is a cross-sectional diagram illustrating a configuration of the base portion of the optical scanning probe.

FIG. 22 is a cross-sectional diagram of the base end portion of the optical scanning probe 105. The sheath 136 and the multi-lumen tube 150 are connected to a connector housing 155. The connector housing 155 is detachably connected to observation apparatus housing 157 by an attaching member 156 having an attaching screw portion. A rotation transmission receiver 158 is rotably provided to the connector housing 155 by a bearing 162, and the shaft of the rotation transmission receiver 158 is connected to the flexible shaft 143. The observation apparatus housing 157 has a motor 166 and an encoder 167 for detecting the rotational angle of the motor and the speed thereof, and a rotation transmission shaft 159 is connected to the shaft of the motor 166. A pin receptacle 161 is provided to the rotation transmission shaft 159, and pins 160 are provided on the rotation transmission receiver 158. The rotations of the motor 0.166 are transmitted to the rotation transmission shaft 159, to the pin receptacle 161, to the pins 160, to the rotation transmission receiver 158, and then to the flexible shaft 143. As a result, as described above, the object unit 130 moves vertically by the rotations transmitted to the flexible shaft 143, and the observation point 126 moves in the depth-wise direction of the object of observation 125, whereby depth-wise direction scanning is performed. Also, optical connectors 163a and 163b are provided to the connector housing 155 and the observation apparatus housing 157, for connecting the fifth optical fiber 113 and the third optical fiber 109. Also, electric connectors 164a and 164b for connecting a cable 165 and the signal cable 154 are provided.

Also, the optical scanning probe 105 also serves as an endoscope, and has an unshown treatment instrument insertion channel, air supply and water supply mechanism for cleaning the observation window 135, a bending mechanism, and so forth the same as with an ordinary endoscope.

Figure 28:
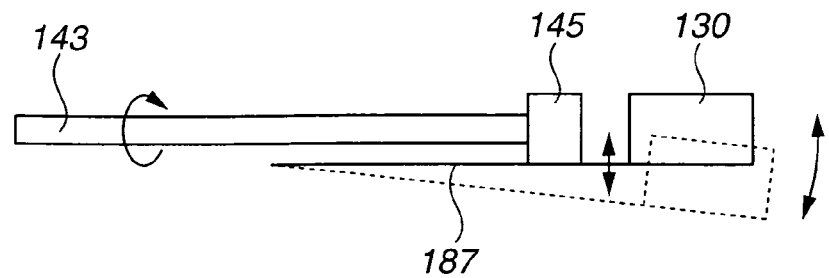
FIG. 28 is a diagram for describing a separate configuration example of the depth-wise direction scanning means.

FIG. 28 is a diagram for describing a separate configuration example of the depth-wise direction scanning means 29. In FIG. 28, the points different from FIG. 21 will be described, and accordingly, only the different points are shown. An object unit 130 is provided on a leaf spring 187 instead of the lens frame 138 and the leaf spring 148 shown in FIG. 21. Other than that, the rotating cam 145 is rotated by the flexible shaft 143 and the object unit 130 is moved vertically as to the drawing in FIG. 28, i.e., in a direction perpendicular to the flexible shaft 143, thereby performing depth-wise direction scanning, the same as with FIG. 21.

Figure 29:
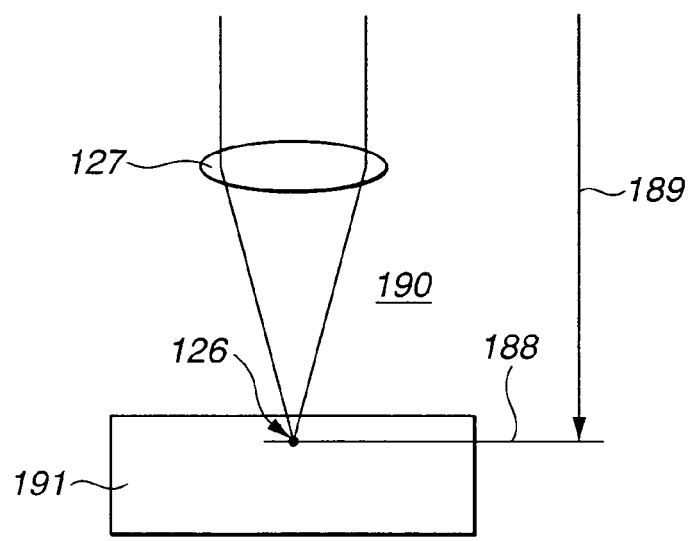
FIG. 29 is a diagram for describing the relation between the interference position from low-coherence interference and the converging position.
Figure 30:
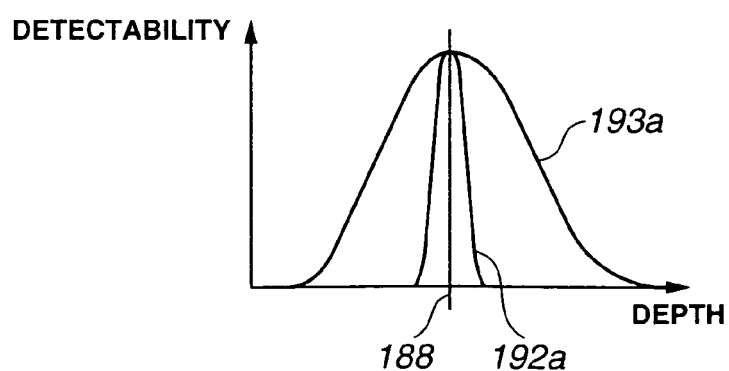
FIG. 30 is a diagram for describing the relation between the depth and detectability from low-coherence interference.

FIG. 29 through FIG. 34 are drawings for describing the relation between the interference position due to low-coherence interference, and the converging position. For example, as shown in FIG. 29, let us say that the condenser lens 127 is provided in the atmosphere 190 (refractive index n=1), and is observing near the surface of the body tissue 91 (refractive index n=nt). At this time, the observation point 126 which is the converging point of the condenser lens 127 accords the interference position 188 by the low-coherence interference stipulated by the optical path length 189. Thus, information of the observation point 126 can be obtained with high resolution. The graph in FIG. 30 illustrates the relation between depth and detectability. In FIG. 30, the horizontal axis represents the depth, and the vertical axis represents the detectability. Reference numeral 192a represents the detection efficiency by low-coherence interference, and 193a represents the detection efficiency by the converging force of the condenser lens 127. The two multiplied yield the overall detection efficiency, so it can be understood that the detectability of the observation point 126 at the interference position 188 is high.

Figure 31:
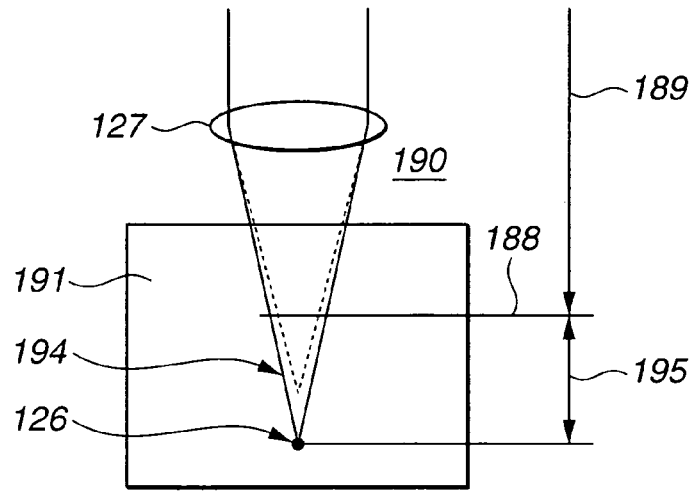
FIG. 31 is a diagram for describing the relation between the interference position from low-coherence interference and the converging position.

However, as shown in FIG. 31, in the event that the depth-wise direction scanning means 129 shown in FIG. 20 are used to scan the observation point 126 deep within the body tissue 191, the observation point 126 position is at a position deeper than the observation point position 194 in the atmosphere. With the scanning amount as Δdepth, this is a scanning amount deeper by (nt−1)×Δdepth.

On the other hand, with the scanning amount as Δdepth, the low-coherence interference position 188 is shallower by (1−1/nt)×Δdepth as to the observation point position 194 in the atmosphere.

Accordingly, there is the difference 195 between the depth-wise position of the observation point 126 and the low-coherence interference position 188. This difference is (nt−1)×Δdepth+(1−1/nt)×Δdepth.

Figure 32:
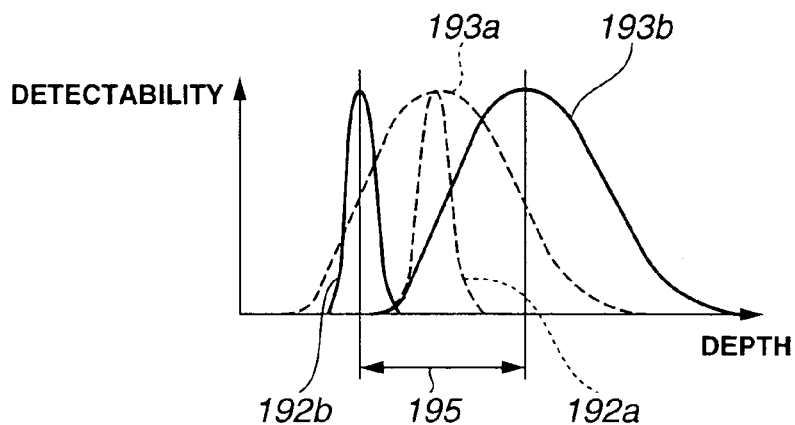
FIG. 32 is a diagram for describing the relation between the depth and detectability from low-coherence interference.

FIG. 32 is a diagram for describing this difference. The curve of the low-coherence interference detection efficiency 192a moves toward the shallow side as indicated by 192b, and the curve of the converging force detection efficiency 193a moves toward the deep side as indicated by 193b. Here, multiplying the low-coherence interference detection efficiency 192b and the converging force detection efficiency 193b yield the overall detection efficiency, so it can be understood that the overall system has low detection efficiency, and that depth-wise direction information cannot be obtained.

Figure 33:
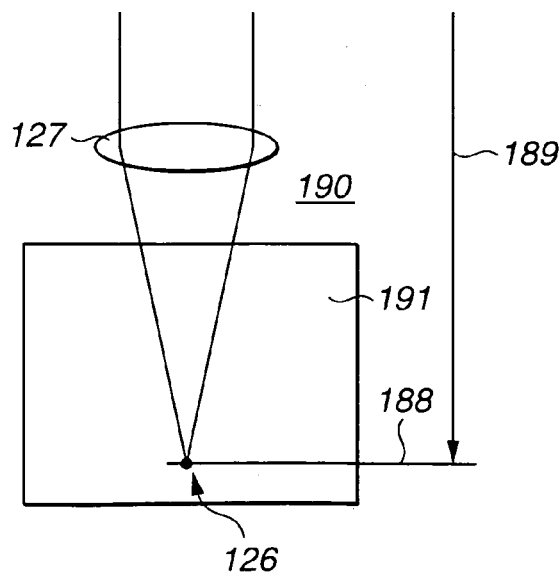
FIG. 33 is a diagram for describing the relation between the interference position from low-coherence interference and the converging position.
Figure 34:
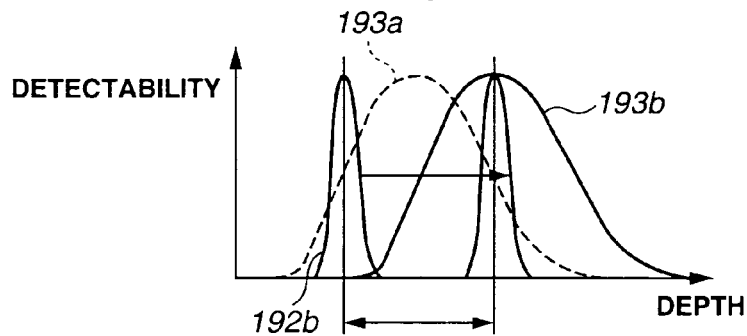
FIG. 34 is a diagram for describing the relation between the depth and detectability from low-coherence interference.

Accordingly, as shown in FIG. 33, the optical path length adjusting means 118 shown in FIG. 19 are used to increase the optical path length by the difference 195, so as to move the curve of the low-coherence interference detection efficiency 192b in the deep direction as indicated by 192c, thereby according the depth position of the observation point 126 with the low-coherence interference position 188. Accordingly, the information of the observation point 126 can be obtained with high detection efficiency. In the event of observing a predetermined range of within the body, inside of the body can be observed with high efficiency and with high horizontal resolution, by adjusting the optical path length using the optical path length adjusting means 118 so as to obtain high detection efficiency with regard to a certain depth in the body.

Figure 35:
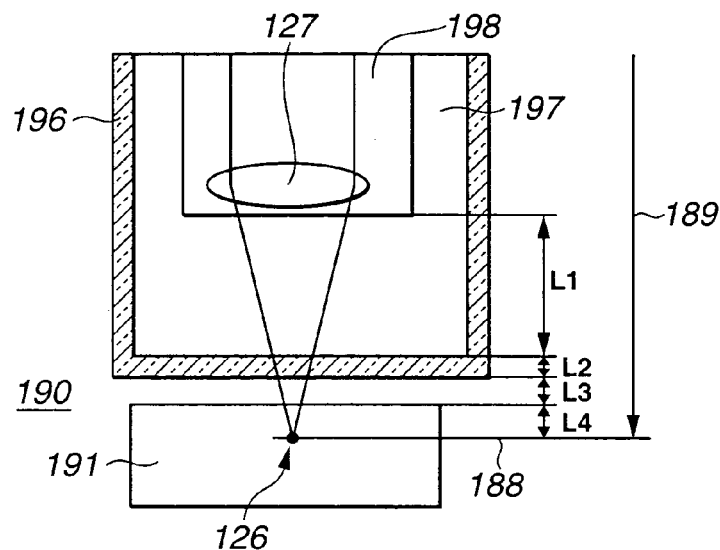
FIG. 35 is a diagram for describing a method for according the position of the observation point and the low-coherence interference position.
Figure 36:
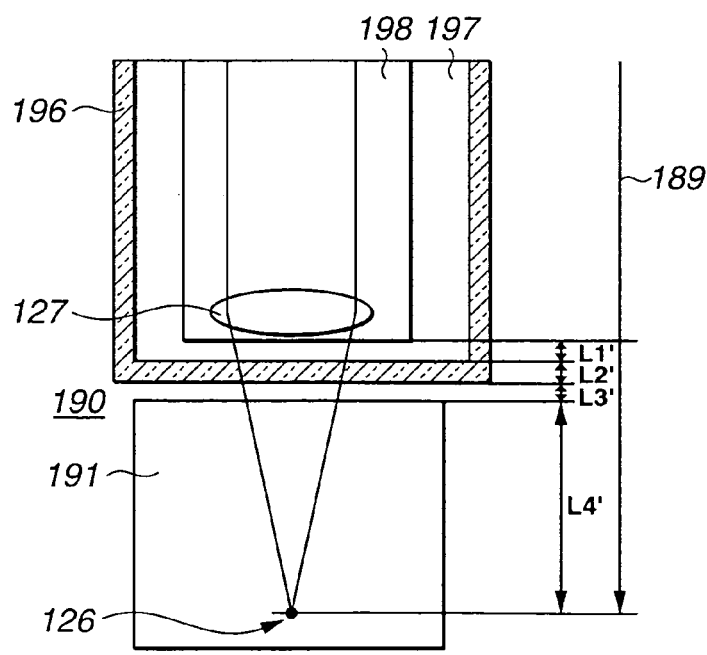
FIG. 36 is a diagram for describing another method for according the position of the observation point and the low-coherence interference position.

FIG. 35 and FIG. 36 are diagrams for describing another method for according the depth position of the observation point 126 with the low-coherence interference position 188.

The inside of the housing 196 configured of a transparent material with a reflective index of ns is filled with a refractive index rectifying fluid 197 having generally the same refractive index as the refractive index nt of the body. A watertight housing 198 and a condenser lens 127 are provided within the refractive index rectifying fluid 197.

Now, the optical path length from the tip of the watertight housing 198 to the observation point 126 is as follows.

Optical path length 1=($ntL1+nsL2+L3+ntL4=nt(L1+L4)+nsL2+L3$)

Here, in the event of scanning the condenser lens 127 and the watertight housing 198 using the depth-wise direction scanning means 129 such as shown in FIG. 20 by a scanning amount Δdepth in the depth-wise direction, $L1'=L1-\Delta depth$ $L4'=L4+\Delta depth$ hold, as shown in FIG. 36, so Optical path length 2=($ntL1'+nsL2+L3+ntL4'$) =$nt$ ($L1-\Delta depth+L4+\Delta depth$)+$nsL2+L3=nt(L1+L4)+nsL+L3$=Optical path length 1, so there is no change in the optical path length.

Also, the distance passing through the respective refractive indexes (nt, ns, 1) is the same following scanning as well, so the observation point 126 also moves by Δdepth. Accordingly, the depth position of the observation point 126 and the low-coherence interference position 188 accord over the entire scanning area in the depth-wise direction, thereby enabling high detection efficiency and high horizontal resolution to be maintained.

Also, providing a reflection preventing film serving as a refractive index rectifying layer (such as to prevent reflection with regard to the reflective index of the subject), on the surface (interface) of the observation window 135 toward the subject in FIG. 21, prevents Fresnel reflection occurring due to the difference between the refractive index of the material of the observation window and the refractive index of the subject, thereby reducing noise light, and improving the S/N ratio. The same thing can be provided at the contact face (interface) between the observation window 135 and the condenser lens 127 with the refractive index rectifying fluid 151.

As described above, according to the present embodiment, the focal point moving means are driven by flexible motive force transmitting means provided on the axial direction of the optical probe, so an optical scanning probe device having short dimensions for the top hard portion, and having a precisely-controllable focal point variation mechanism, can be realized.

Also, using a displacement conversion mechanism wherein the amount of force transmitted to the motive force transmitting means and the displacement are in a unique relation allows the amount of movement of the focal position to be controlled by the amount of force instead of displacement, and control is facilitated in cases wherein the displacement changes due to bending of the probe, and so forth, as well.

Further, refractive index rectifying means having a transparent and pliable refractive index rectifying substance with generally the same refractive index as the subject between the converging means and the subject, capable of changing the distance between the converging means and the subject is provided, so reflection from the interface can be suppressed, thereby improving the S/N ratio.

Sixth Embodiment

Figure 37:
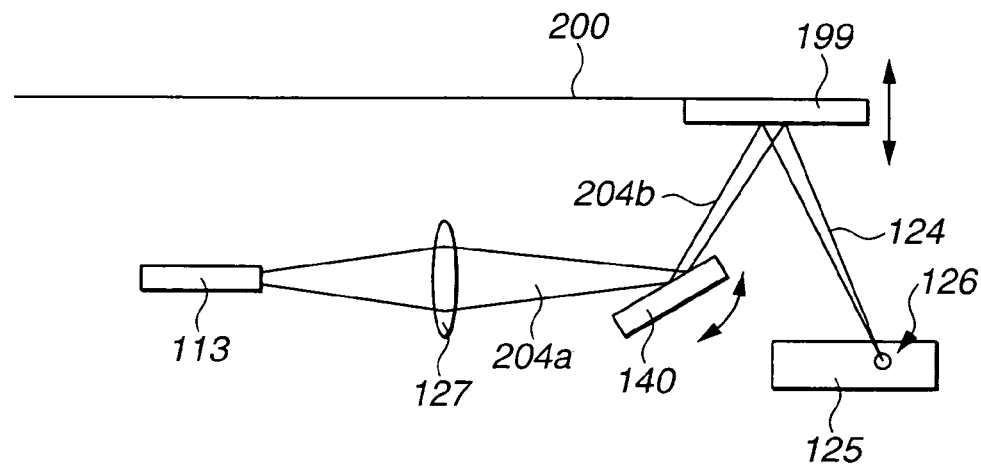
FIG. 37 is a diagram for describing the configuration of depth-wise direction scanning means in the sixth embodiment.

FIG. 37 illustrates a sixth embodiment. Only the portions different from the fifth embodiment will be described with reference to the drawing, and other portions will be denoted with the same reference numerals as those in the fifth embodiment and description thereof will be omitted.

Light irradiated from the fifth optical fiber 113 is converged by the condenser lens 127. The ray 204*a* is scanned by the scanning mirror 140 shown in FIG. 23 so as to become light 204*b*, is reflected by a reflecting mirror 199 provided on a leaf spring 200 so as to become observation light 124, and is irradiated onto the body tissue 125. The leaf spring 200 is moved to scan vertically by a known actuator such as a mechanism using a flexible shaft 143 and rotating cam 145 the same as with FIG. 28, or an electromagnet for absorbing the unshown leaf spring 200 and a piezoelectric device provided on the leaf spring 200, or an actuator wherein the leaf spring is formed of a shape-memory alloy (SMA) and is bent by passing an electric current therein. Being moved so as to scan vertically scans the observation point 126 in the depth-wise direction. Two-dimensional or three-dimensional tomographic images can be obtained by scanning the observation point 126 in the horizontal direction and the depth-wise direction, using the optical scanning means 128 and the depth-wise direction scanning means 129 in FIG. 20.

Figure 38:
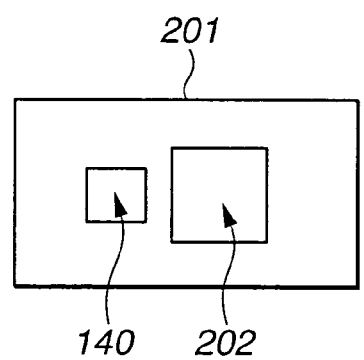
FIG. 38 is a diagram for describing the configuration of a scanning mirror unit for holding the scanning mirror.

Also, FIG. 38 illustrates a scanning mirror unit 201 for holding the scanning mirror 140. The scanning mirror unit 201 comprises a hole 202 near the scanning mirror 140 for passing observation light 124. The scanning mirror unit 201 is preferably manufactured at the same time as the scanning mirror 140 by semiconductor manufacturing process, and providing the hole 202 on the scanning mirror unit 201 allows the observation light 124 to be irradiated into the body tissue 125 close to perpendicular, so observation with even higher efficiency can be performed.

Figure 39:
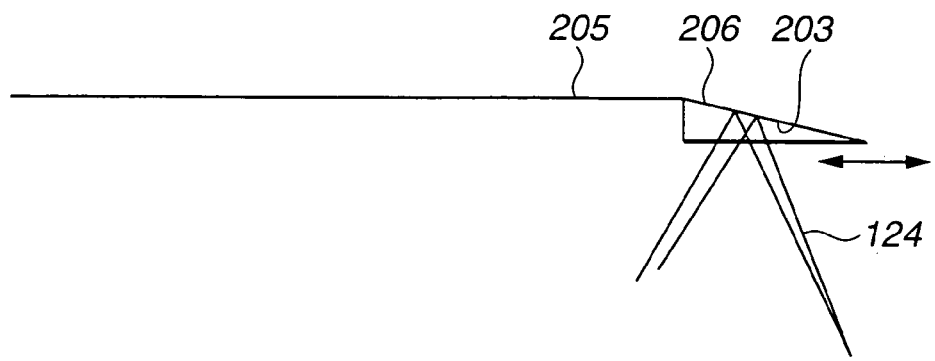
FIG. 39 is a diagram for describing the configuration of a wedge-shaped prism according to a modification of the sixth embodiment, with a reflecting face on the upper face thereof.

FIG. 39 illustrates a modification of the sixth embodiment. Instead of the reflecting mirror 199, a wedge-shaped prism 203 with a reflective face 206 provided on the upper face thereof is moved in the horizontal direction in the drawing by a rod 205, i.e., along the axial direction of the tube-shaped sheath 136, thereby enabling scanning in the depth-wise direction as to the body tissue 125 in the same way as vertically scanning the reflecting mirror 199 in FIG. 37. The wedge-shaped prism 203 has generally the same reflective index as the body tissue, serving to accord the observation point 126 and the interference position of the low-coherence interference over the entire scanning region in the depth-wise direction as with the refractive index rectifying fluid 197 in FIG. 35 and FIG. 36, yielding the advantages of maintaining high detection percentage and high resolution in the horizontal direction.

Seventh Embodiment

Figure 40:
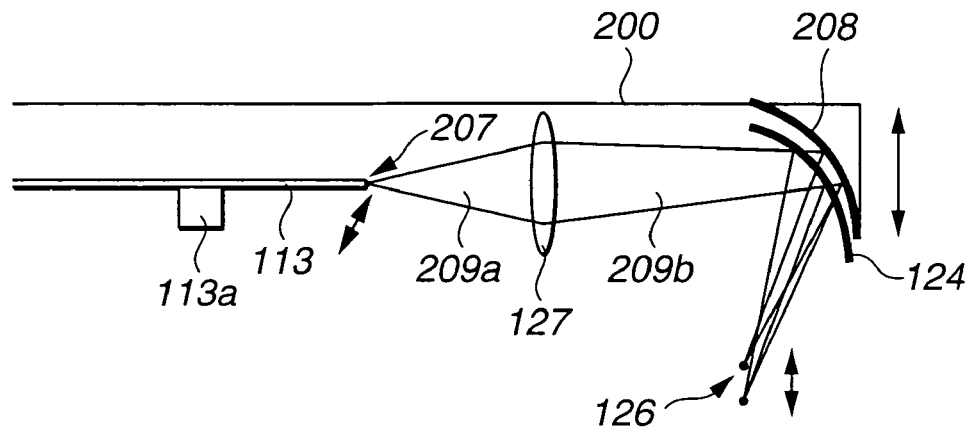
FIG. 40 is a diagram for describing the configuration of depth-wise direction scanning means in a seventh embodiment.

FIG. 40 shows a seventh embodiment. Only the portions different from the fifth embodiment will be described with reference to the drawing, and other portions will be denoted with the same reference numerals as those in the fifth embodiment and description thereof will be omitted.

Light irradiated from the fifth optical fiber 113 is changed into a light ray 209*b* by the condenser lens 127, becomes observation light 124 by the curved mirror 208 provided on an edge of the leaf spring 200, and is converged at the observation point 126 of the subject. The emitting end 207 of the fifth optical fiber 113 is vibrated in a vertical direction as to the drawing by a piezoelectric device 113*a* provided several millimeters toward the base side from the end portion of the fifth optical fiber 113. Accordingly, the angle of the light ray 209*a* entering the condenser lens 127 is changed, and the light ray 209*b* is scanned in the vertical direction in the drawing. The curved mirror 208 is provided between the condenser lens 127 and the subject. The curved mirror 208 which is a movable mirror is vertically driven by an unshown actuator illustrated in the sixth embodiment, and the observation point 126 is scanned in a direction perpendicular to the axial direction of the optical scanning probe 105 in an approximation manner. Movement of the curved mirror 208 moves the focal position in a generally-linear manner. Accordingly, a tomographic image can be obtained by scanning in the horizontal direction by the piezoelectric device 113*a* and in the observation depth-wise direction by the curved mirror 208.

Figure 41:
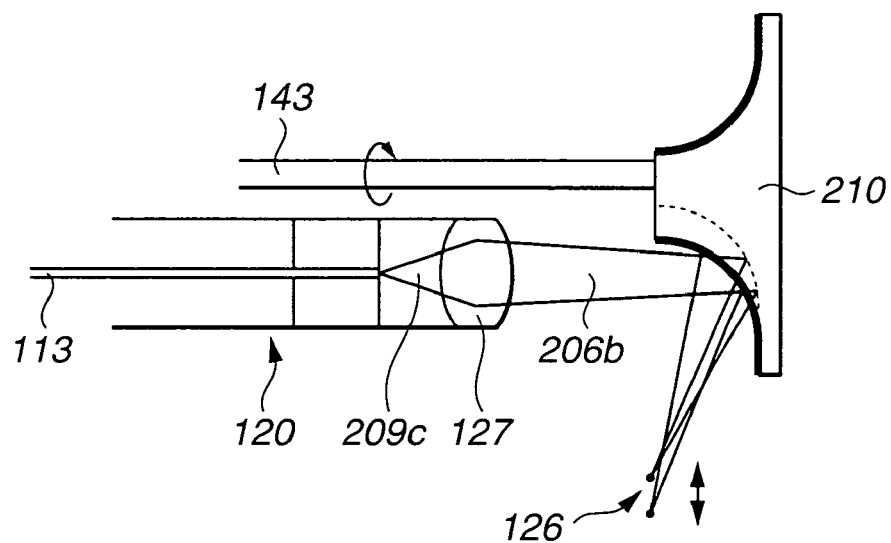
FIG. 41 is a diagram for describing the configuration of depth-wise direction scanning means in a modification of the seventh embodiment.
Figure 42:
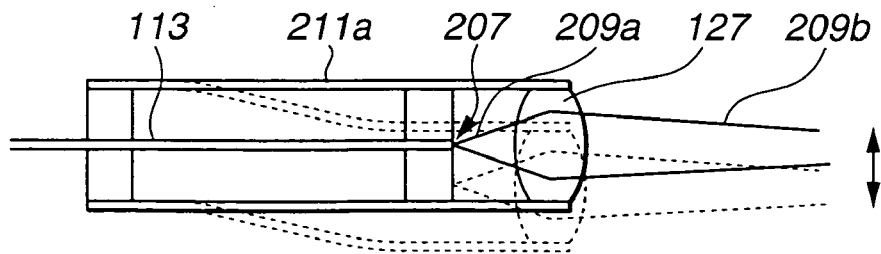
FIG. 42 is a cross-sectional diagram of optical scanning means shown in FIG. 41.

FIG. 41 and FIG. 42 illustrate a modification of the seventh embodiment. A curved rotating mirror 210 is provided instead of the curved mirror 208, and the curved rotating mirror 210 includes an eccentric shaft driven by the flexible shaft 143. FIG. 42 is a cross-sectional view of the optical scanning means 120 shown in FIG. 41. Light irradiated from the emitting end 207 of the fifth optical fiber 113 is emitted as a light ray 209*b* from the condenser lens 127. The condenser lens 127 and the emitting end 207 of the fifth optical fiber 113 are vertically scanned by bimorph piezoelectric device 211a and 211b, so the ray 209b is also scanned vertically (vertical to the drawing in FIG. 41). The curved rotating mirror 210 serving as the depth-wise scanning means is rotated by driving of the flexible shaft 143, and can scan the observation point 126 vertically, i.e., in a direction perpendicular to the axial direction of the optical scanning probe 105, in the same way as vertically scanning the curved mirror 208 which is a movable mirror.

A movable mirror provided between the converging means and the subject is used for the focal point moving means, so high-speed focal position changing can be realized.

Eighth Embodiment

Figure 43:
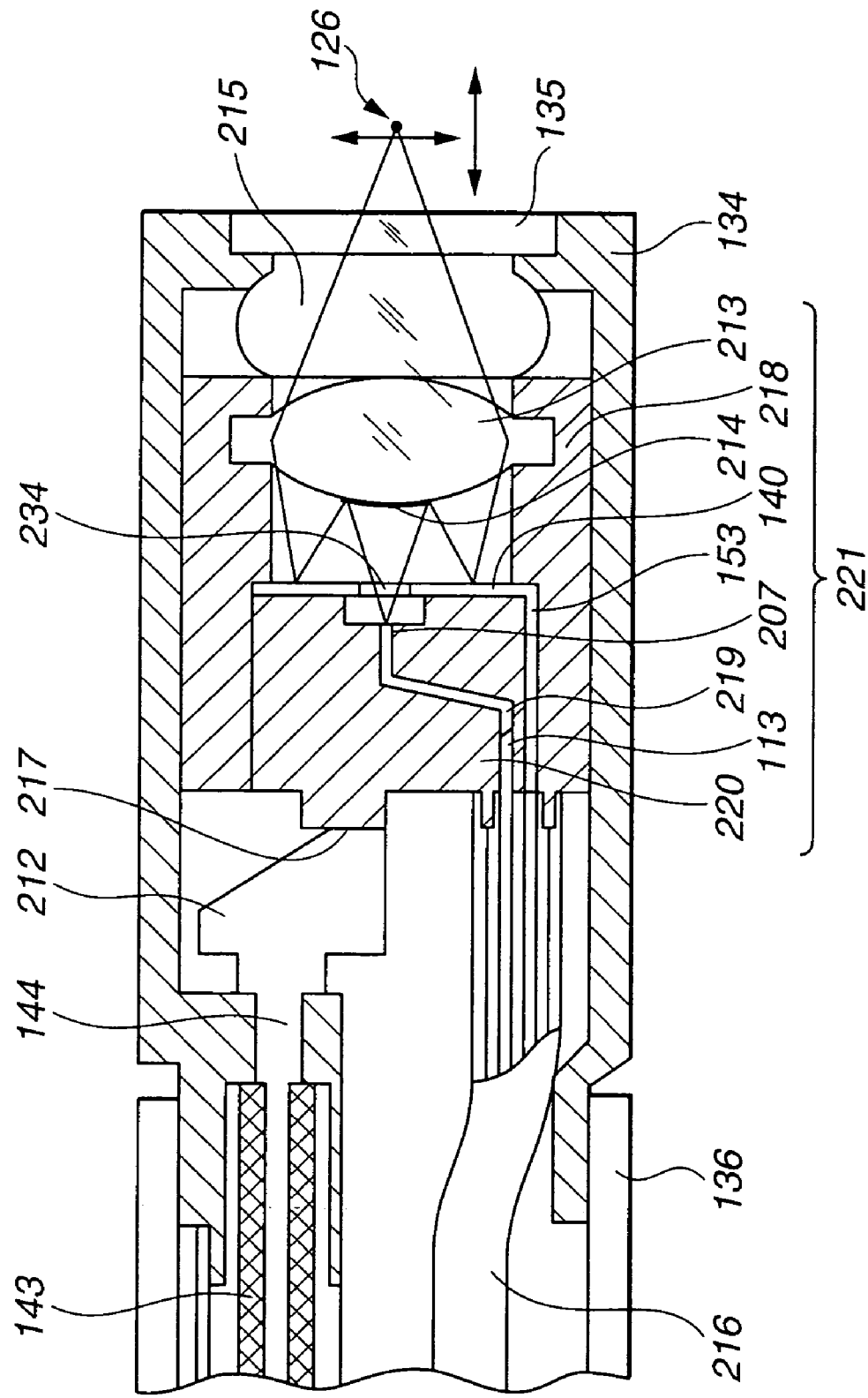
FIG. 43 is a cross-sectional diagram illustrating the configuration of the tip portion of the optical scanning probe according to an eighth embodiment.

FIG. 43 illustrates an eighth embodiment. Only the portions different from the fifth embodiment will be described with reference to the drawing, and other portions will be denoted with the same reference numerals as those in the fifth embodiment and description thereof will be omitted.

A light scanning unit 221 comprises a lens frame 218, a condenser lens 213, a light guide path base member 220, and a scanning mirror 140. Light transmitted through the fifth optical fiber 113 passes through a light guide path 219 and is emitted from an emitting end 207, passes through a hole 234 provided on the center of the scanning mirror 140 and is reflected off of a reflecting mirror 214 provided on the condenser lens 213, and is guided to the scanning mirror 140. The scanning mirror 140 may be an electromagnetic type as shown in FIG. 23 with the fifth embodiment, or may be an electrostatic type disclosed in Japanese Unexamined Patent Application Publication No. 11-84250.

The light which has changed directions by the scanning mirror 140 is converged at the observation point 126 by the condenser lens 213. The observation point is scanned in the general vertical direction as to the optical axis due to the oscillations of the scanning mirror 140. The light scanning unit 221 is movable in the optical axis direction of the condenser lens 213 within the housing 134, and is in contact with the rotating cam 212 by a protrusion 217 provided on the light guide path base member 220. The rotations of the flexible shaft 143 are transmitted to the rotating cam 212 by the rotating shaft 144. A transparent elastic member 215 is a sac of resin filled with a refractive index rectifying fluid, and is provided between the observation window 135 which is a transparent plate provide to the subject side, and the condenser lens 213. The light scanning unit 221 is pressed by the transparent elastic member 215 which is formed of transparent rubber or gel or the like, with the protrusion 217 being pressed toward the right side by the rotations of the rotating cam 212, so the light scanning unit 221 moves to the left and right directions in the drawing, and the observation point 216 is scanned in the left and right according to the rotations of the flexible shaft 143, i.e., in the depth-wise direction of the object of observation. Also, the fifth optical fiber 113 and the driving cable 153 are configured a single cable 216. The transparent elastic member 215 has generally the same reflective index as the body tissue, so the observation point 126 and the low-coherence interference position 188 accord over the entire scanning region in the depth-wise direction, so high detection efficiency and high resolution in the horizontal direction can be maintained.

Figure 44:
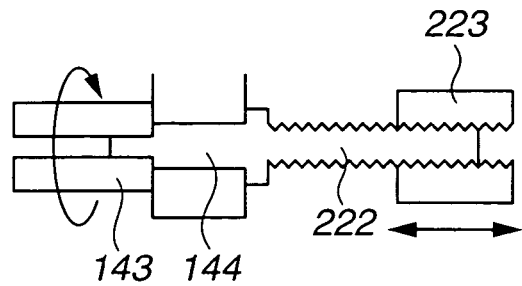
FIG. 44 is a diagram illustrating a modification of the depth-wise direction scanning means.
Figure 45:
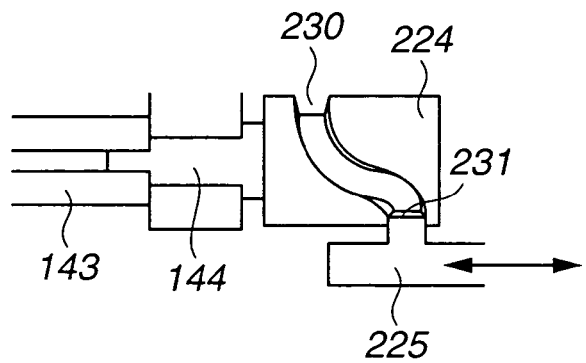
FIG. 45 is a diagram illustrating another modification of the depth-wise direction scanning means.
Figure 46:
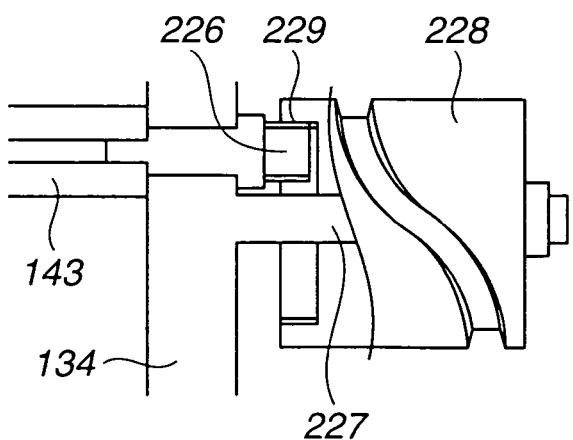
FIG. 46 is a diagram illustrating yet another modification of the depth-wise direction scanning means.

FIG. 44 through FIG. 46 illustrate modifications of the depth-wise direction scanning means in the eighth embodiment.

In FIG. 44, the rotations of the flexible shaft 143 are transmitted to a male screw 222 via the rotating shaft 144. A female screw 223 fixed to the light scanning unit 221 shown in FIG. 43 can be moved to the left and right, i.e., in the depth direction. In the case of this embodiment, there is the feature that driving can be performed even in the event that there is a great load as to the rotating force of the flexible shaft. With FIG. 45, a rotating cam 224 rotates by the flexible shaft 143, and a rod 225 can be moved to the left and right, i.e., in the depth direction, by a protrusion 231 on the rod 225 fixed onto the light scanning unit 221 moving over a cam groove 230 provided on the rotating cam 224. FIG. 46 is configured of a gear 226 rotating being linked to the flexible shaft 143 and a rotating cam 228 provided rotably to a shaft 227 provided on the housing 134, instead of the rotating cam 224 shown in FIG. 45, wherein reduction is performed at a rotating gear unit 229 of the flexible shaft 134 and is transmitted to the rotating cam 228, hereby obtaining a greater driving force than with FIG. 45.

Ninth Embodiment

Figure 47:
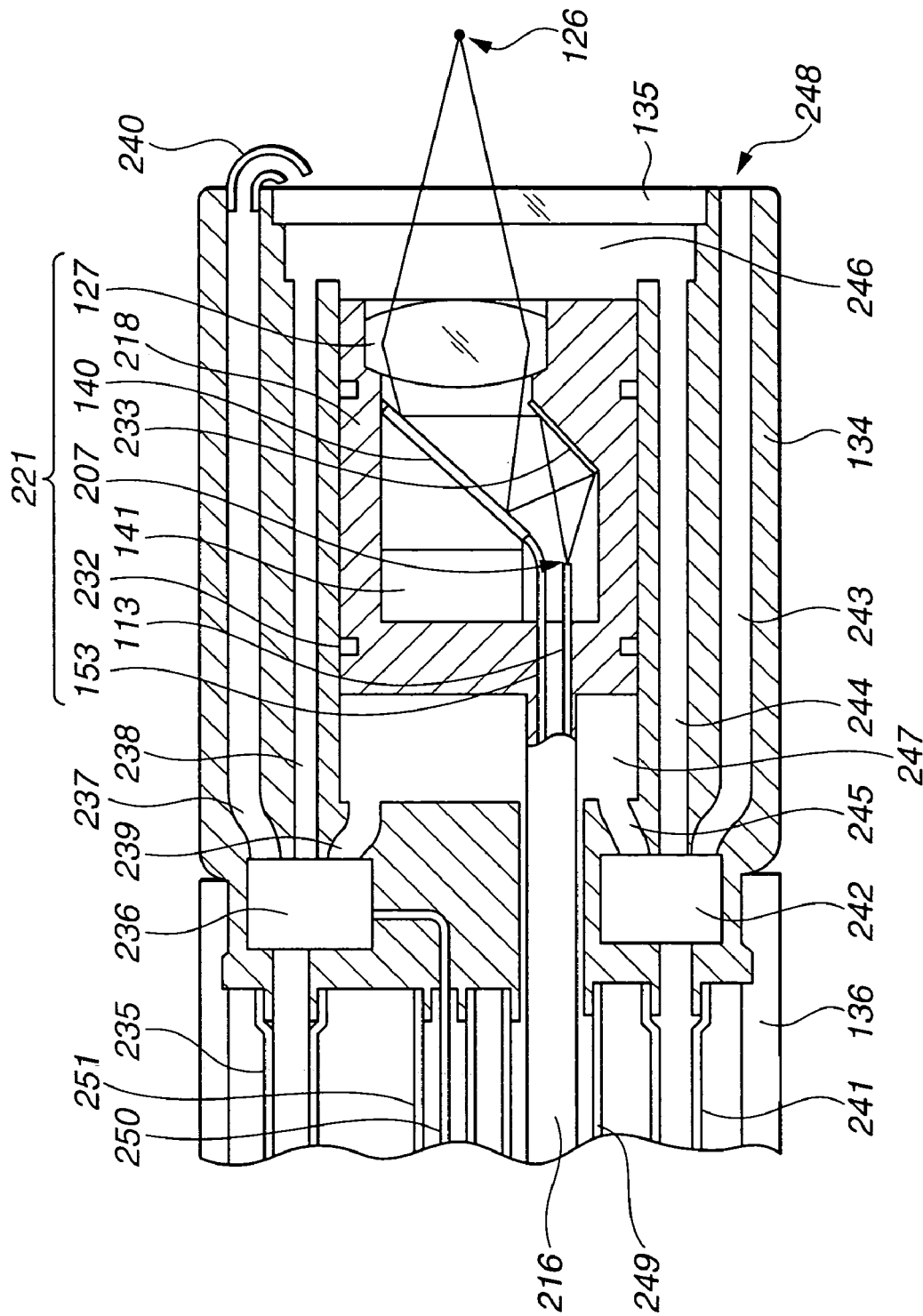
FIG. 47 is a cross-sectional diagram illustrating the configuration of the tip portion of the optical scanning probe according to a ninth embodiment.
Figure 48:
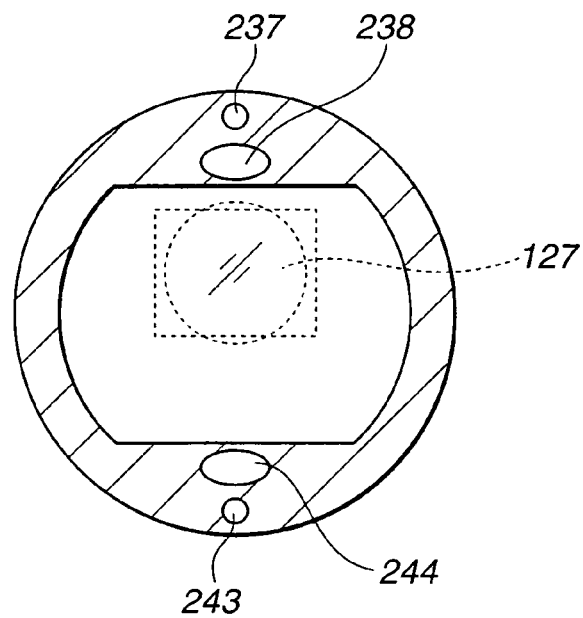
FIG. 48 is a cross-sectional diagram of a housing.

FIG. 47 and FIG. 48 illustrate a ninth embodiment. Only the portions different from the fifth embodiment will be described with reference to the drawing, and other portions will be denoted with the same reference numerals as those in the fifth embodiment and description thereof will be omitted. FIG. 47 is a cross-sectional diagram illustrating the configuration of the tip portion of the optical scanning probe according to the ninth embodiment, and FIG. 48 is a cross-sectional diagram of the housing.

The light scanning unit 221 has the same configuration as with the fifth embodiment and the eighth embodiment, but the light emitted from the emitting end 207 from the fifth optical fiber 113 is guided to the scanning mirror 140 by a reflecting mirror 233. Also, watertight packing 232 is provided to the lens frame 218.

A water feed pipe 235 is connected to the housing 134, and a first water feed tube 237 connected to a water feed nozzle 240, a second water feed tube 238 passing through to a first cylinder 246, a third water feed tube 239 passing through to a second cylinder 247, and a water feed valve 236 for supplying fluid fed to the water feed pipe 235 to the first water feed tube 237, the second water feed tube 238, and the third water feed tube 239 based on driving signals transmitted to a driving cable 250, are provided.

Also, in the same way, a suction pipe 241 is connected to the housing 134, and a first suction tube 243 connected to a suction opening 248, a second suction tube 244 passing through to the first cylinder 246, a third suction tube 245 passing through to the second cylinder 247, and a suction valve 242 for connecting the water suction pipe 241 to one of the first suction tube 243, the second suction tube 244, and the third suction tube 245, based on driving signals transmitted to the same driving cable as the unshown driving cable 250, are provided.

The water feed pipe 235 and the water suction pipe 241 are detachably connected to unshown water feed means and suction means of the observation apparatus by a fluid connector, with pressurized water and negative pressure being applied thereto respectively, at all times.

Driving the water feed valve 236 and the suction valve 242 moves the light scanning unit 221 integrally to the left and right, i.e., in the depth direction of the observation object 125, thereby realizing depth-wise scanning of the observation point 126.

The water feed pipe 235 and the second water feed tube 238 are connected by the water feed valve 236, and at the same time the water suction pipe 241 and the third suction tube 245 are connected by the suction valve 242. This causes water to be injected into the first cylinder 246, and the water in the second cylinder 247 to be removed. The difference between the pressure in the first and second cylinders moves the light scanning unit 221 in the left direction, and the observation point 126 moves in the shallow direction.

Connecting the water feed pipe 235 and the third water feed tube 239 with the water feed valve 236, and at the same time connecting the water suction pipe 241 and the second suction tube 244 with the suction valve 242 moves the light scanning unit 221 in the right direction instead, and the observation point 126 moves in the deep direction.

Also, connecting the water feed pipe 235 and the first water feed tube 237 with the water feed valve 236 allows water to be spouted from the water feed nozzle 240, so that the observation window 135 can be cleaned. Also, connecting the water suction pipe 241 and the first suction tube 243 with the suction valve 242 allows excessive water to be suctioned from the suctioning opening.

Also, scanning of the light scanning unit 221 can be performed with only the second water feed tube 238 and second suction tube 244, or the third water feed tube 239 and the third suction tube 245.

While water has been described as the fluid used for scanning in the depth direction here, other fluids with a refractive index close to that of the body (n=1.3 to 1.5) (e.g., physiological saline or glycerin or the like) may be used instead, as a matter of course.

Figure 49:
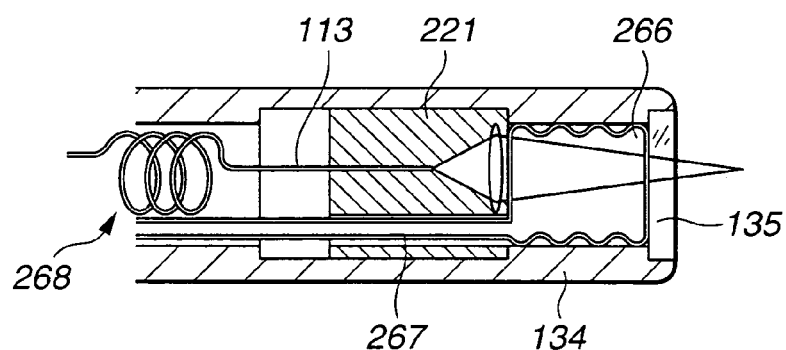
FIG. 49 is a cross-sectional diagram illustrating the configuration of the tip portion of the optical scanning probe according to a modification of the ninth embodiment.
Figure 50:
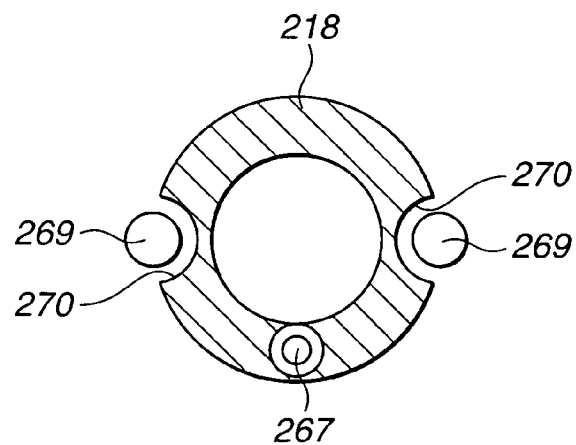
FIG. 50 is a cross-sectional diagram of the lens frame of the optical scanning unit according to a modification of the ninth embodiment.

FIG. 49 and FIG. 50 illustrate a modification of the ninth embodiment. Only the portions different from the ninth embodiment will be described, and the other portions will be denoted with the same reference numerals as in the ninth embodiment.

A diaphragm 266 configured of a transparent resin, preferably PET (polyethylene terephthalate) or polyurethane, with a fluid having a refractive index generally the same as that of a body sealed inside, is provided to the tip side of the light scanning unit 221. An integrally-configured tube 267 is provided inside the diaphragm 266. Introducing in or suctioning out fluid to and from the diaphragm 266 by the tube 267 allows the volume of the refractive index rectifying fluid within the diaphragm 266 to be increased or reduced, thereby moving the light scanning unit 221 to the left and right, thus performing the depth-wise direction scanning in the same way as with the above-described ninth embodiment. The light scanning unit 221 is adhered to the diaphragm 266 at the right end portion, but an arrangement may be made wherein there is no adhesion and the light scanning unit 221 is pressed against the diaphragm 266 by unshown pressing means.

The fifth optical fiber 113 is provided with a fiber slack suction portion 268 formed in a looped shape for suctioning the slack due to advancing and retreating of the light scanning unit 221. Such a fiber slack suction mechanism is also effective provided to configurations of the above-described eighth embodiment and ninth embodiment, as well.

As shown in FIG. 50, the lens frame 218 of the light scanning unit 221 has guides 269 provided to the housing 134 shown in FIG. 49 and guide grooves 270 provided facing these, so the light scanning unit 221 can be advanced and retreated without rotating.

Due to the configuration of the modification, even fluid-driven mechanisms can have a simplified watertight mechanism, and can be configured smaller.

Tenth Embodiment

Figure 51:
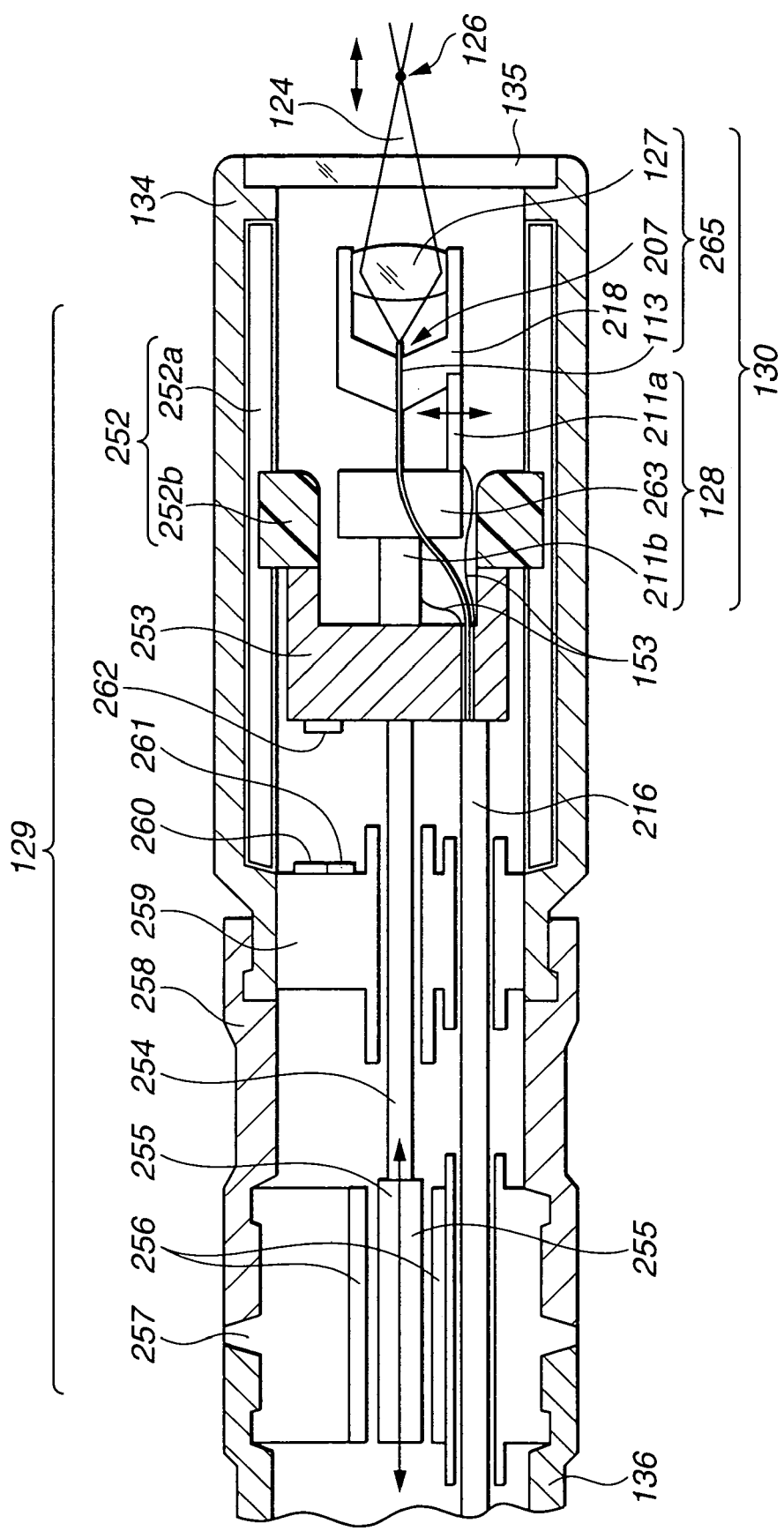
FIG. 51 is a cross-sectional diagram illustrating the configuration of the tip portion of the optical scanning probe according to a tenth embodiment.
Figure 52:
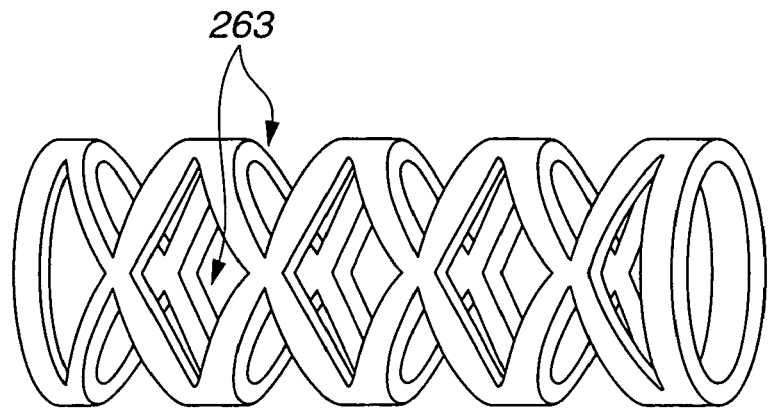
FIG. 52 is a diagram for describing an example of the configuration of a hollow spring.
Figure 53:
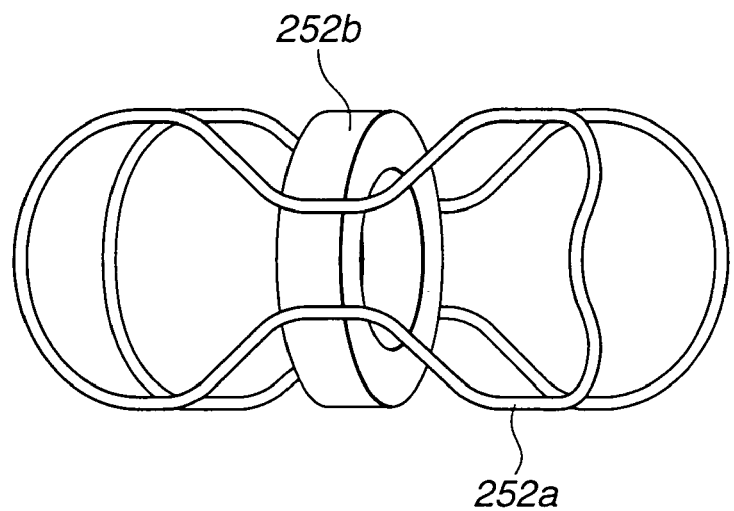
FIG. 53 is a diagram for describing another example of the configuration of a hollow spring.

FIG. 51 through FIG. 53 illustrate a tenth embodiment. Only the portions different from the fifth embodiment will be described with reference to the drawing, and other portions will be denoted with the same reference numerals as those in the fifth embodiment and description thereof will be omitted.

FIG. 51 is a cross-sectional diagram illustrating the configuration of the tip portion of the optical scanning probe according to the tenth embodiment. FIG. 52 is a diagram for describing an example of the configuration of a hollow spring according to the tenth embodiment. FIG. 53 is a diagram for describing another example of the configuration of a hollow spring according to the tenth embodiment.

The fifth optical fiber 113 and the condenser lens 127 and lens frame 218 make up a lens unit 265. The optical scanning means 128 shown in FIG. 20 is configured of a bimorph piezoelectric device 211a connected to the lens unit 265, a connecting member 263, and a bimorph piezoelectric device 211b connected to an attaching base 253. The lens unit 265 and the optical scanning means 128 make up the object unit 130. The light emitted from the emitting end 207 from the fifth optical fiber 113 is guided to the observation point 126 by the condenser lens 127, and returns to the emitting end 207, with the observation light 124 being scanned in the vertical direction by the bimorph piezoelectric device 211a and the direction perpendicular to the drawing by the bimorph piezoelectric device 211b, i.e., in the direction perpendicular to the vertical direction, and combining both enables two-dimensional scanning as with the fifth embodiment.

The attaching base 253, a hollow spring 252, a driving shaft 254, a permanent magnet 255, an electromagnet 256, an LED 260, a photodiode 261, a reflecting plate 262, a detector base 259, a relay sheath 258, and a relay base 257, make up the depth-wise direction scanning means 129.

Applying a driving current to the electromagnet 256 generates a driving force proportionate to the driving current in the permanent magnet 255, which is transmitted from the driving shaft 254 to the attaching base 253. Consequently, the observation point of the focal point moves in the depth-wise direction of the observation object 125. The end portion of the bimorph piezoelectric device 211b is fixed to the attaching base 253. Also, the attaching base 253 is fixed to a fixing portion 252b provided partway along a spring portion 252a of the hollow spring 252. Both ends of the hollow spring 252 are fixed to the housing member 134.

FIG. 52 and FIG. 53 show configuration examples of the hollow spring 252. FIG. 52 shows one example of the hollow spring 252, wherein notches 263 are provided in a super-elastic alloy (SEA) pipe, and FIG. 53 illustrates an arrangement wherein a spring portion 252a is formed of a wire spring, to which a fixing portion 252b is joined.

A described above, an electromagnetic actuator is formed of the permanent magnet 255 and the electromagnet 256, and the attaching base 253 is moved to the left and right due to the driving force of the electromagnetic actuator, i.e., in the axial direction of the optical probe 105, so as to move the lens unit 265 provided to the object unit 130 in the depth-wise direction, thus moving the observation point 126 in the depth-wise direction.

When the driving force of the permanent magnet 255 and the electromagnet 256 is gone, the attaching base 253 returns to the original portion due to the returning force of the hollow spring 252. The position of the attaching base 253, i.e., the scanning position in the depth-wise direction, is obtained by the optical power and light intensity for the light irradiated from the LED 260 serving as the light source provided on the detector base 259 fixed to the housing 134 and reflected off of the reflecting plate 262 being detected by the photodiode 261 which is a detector.

That is to say, the detection of the amount of focal point movement is performed by measuring the distance between the fixing portion and movable portion of the focal point moving means at the tip portion of the optical scanning probe 105. Also, the driving current of the electromagnet is proportionate to the driving force, and the driving force is generally balanced with the elasticity of the hollow spring 252. The elasticity serves as a function for moving displacement, so the position of the attaching base 253 can be estimated from the driving current of the electromagnet. Note that a magnetism generator and a magnetism detector may be provided instead of the LED 260 and the photodiode 261, to detect the scanning position by the change in magnetic force.

Also, the relay base 257 on which the electromagnet 256 is provided is an actuator holding member, and is connected to the sheath 136. Further, the relay base 257 is connected to the housing 134 with the relay sheath 258 formed of a material which has great rigidity in the axial direction and which has little rigidity in the direction perpendicular to the axis. Also, the aforementioned driving shaft 254 is similarly formed of a material which has great rigidity in the axial direction and which has little rigidity in the direction perpendicular to the axis.

A flexible outer cylinder, i.e., a sheath 136, is provided between the hard tip optical portion having the focal point moving means, and the optical portion and actuator holding member. Thus, the actuator which has a great driving force generally tends to be large, but separating the actuator portion and the optical portion thus enables the hard portion length to be reduced, thereby improving insertability to the body cavity and ease of handling, and particularly insertability and ease of handling in the event of using by inserting through the treatment equipment channel of an endoscope.

Also, the rigidity of the cable 216 which houses the driving cable 153 for driving the bimorph piezoelectric device 211a and the bimorph piezoelectric device 211b of the fifth optical fiber 113 is great, and accordingly can serve as both the cable 216 and driving shaft 254. Thus, the space usage efficiency within the probe can be improved, and accordingly the probe can be further reduced in diameter.

Also, the hollow spring 252 is formed of a shape-memory alloy (SMA) with a shape such as shown in FIG. 52, and only one end portion is fixed to the housing 134. This configuration can serve as both actuator and spring means by further providing unshown heating means, such as applying electric current to the SMA itself for example, and preferably providing cooling means such as water.

Also, a configuration such as shown in this configuration, wherein the actuator portion and the optical portion are separated, and driving force is transmitted by the driving shaft 254 and the relay sheath 258, can also be applied to other embodiments, the eighth embodiment for example. The direct driving force by the rotating cam 212 and the protrusion 217 can be transmitted to the driving shaft 254, with the driving shaft 254 advancing and retreating the light scanning unit 221.

Figure 54:
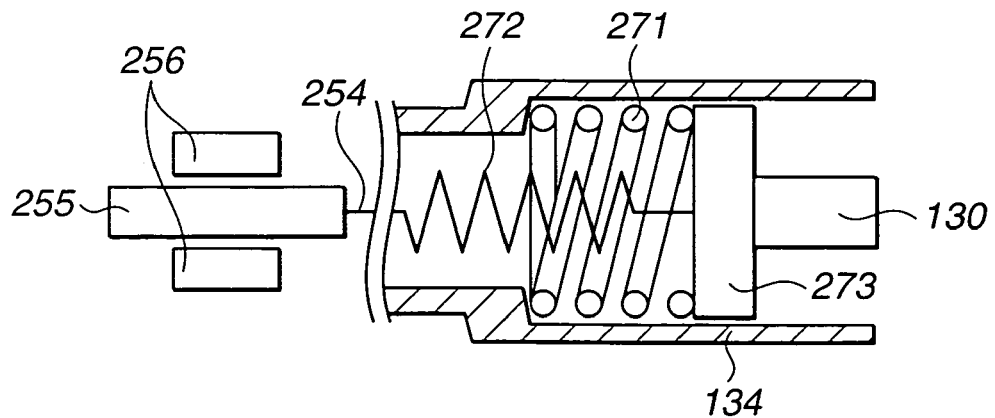
FIG. 54 is a diagram illustrating the depth-wise direction scanning means in a modification of the tenth embodiment.
Figure 55:
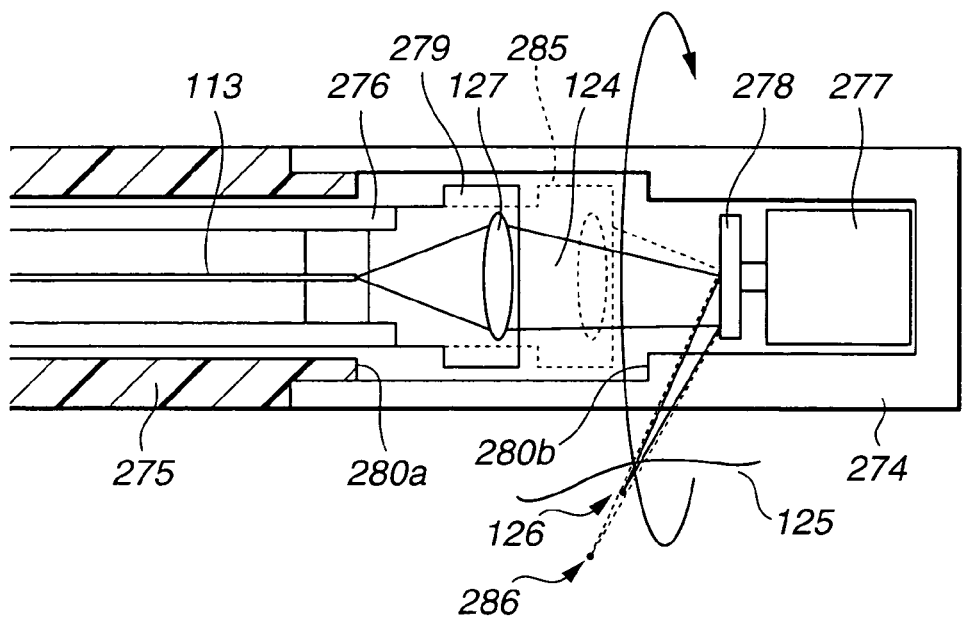
FIG. 55 is a cross-sectional diagram illustrating the configuration of the tip portion of the optical scanning probe according to an eleventh embodiment.

FIG. 54 illustrates a modification of the tenth embodiment. Only the portions different from the tenth embodiment will be described, and other portions will be denoted with the same reference numerals as those in the tenth embodiment.

The object unit 130 is fixed to a spring base 273. A compression spring A 271 with a spring constant of k1 is provided between the spring base 273 and the housing 134 instead of the hollow spring 252 in the tenth embodiment, and a pulling spring B 272 with a spring constant of k2 is provided between the spring base 273 and the driving shaft 254. The amount x of advance or retreat of the object unit 130 is in a relation of x=(k2/k1)y, wherein y is the amount of advance or retreat of the driving shaft 254. The springs 271 and 272 make up the displacement conversion mechanism. Setting k2 so as to be small as to k1 allows the amount of displacement of the actuator made up of the permanent magnet 255 and the electromagnet 256 to be compressed and transmitted. Thus facilitates positioning of the object unit 130.

Now, while the displacement conversion mechanism has been configured here with two types of springs, this may be configured of multiple springs with two types or more of spring constant. Also, a mechanism has been described here for compressing the displacement, but a mechanism which enlarges the displacement may be used. The displacement conversion mechanism is configured such that the amount of force transmitted to the motive force transmitting means and the displacement are in a unique relation.

Also, instead of providing an actuator made up of the permanent magnet 255 and the electromagnet 256 as described above, the object unit 130 at the probe tip can be moved in the depth-wise direction, i.e., in the axial direction of the probe so as to be positioned, by forming the driving shaft 254 as with a sufficiently flexible wire, which is passed through the entire length of the optical scanning probe, and pulled manually or by an unshown actuator at the operating side of the probe.

At this time, positioning can be performed while monitoring the position with the position detecting means made up of the LED 260, photodiode 261, and reflecting plate 262, illustrated in the tenth embodiment.

With this configuration, fine positioning in the order of micrometers is generally difficult with wire driving, but the displacement compressing mechanism formed of the spring A 271 and spring B 272 enables a positioning mechanism by wire drive. This configuration is advantageous in that the probe tip can be configured even smaller, since the actuator can be configured at the probe operating side or externally.

Examples of an actuator for wire driving include the direct driving mechanisms using screws or cams according to the eighth embodiment shown in FIGS. 44, 45, and 46, and wire spooling mechanisms using pulleys. Also, general commercially-available large-size actuators can be used, and further, can be provided externally from the probe, so the probe can be configured inexpensively.

Eleventh Embodiment

FIG. 55 through FIG. 58 illustrate an eleventh embodiment. Only the portions different from the fifth embodiment will be described with reference to the drawing, and other portions will be denoted with the same reference numerals as those in the fifth embodiment and description thereof will be omitted.

The outer covering of the optical scanning probe 105 is made up of a probe sheath 275 configured of a flexible resin, and a transparent sheath 274 connected thereto. A direct driving shaft 276 is provided within the probe sheath 275, and an object unit 279 is provided on the top thereof. The object unit 279 comprises the end portion of the fifth optical fiber 113 and the condenser lens 127. A motor 277 and DOE (Diffractive Optical Element) mirror 278 are provided within the transparent sheath 274.

Figure 56:
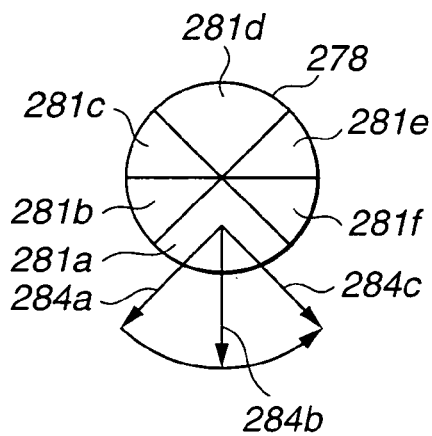
FIG. 56 is a frontal view of a DOE scanning mirror.

The observation light 124 emitted from the end of the fifth optical fiber 113 is reflected by the DOE scanning mirror 278, and is converged at the observation point 126. FIG. 56 shows the DOE scanning mirror 278. The DOE scanning mirror 278 is made up of six DOE mirrors 281a through f. Making description with the DOE mirror 281a, the DOE mirror 281a has a diffractive lattice formed such that incident light rays from the front in FIG. 56 are reflected downwards, indicated by 284b. Rotating the DOE rotating mirror 278 causes the direction of light rays to move from 284a to 284c. The DOE mirrors 281b through f are also configured of a DOE mirror as with 281a, and accordingly rotating the DOE scanning mirror 278 with the motor 277 repeatedly scans the light ray from 284a to 284c. Thus, the observation point 126 is scanned in an arc shape. This corresponds to the light scanning means 128 in the fifth embodiment.

Also, moving the direct driving shaft 276 in the direction of the probe tip presses the object unit 279 out, and moving to the position 285 allows moving the convergence point 126 to the position 286. This is the depth-wise direction scanning means 129 in the fifth embodiment, and can change the observation depth within the observation object 125.

Figure 57:
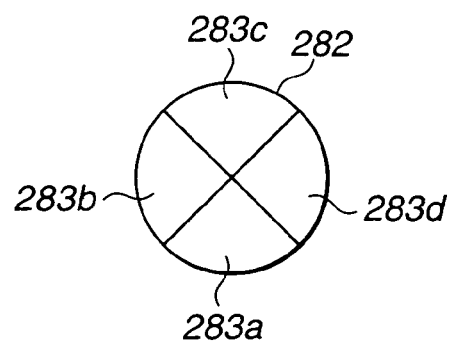
FIG. 57 is a frontal view of a pyramid mirror according to the eleventh embodiment.
Figure 58:
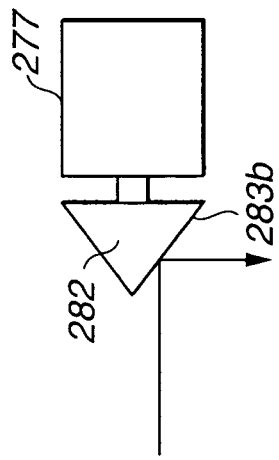
FIG. 58 is a side view of the pyramid mirror and a motor in the event of using the pyramid mirror instead of the DOE scanning mirror.

Also, instead of the DOE scanning mirror 278, a pyramid mirror 282 such as shown in FIG. 57 and FIG. 58 may be used. FIG. 57 is a frontal view of the pyramid mirror 282. FIG. 58 is a side view of the pyramid mirror 282 and motor 277. The pyramid mirror 282 has reflective faces 283a through d, and the same operations as the DOE scanning mirror 278 can be performed by rotating the pyramid mirror 282.

Twelfth Embodiment

Figure 59:
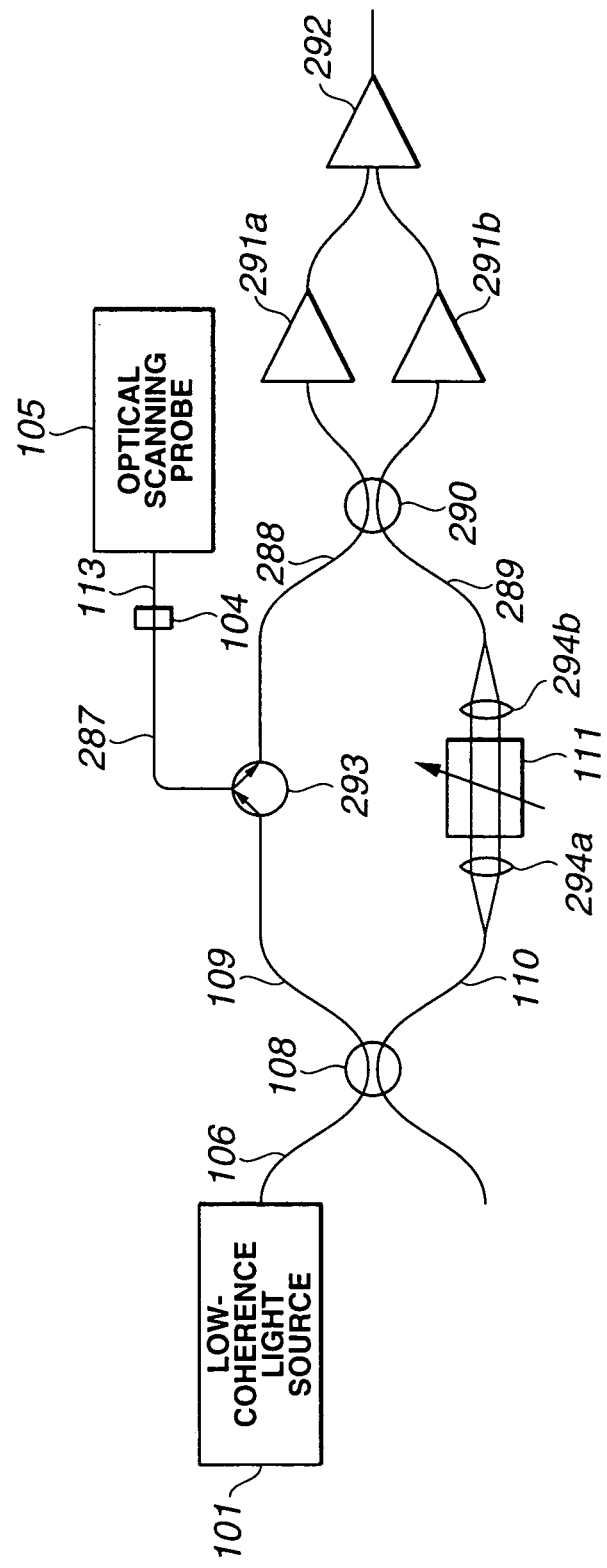
FIG. 59 is a configuration diagram illustrating the configuration of an optical scanning observation apparatus according to a twelfth embodiment of the present invention.

FIG. 59 illustrates a twelfth embodiment. Only the portions different from the fifth embodiment will be described with reference to the drawing, and other portions will be denoted with the same reference numerals as those in the fifth embodiment and description thereof will be omitted.

The present invention can also be realized using an interferometer of a different configuration to that in FIG. 19. The light guided to the third optical fiber 109 is guided to an optical fiber 287 by an optical circulator 293, and is guided to the fifth optical fiber 113 by the optical connector 104. The light is guided to the optical scanning probe 105, and the light returning from the object of observation is guided to the optical fiber 287 again, but is guided to an optical fiber 288 by the optical circulator 293.

Also, light guided to the fourth optical fiber 110 is guided to the frequency shifter 111 by a collimator 294a, and is guided to the optical fiber 289 by a collimator 294b. The light guided to the optical fiber 288 and the light guided to the optical fiber 289 are mixed by an optical coupler 290, and the light from the optical coupler 290 is guided to detectors 291a and 291b. Here, the optical path length of the optical path where light from the third optical fiber 109 passes through the optical circulator 293, is guided to the optical scanning probe 105, emitted to the object of observation, and the reflected light passes through the optical circulator 293, and through the optical fiber 288 and is guided to the optical coupler 290, is the body side optical path length. Also, the optical path length of the optical path from the fourth optical fiber 110 through the frequency shifter 111, and through the optical fiber 289 to the optical coupler 290, is the reference side optical path length.

Thus, as with the fifth embodiment, interference light is obtained in the event that the body side optical path length and reference side optical path length accord within the coherence length range of the low-coherence light source.

Now, the signals generated from the interference light received at the detectors 291a and 291b are of opposite phases, and signals from other fixed light and noise light are of the same phase, so amplifying the difference of the signals of the detectors 291a and 291b with a difference amplifier 292 doubles the interference signals, and the noise components are suppressed, thereby greatly improving the S/N ratio.

Also, using a laser light source with a long coherence light instead of the low-coherence light source 1 can yield capabilities the same as those of an interference microscope. Also, terminating the fourth optical fiber 110 with a refractive index rectifying substance or the like, instead of using the configuration of the reference side 133 shown in FIG. 19 in the fifth embodiment, enables a laser optical scanning microscope to be configured. At this time, in the event that the optical diameter of the fifth optical fiber 113 shown in FIG. 20, the input NA (numerical aperture) and output NA of the condenser lens 127 satisfy the confocal conditions, this forms a scanning confocal microscope. In this case, detecting devices having amplifying properties upon photoelectric conversion are preferably used for the photo-detector 102, such as a photomultiplier tube, an avalanche photodiode, or the like. In this case, there is no modulation by the frequency shifter 111, so the demodulator 119 becomes unnecessary.

It is self-evident that the various components of the above-described fifth through twelfth embodiments can be combined to form an optical scanning observation apparatus, and that the respective advantages can be obtained. For example, the fluid actuator shown in FIG. 47 according to the fifth embodiment can be used instead of the actuator made up of the permanent magnet 255 and the electromagnet 256 shown in FIG. 51 according to the tenth embodiment. In this case, a gas can be used instead of a fluid.

Moreover, in the event of providing an actuator within the optical scanning probe, so that the actuator drives flexible motive force transmitting means, the actuator may be one which provides movement in the axial direction of the probe such as an electromagnetic actuator, one which provides rotational driving, and so forth. The actuator and the focal point variation mechanism are connected with flexible motive force transmitting means, and the portion where the motive force transmitting means are present is configured so as to be flexible.

Each of the above-described fifth through twelfth embodiments has the following advantages.

(1) An optical scanning probe can be provided which has a short tip hard portion, and a focal point variation mechanism capable of precise control.

(2) An optical scanning probe can be provided which is capable of precise control even with flexible, direct driving, motive force transmitting means.

(3) An optical scanning probe can be provided comprising an actuator on the tip portion for enabling precise control, while shortening the length of the tip hard portion.

(4) An optical scanning probe can be provided wherein the position of the focal point can be accurately detected, and properly reflected on the image, even in the event that precise control is not performed by the flexible motive force transmitting means.

(5) An optical scanning probe can be provided with a reduced probe size and which is capable of fine control of the position of the focal point.

(6) An optical scanning probe can be provided wherein, in a combination with low-coherence interference, the detection position from the low-coherence interference and the converging position accord even in the event that the focal position is changed.

(7) An optical scanning probe can be provided wherein, in the event of integrally moving the tip optical unit in the optical axis direction, tension occurring in the fiber due to moving does not inhibit movement.

(8) An optical scanning probe can be provided wherein speedy focal position changing is realized.

(9) An optical scanning probe can be provided wherein reflection from the interface is suppressed, thereby improving the SIN ratio.

Next, an optical scanning observation apparatus (also called optical scanning probe apparatus) capable of obtaining optical scanning observation images in different depth-wise positions and the like can be obtained by providing moving means for moving at least the entire tip of an optical scanning probe will be described.

As for the background of the following embodiments, with the preceding examples, structures were employed wherein means for scanning in the depth-wise direction are provided in the tip portion of the optical scanning probe so that images in the depth-wise direction can be obtained, so the outer diameter of the optical scanning probe becomes large, and the range of use is restricted.

In the event of using the optical scanning probe by inserting through a channel of an endoscope for example, this can only be used with endoscopes with large-diameter channels. Also, even though usage with endoscopes with large-diameter channels may be possible, there is the shortcoming that insertion into the body of the patient imposes distress thereupon, and the task of the technician is not as smooth.

Accordingly, it is an object of the following embodiments to provide an optical scanning observation apparatus with a wide range of application, capable of scanning in the depth-wise direction and so forth, without increasing the external diameter of the scanning probe.

Thirteenth Embodiment

Now, the configuration of the optical scanning observation apparatus according to a thirteenth embodiment will be described with reference to FIG. 60 through FIG. 70.

Figure 60:
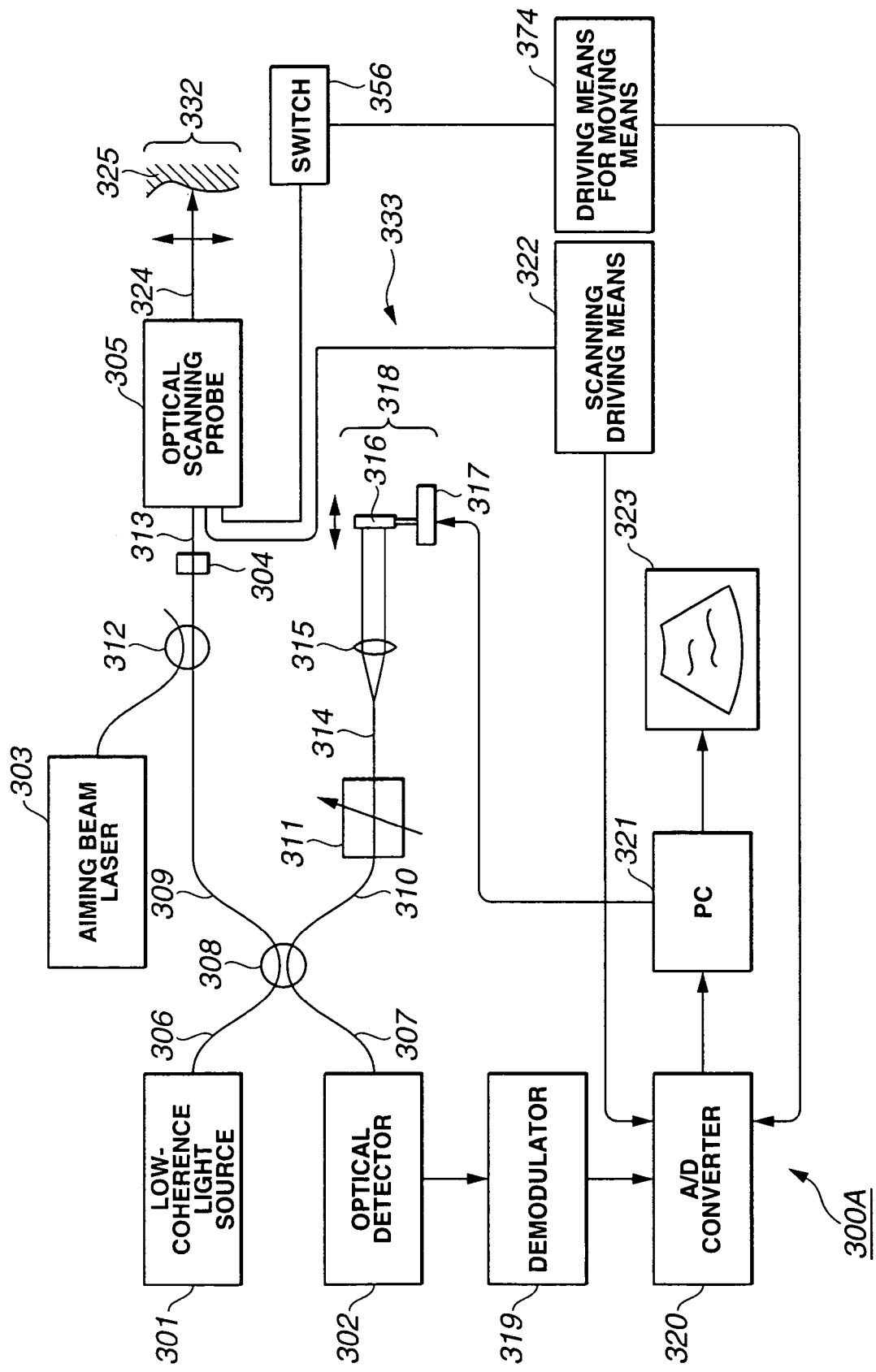
FIG. 60 is an overall configuration diagram of an optical scanning observation apparatus according to a thirteenth embodiment of the present invention.

With the optical scanning observation apparatus 300A illustrated in FIG. 60 according to the thirteenth embodiment, near-infrared low-coherence light irradiated from a low-coherence light source 301 is guided to a first optical fiber 306, and is branched into a third optical fiber 309 and a fourth optical fiber 310 by an optical coupler 308 having four input/output.

Visible laser light emitted from an aiming beam laser 303 is multiplexed by an optical coupler 312. The third optical fiber 309 is connected to a fifth optical fiber 313 by an optical connector 304, and transmits low-coherence light to an optical scanning probe 305.

Scanning a later-described object unit 330 built into the tip portion of the optical scanning probe 305 allows observation light (observation beam) 324 to be scanned, and convergence to be performed at the observation point near an object of observation 325.

As shown in FIG. 61, the optical scanning probe 305 is covered with a slender and flexible sheath 341, and can be inserted in a channel 343 of an endoscope 342. The endoscope 342 has a slender insertion portion 344, and an operating unit 345 provided on the rear end of the insertion portion 344, with a treatment instrument insertion opening 346 which communicates with the channel 343 provided within the insertion portion 344 provided near the operating unit 345, from which the optical scanning probe 305 can be inserted.

Figure 62:
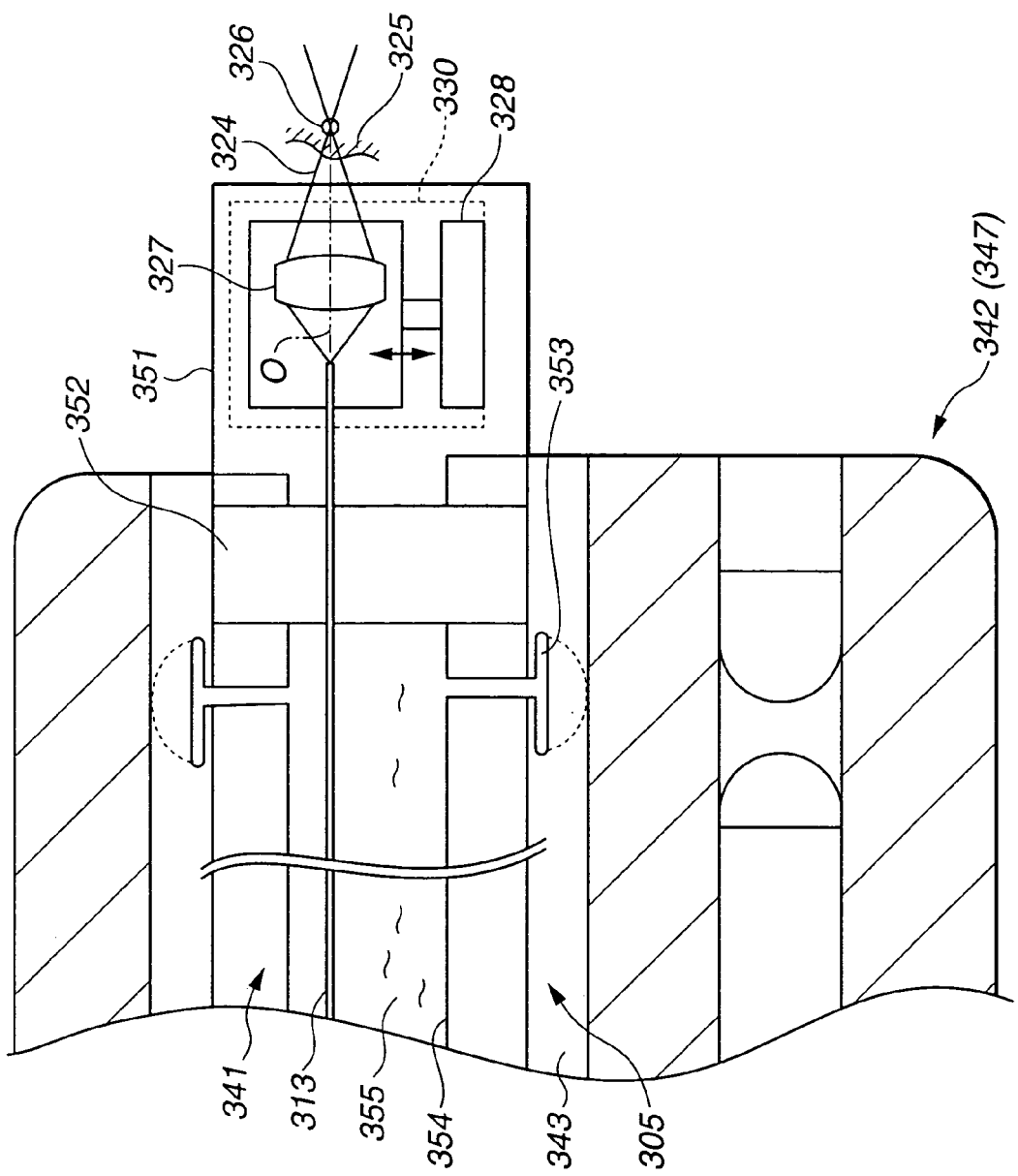
FIG. 62 is an enlarged view around the tip shown in FIG. 61.

In the event that the user desires to inspect whether or not a diseased tissue, under observation with the endoscope 342, the tip side of the optical scanning probe 305 can be protruded from the tip of the channel 343 as shown enlarged in FIG. 62, and set near the surface of the tissue which is the object of observation 325, thereby obtaining an image with the optical scanning probe 305, or more specifically, a microscope image with a greater numeral aperture, and a higher magnification by the condenser lens 327 with a near focus.

FIG. 62 illustrates the configuration at the tip side of the optical scanning probe 305, along with the configuration of the tip portion 347 of the endoscope 342.

The optical scanning probe 305 has the opening of the tip portion thereof covered with a hard tip frame 351 covered with an unshown cover glass, so that the hard tip portion is formed, with the rear end of the tip frame 351 being connected airtight and watertight to an elastic cylinder 352 which expands and shrinks in the longitudinal direction of the probe 305.

The rear end of the elastic cylinder 352 is connected to the tip portion of the sheath 341, and a generally ring-shaped balloon 353 is provided at the perimeter near the tip portion of this sheath 341. The balloon 353 communicates with an interior fluid channel 354 via a hole provided near the tip portion of the sheath 341.

A fluid, more specifically pressurized air (compressed air) 355 is fed from the operating side via the fluid channel 354, thereby expanding the balloon 353 as indicated by the dotted lines in FIG. 62, so as to come into contact with the inner walls of the channel 343, and thus fixing the tip side of the probe 305.

That is to say, the optical scanning probe 305 is fixed on the inner wall face of the channel 343 of the endoscope 342 by the perimeter face at the position where the balloon 353 is provided, so the portion where the balloon 353 is provided functions as a fixing member or fixing means.

Also, as described below, extending or shrinking the elastic cylinder 352 in the longitudinal direction allows the tip side of the optical scanning probe 305 to move the tip frame 351 thereof in the longitudinal direction with the position fixed by the balloon 353 as a fixed reference position, and the elastic cylinder 352 functions as a moving member or moving means.

Also, feeding the pressurized air 355 extends the elastic cylinder 352 in the longitudinal direction, thereby moving the tip frame 351 which has the rear end thereof connected to the front end of the elastic cylinder 352 forwards, enabling scanning of the observation point 326 in the longitudinal direction of the probe.

As shown in FIG. 62, the low-coherence light emitted from the tip portion of the fifth optical fiber 313 is converged at the observation point 326 within the observation object 325 as an observation light (observation beam) 324 in the optical axis 0 direction by the condenser lens (object lens) 327.

The object unit 330 having the end portion of the fifth optical fiber 313 and the condenser lens 327 has optical scanning means 328, and scans the observation object 325 which is the subject, while moving the observation light 324 and the observation point 326 in the longitudinal direction of the probe, i.e., in a two-dimensional direction perpendicular to the front and back direction. That is to say, this object unit 330 forms an optical scanning optical system for two-dimensionally scanning the observation light 324.

Note that the base portion for example of the optical scanning means 328 making up the object unit 330 is fixed on the inner wall of the tip frame 351, and upon the tip frame 351 being moved back and forth, the object unit 330 is also moved back and forth. Expanding or shrinking the elastic cylinder 352 as described above in the longitudinal direction moves the object unit 330 along with the tip frame 351, so the observation point 326 can be scanned in the depth-wise direction of the observation object.

The optical scanning means 328 are driven by the scanning driving means 322 shown in FIG. 60.

On/off switching operations of the driving of the driving means 374 for the moving means, by supplying or ejecting a fluid for the elastic cylinder 352 serving as the moving means for moving the tip frame 351 forwards and backwards, can be performed with a switch 356.

Also, the switch 356 for switching driving/stopping of the driving means 374 may be formed with a hand switch at the rear end side of the optical scanning probe 305 or on the endoscope 342, or as a foot switch or the like.

As shown in FIG. 60, the fourth optical fiber 310 is connected to a frequency shifter 311, and the output of the frequency shifter 311 is introduced to a sixth optical fiber 314. Examples of frequency shifters 311 which can be used are phase-modulation means including acousto-otptical devices (AO), electro-optical device (EO), piezoelectric devices provide with fiber loops, and so forth.

The light emitted from the edge of the sixth optical fiber 314 passes through a collimator lens 315 and is guided to a movable mirror 316. The movable mirror 316 can be moved in the optical axis direction of the emitted light by mirror driving means 317. The edge of the sixth optical fiber 314, the collimator lens 315, movable mirror 316, and the mirror driving means 317, make up optical path length adjusting means 318.

The second optical fiber 307 which is the remaining terminal of the optical coupler 308 is connected to an optical detector 302. Preferably single mode fiber, low-order multi-mode fiber capable of sufficiently maintaining coherence, polarization-maintaining fiber, and so forth, can be used for the first optical fiber 306, the second optical fiber 307, the third optical fiber 309, the fourth optical fiber 310, the fifth optical fiber 313, and the sixth optical fiber 314.

The near-infrared low-coherence light emitted from the low-coherence light source 301 is guided to the first optical fiber 306, and is branched into the third optical fiber 309 and fourth optical fiber 310 by the optical coupler 308. The light guided to the third optical fiber 309 is guided to the optical scanning probe 305 by the optical connector 304 and the fifth optical fiber 313, and is emitted as observation light 324 to the object of observation 325.

Scanning by the observation light 324 and the observation point 326 is performed on the object of observation 325 by the optical scanning means 328 and the elastic cylinder 352 which is the moving means serving as the depth-wise direction scanning means.

The reflected light or scattered light from the object of observation 325 at the observation point 326 returns to the fifth optical fiber 313 through the condenser lens 327, and returns to the third optical fiber 309, retracing the path. The path of this light is the body side 332.

In the same way, the low-coherence light branching to the fourth optical fiber 310 is subjected to frequency transition at the frequency shifter 311, and passes through the sixth optical fiber 314 and is emitted at the collimator lens 315, the light irradiated into the collimator lens 315 is converted into generally parallel light, and is guided to the movable mirror 316. The light reflected by the movable mirror 316 is guided again to the sixth optical fiber 314 by the collimator lens 315, and returns to the fourth optical fiber 310. The path of this light is the reference side 333.

The two lights of the body side 332 and the reference side 333 are mixed by an optical coupler 308. In the event that the optical path length of the body side 332 and the optical path length of the reference side 333 accord within the range of coherence length of the low-coherence light source 301, interference light which has passed through the second optical fiber 307 and which fluctuations of frequencies equal to or double the amount of frequency transition at the frequency shifter 311, is detected by the optical detector 302.

Now, information from the observation point 326 can be constantly obtained as interference light by previously adjusting the position of the movable mirror 316 in the optical axis direction, so as to accord the optical path length of the reference side 333 with one up to the observation point 326 of the body side, by the mirror driving means 317 of the optical path length adjusting means 318.

The detected interference light is converted into electric signals by the optical detector 302. The electric signals are supplied to the demodulator 319. Extracting signals alone near frequencies of equal, double, or higher orders of the frequency transition at the frequency shifter 311, with the demodulator 319, enables signals from the observation point 326 to be detected with a higher S/N ratio by optical heterodyne detection.

The observation point 326 of the observation light 324 can be generally perpendicularly, i.e., two-dimensionally, moved by the scanning driving means 322. Synchronously with the control signals for the scanning, the demodulator 319 signals are acquired by a personal computer (hereafter abbreviated as PC) 321 corresponding to scan position signals of the observation point 326 from the scanning driving means 322 and the driving means 355 of the moving means, via an analog-digital (A/D) converter 320. Displaying the modulated signals corresponding to the scan position signals of the observation point 326 by luminance on the display 323 of the PC 321 allows a two-dimensional tomographic image in the depth-wise direction of the object of observation 325 to be obtained by scanning the observation point 326 of the observation light 324 in a general depth-wise direction with the driving means 374 of the moving means.

FIG. 60 has been used to describe an optical scanning observation apparatus 300A using a low-coherence light source 301, but the confocal-type optical scanning observation apparatus 300B shown in FIG. 63 has approximately the same operations and advantages, and will be described here as the thirteenth embodiment.

Figure 63:
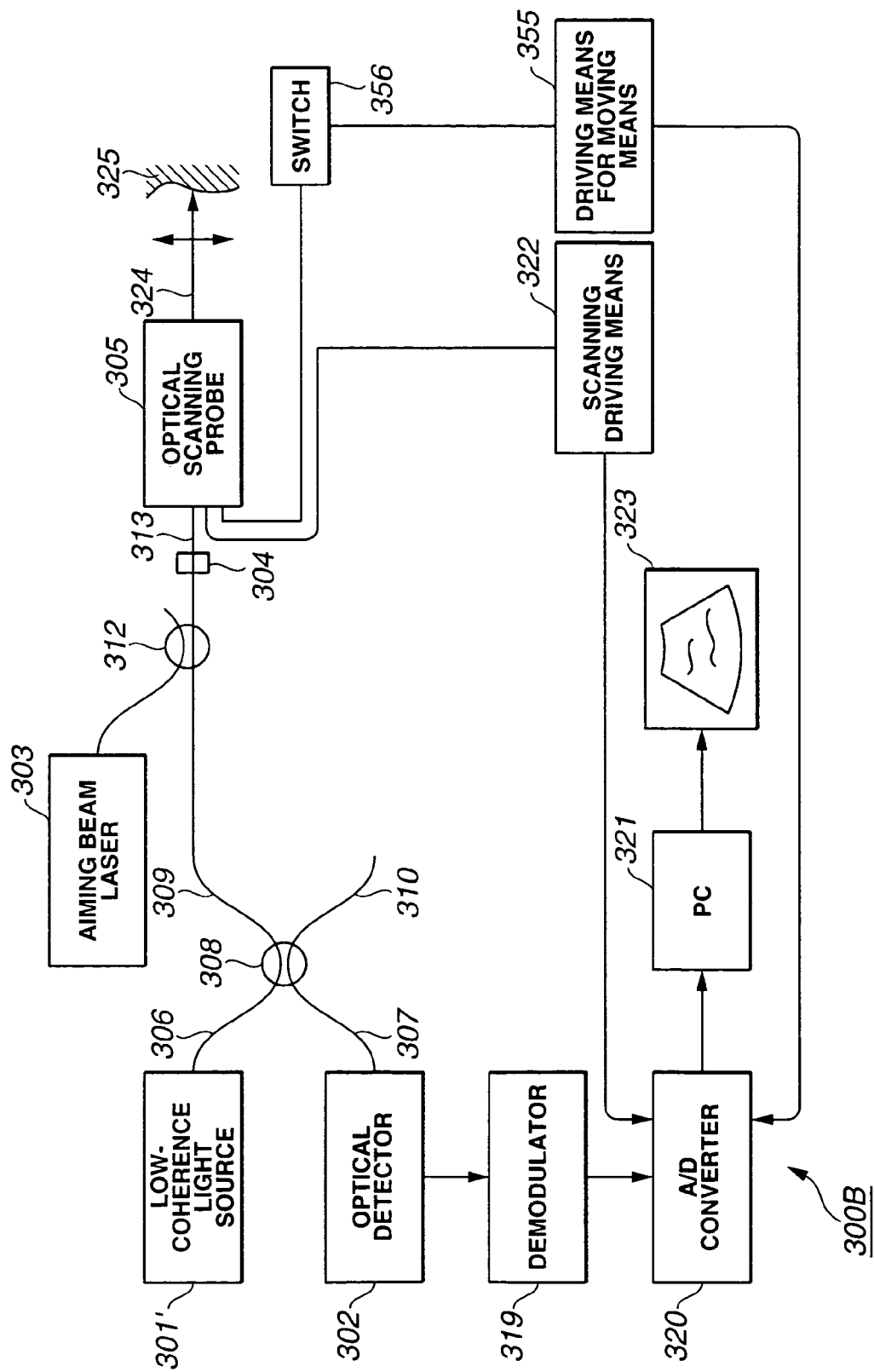
FIG. 63 is a diagram illustrating the overall configuration of a confocal type optical scanning observation apparatus.

With the optical scanning observation apparatus 300B shown in FIG. 63, in FIG. 60 a laser light source 301' for example is used instead of the low-coherence light source 301, and the end of the fourth optical fiber 310 is closed or subjected to non-reflection processing so that the light branched thereto does not return to the optical coupler 308.

Also, in this case, the small-diameter tip face of the optical fiber 313 in FIG. 62 and the observation point 326 are set by the condenser lens 327 so as to be in a confocal relation, with the light emitted from the small-diameter tip face of the optical fiber 313 being focussed at the observation point 326, so only the light reflected at the observation point 326 is input to the small-diameter tip face of the optical fiber 313.

Otherwise, configurations the same as those described with reference to FIG. 60 through FIG. 62 can be used.

Next, a more specific configuration of the optical scanning probe 305 will be described. FIG. 64 illustrates the structure of the tip side of the optical scanning probe 305. Note that in FIG. 64, a different optical scanning optical system 350 as that in FIG. 62 is shown built into the tip frame 351.

A cylindrical balloon 353 which can expand and shrink and function as a fixing means, such as a rubber tube or the like is connected airtight and watertight to the tip portion of the sheath 341 by a hard linking ring 349a, and the tip of the balloon 353 is further connected airtight and watertight to the elastic cylinder 352 serving as moving means by a hard linking ring 349b, and the hard tip frame 351 is connected airtight and watertight to the tip of the elastic cylinder 352. In this case, the tip side of the sheath 341 is formed with the same outer diameter as the sheath 341, as can be understood from FIG. 64.

A fluid channel 354 where fluid is sealed in a hollow portion in the sheath 341 or the like is formed, and an optical fiber 313 is inserted through along the center of the hollow portion, and is sealed at a sealing member 356 at a small hole on the base end portion of the tip frame 351, for example.

Disposed within the tip frame 351 are a ferrule 357 for fixing the tip of the optical fiber 313, a fixed mirror 358 for reflecting light emitted from the tip of the ferrule 357, a mirror device 359 for reflecting the light reflected at the fixed mirror 358 with a scan mirror portion, and a condenser lens 327 for converging the light reflected at the mirror device 359 and irradiating, which emit observation light 324 along the optical axis 0 of the condenser lens 327.

The mirror device 359 is formed of a gimbal mirror for example serving as a scan mirror, and sawtooth signals for scanning in the two-dimensional direction are applied from scanning driving means shown in FIG. 60, and so forth, by a signal line 360. As described above, the light is scanned two-dimensionally in a direction orthogonal to the longitudinal direction of the probe (or the optical axis direction O).

FIG. 65 illustrates the configuration near fluid supply/discharge means near the rear end of the sheath 341.

A nozzle 361 communicating with the fluid channel so as to serve as a connecting portion for supplying and discharging a fluid (more specifically, the pressurized air 355) is provided to the sheath 341 near the rear end of the optical scanning probe 305. This nozzle 361 is connected in an airtight manner to a joint 364 provided on the end of a tube 363 connected to a pressure variation device 362 which is configured of a compressor or the like and forms the driving means 374 in FIG. 60.

Supplying or discharging the pressurized air 355 by changing the pressure of the pressurized air 355 with the pressure variation device 362 allows the balloon 353 to be expanded and fixed, or the elastic cylinder 352 serving as moving means to be moved back and forth.

The pressure variation device 362 performs operations of supplying and discharging the pressurized air 355 by operating the switch 356 on/off. For example, turning the switch 356 on, the pressure variation device 362 consecutively changes the pressurized air 355 between two set values at a predetermined cycle in a consecutive manner, cyclically expanding and shrinking the elastic cylinder 352.

Note that the cycle of expanding and shrinking is set slower than the frame rate for generating one screen of image by two-dimensional scanning of the optical scanning optical system 350. The operation timing for change in pressure in this case is sent to the A/D converter 320, and is used for the image formation timing and so forth. For example, two-dimensional image information is recorded along with information of pressure change.

Also, for example, the PC 321 records information enabling calculation of the amount of movement of the tip side of the elastic cylinder 352, i.e., the amount of movement of the tip frame 351, from the change in pressure, in a recording medium or the like thereof, which can be represented as depth information.

In other words, in the event of setting the optical scanning probe 305 to a state for moving in the depth direction, two-dimensional image information is displayed on the display 323 along with the depth-wise direction information, and is recorded in a recording medium or the like within the PC 321.

In the event that a detachable joint 364 is not connected to the nozzle 361, an airtight lid can be attached to the nozzle 361, thereby sealing off the fluid channel 354.

Figure 66:
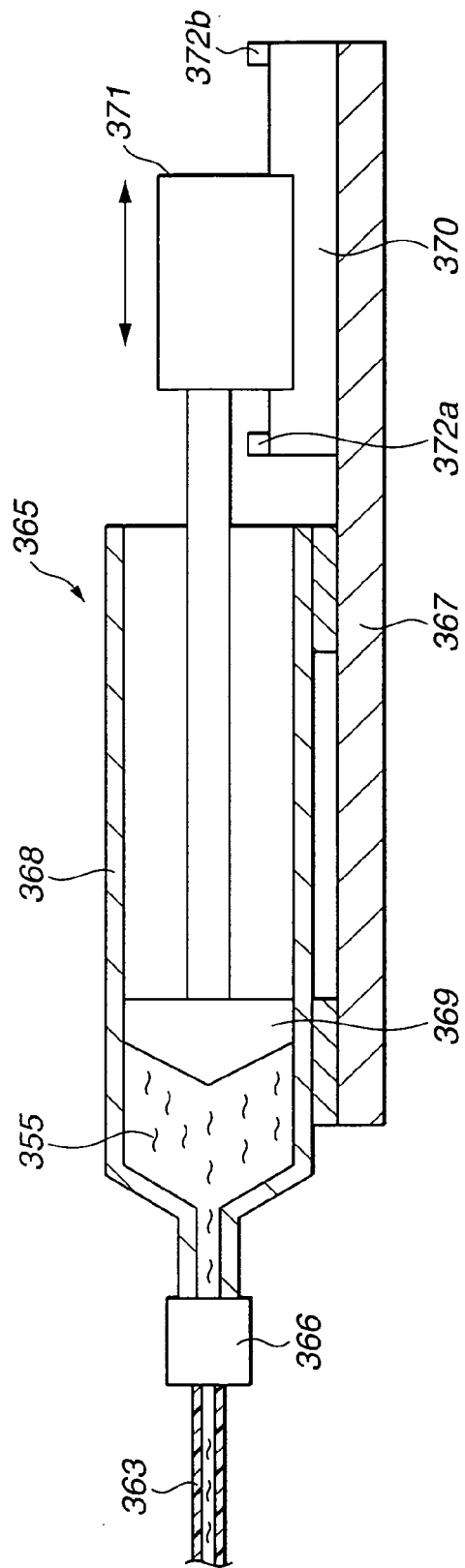
FIG. 66 is a diagram illustrating a modification of the configuration of FIG. 65.

FIG. 66 illustrates a pressure variation device 365 according to a modification of that in FIG. 65. The rear end of the sheath 341 is connected to a syringe 368 with the peripheral face of the cylindrical body fixed to a base 367, via the nozzle 361, tube 363, and joint 366, so that the fluid channel 354 of the inside of the sheath 341 communicates with the inside of the cylindrical body of the syringe 368. The inside of the cylindrical body of the syringe 368 has a piston 369 fitting the inner circumferential face thereof slidably disposed therein, functioning as a movable lid for storing the pressurized air within in an airtight manner, with the rear end side of the piston 369 being stepped down to a narrow diameter and extended backwards, and the rear end is connected to a movable portion 371 of a linear actuator 370.

Applying driving signals to the linear actuator 370 allows the movable portion 371 to be driven forwards and backwards as indicated by the arrow, thereby supplying and discharging pressurized air to and from the fluid channel 354 side of the sheath 341.

Two stoppers 372a and 372b are attached backward and forward in order to restrict the range where the movable portion 371 moves back and forth.

Figures 67A, 67B:
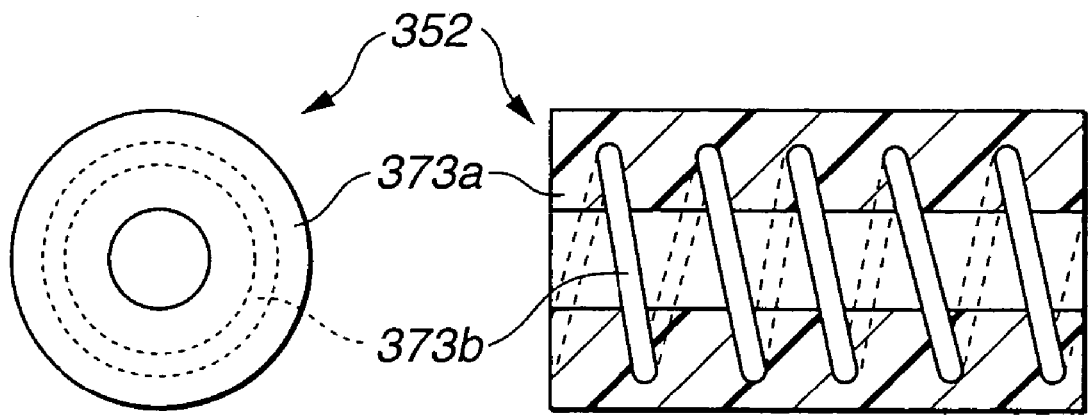
FIG. 67A and FIG. 67B are diagrams illustrating the configuration of an elastic cylinder.

FIG. 67A and FIG. 67B illustrate a specific configuration of the elastic cylinder 352 shown in FIG. 62 and FIG. 64. FIG. 67A shows a longitudinal-section view, and FIG. 67B shows a frontal view.

The elastic cylinder 352 is formed of a cylindrical elastic cylinder main unit 373a, and a coil spring 373b which has properties of expanding and contracting being embedded within the elastic cylinder main unit 373a in a ring-like shape.

In this way, the coil spring 373b is embedded within the elastic cylinder 352, so upon pressurized air being sent therein, the elastic cylinder 352 expands in the longitudinal direction due to expansion thereof in the radial direction being restricted, and accordingly the tip frame 351 at the tip side thereof moves.

FIG. 68A, FIG. 68B, FIG. 69A, and FIG. 69B each represent structures of first and second modifications of the elastic cylinder 352. The symbols A and B indicate longitudinal-section views and frontal views, respectively.

Figures 68A, 68B:
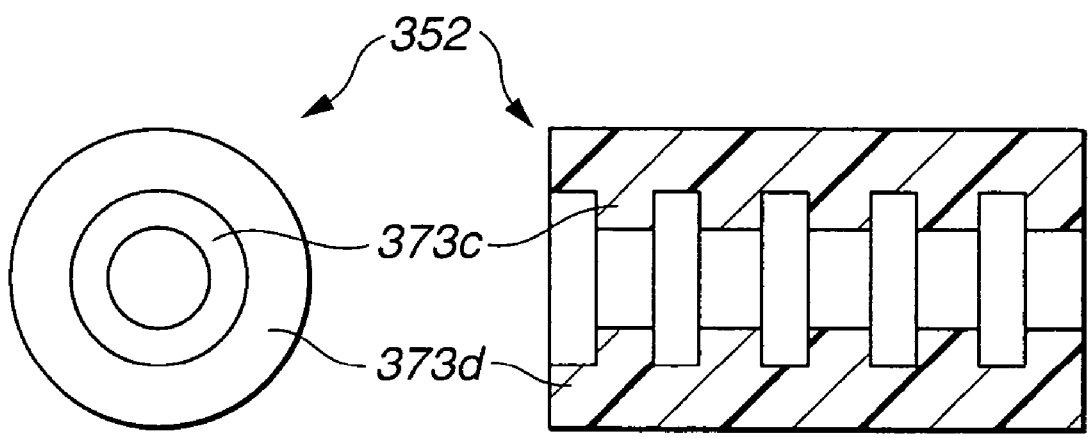
FIG. 68A and FIG. 68B are diagrams illustrating a first modification of the configuration of an elastic cylinder.

The elastic cylinder 352 shown in FIG. 68A and FIG. 68B has the inner face of the elastic cylinder 352 formed in steps, for example, with thick portions 373c and thin portions 373d being cyclically formed in the longitudinal direction.

The thin portions 373d provide properties for expanding in the longitudinal direction, and the thick portions 373c restrict expanding in the radial direction.

Figures 69A, 69B:
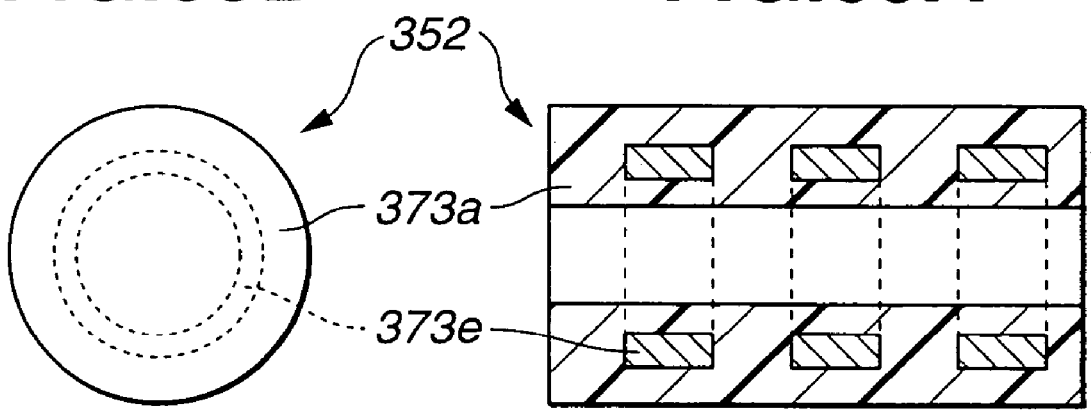
FIG. 69A and FIG. 69B are diagrams illustrating a second modification of the configuration of an elastic cylinder.

The elastic cylinder 352 shown in FIG. 69A and FIG. 69B has rings 373e embedded within the elastic cylinder main unit 373a instead of the coil spring 373b in the case in FIG. 67A and FIG. 67B at predetermined intervals in the longitudinal direction thereof, and embedding the rings 373e at predetermined intervals yields the same functions as with the case in FIG. 67A and FIG. 67B.

According to the thirteenth embodiment described above, a balloon 353 for expanding under supply of pressurized air 355 so as to be fixed on the inner wall of the channel 343 of the endoscope 342 is provided near the tip of the optical scanning probe 305, and the elastic cylinder 352 which extends under supply of pressurized air 355 is provided near the tip thereof, so the elastic cylinder 352 can be extended and the tip frame 351 disposed at the front end thereof moved in the longitudinal direction of the probe 305.

The object unit 330 or optical scanning optical system 350 for scanning the observation light 324 in a direction orthogonal to the longitudinal direction of the probe 305 is stored inside the tip frame 351, so an image two-dimensionally scanned by the object unit 330 or optical scanning optical system 350 can be obtained, while driving the elastic cylinder 352 allows the observation light 324 or the observation point 326 serving as a focal position thereof to be scanned in the longitudinal direction of the probe 305, thereby obtaining an image in the depth-wise direction of the object of observation 325.

In this case, as shown in FIG. 64 providing the elastic cylinder 352 so as to form a portion of the mantle tube of the optical scanning probe 305 allows the optical scanning optical system 350 at the tip side thereof to be moved in the longitudinal direction of the probe 305 such that depth-wise direction scanning can be performed, so depth-wise direction scanning can be performed without increasing the outer diameter of the probe 305.

The structure according to the present embodiment wherein a fluid is sealed in the sheath 341 forming the mantle tube of the optical scanning probe 305, the moving means (extending/compacting movable means) in an elastic cylinder shape capable of extending and compacting provided at the tip side of the sheath 341 is moved by changing the pressure of fluid from the operating side or supplying and discharging the fluid, and the hard tip portion provided on the tip side thereof, specifically the optical scanning optical system 350 for performing two-dimensional optical scanning that has been provided within the tip frame 351, is moved in the longitudinal direction thereof so as to change the focal position, thus enabling providing to the tip side of the optical scanning probe 305 without increasing the outer diameter of the optical scanning probe 305.

In other words, forming a portion of the tip side of the sheath 341 making up the mantle tube of the optical scanning probe 305 with a elastic cylinder 352 which is simply formed to expand and compact allows the focal position of the optical scanning optical system 350 to change (move) in the depth-wise direction of the subject or the object of observation 325, and accordingly, optical tomographic images can be obtained at each position in the depth-wise direction of the subject, in a simple manner without increasing the outer diameter of the probe.

For example, setting the speed for changing the focal position so as to be slower than the frame rate for two-dimensionally scanning the optical scanning optical system 350 enables optical tomographic images to be consecutively obtained at different positions in the depth-wise direction of the subject.

Also, two-dimensional tomographic images can also be obtained by scanning the optical scanning optical system 350 capable of two-dimensional scanning in one direction alone, i.e., one-dimensionally, and oscillating the pressure change (or supply and discharge) of the fluid.

Also, the scanning range in the depth-wise direction can be easily enlarged. That is to say, increasing the value of pressure application increases the range of moving in the depth-wise direction.

Accordingly, the present embodiment has the following advantages.

Optical image information as to the depth-wise direction of the subject can be obtained with a simple structure and by changing pressure of the fluid, without increasing the outer diameter of the probe of the optical scanning probe 305.

Also, the scanning range can be easily enlarged.

Figure 70:
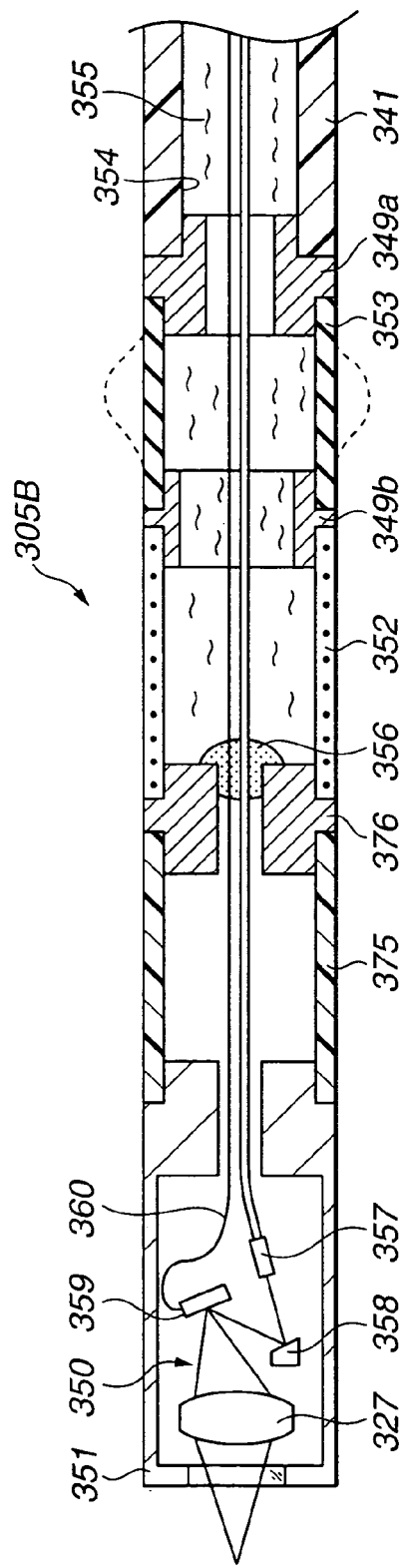
FIG. 70 is a diagram illustrating the configuration at the tip side of the optical scanning probe in a modification.

FIG. 70 illustrates the tip side configuration of an optical scanning probe 305B which is a modification of the thirteenth embodiment.

This optical scanning probe 305B further comprises a flexible cylinder 375 between the tip frame 351 and the elastic cylinder 352 of the optical scanning probe 305 shown in FIG. 64. More specifically, the tip of the elastic cylinder 352 is fixed to the rear end of a hard linking ring 376 and the front end of the linking ring 376 and the base of the tip frame 351 are connected with a soft cylinder 375 having flexible properties. Other configurations are the same as with FIG. 64.

Providing a soft cylinder 375 at the base end of the hard tip frame 351 thus allows the hard portion length at the tip side to be shortened as compared to arrangements wherein this is not provided, thereby facilitating insertion and the like of the probe 305B into bent portions or a bent channel 343, reducing the work of the technician in insertion and so forth.

Fourteenth Embodiment

FIG. 71A and FIG. 71B illustrate the structure of the tip side of a optical scanning probe 305C according to a fourteenth embodiment of the present invention, with regard to a case of not being pressurized and a case of being pressurized. The present embodiment is a mechanism serving as both the moving means in the longitudinal direction according to the thirteenth embodiment and the fixing means for expanding in the radial direction for fixing.

The optical scanning probe 305C shown in FIG. 71A and FIG. 71B in an arrangement wherein, with the optical scanning probe 305 shown in FIG. 64, the tip of the sheath 341 is connected to the rear end of a cylindrical elastic member 381 which expands in the radial direction and expands and contracts in the longitudinal direction via the linking ring 349a, with the front end of the elastic member 381 fixed to the base of the tip frame 351.

The other configurations are the same as with FIG. 64, and in the present embodiment as well the tip frame 351 is moved in the longitudinal direction of the probe under supply and discharge of compressed air (pressurized air) 355, so that the observation light 324 can be scanned in the depth-wise direction of the object of observation 325.

In the state that the pressurized air 355 is not fed in, the state shown in FIG. 71A is realized, and in the state that the pressurized air 355 is fed in as shown in FIG. 71B, the elastic member 381 expands and expands in the radial direction, this expansion causing the tip frame 351 held at the front side by the elastic member 381 to be moved backwards.

In this case, the tip position of the linking ring 349a is at the same position in both FIG. 71A and FIG. 71B, and the portion in front of this moves due to the expanding deformation of the elastic member 381. As shown in FIG. 71A, the observation point 326 which is the focal point within the object of observation 325 moves along with the movement of the tip frame 351 as shown in FIG. 71B, so that the surface of the object of observation 325 becomes the object of observation 326.

Deforming the elastic member 381 thus with pressurized air 355 enables the observation point 326 to be scanned in the depth-wise direction of the object of observation 325, thereby obtaining a two-dimensional image at each depth position.

FIG. 72A and FIG. 72B illustrate a specific configuration of the elastic member 381, wherein FIG. 72A is a side view and FIG. 72B is a frontal view.

As shown in FIG. 72A and FIG. 72B, the elastic member 381 is configured of a cylindrical elastic member main unit 382a, and a mesh member 382b embedded in the elastic member main unit 382a following the circumference at the same position, for example. The mesh member 382b is formed by crisscrossing wires in a mesh form, so as to make the elastic member 381 to be suitably expandable, and also have properties of extending and contracting lengthwise in the longitudinal direction along with the expansion.

Also, FIG. 73A and FIG. 73B illustrate a specific configuration of a modification of the elastic member 381, wherein FIG. 73A is a side view and FIG. 73B is a frontal view.

The elastic member 381 shown in FIG. 73A and FIG. 73B is configured with line members 382c embedded as straight lines in the longitudinal direction in the elastic member main unit 382a following the same circumference face, instead of the mesh 382b.

According to the present embodiment, the same operations and advantages can be obtained as the thirteenth embodiment, with a simple structure.

While the longitudinal length shrinks by the elastic member 381 itself being expanded in FIG. 72A through FIG. 73B, this may be arranged with a structure having the functions for a moving portion 383 and a fixed portion 384 as shown in FIG. 74A through 76B. In this case, the moving portion 383 moves in the longitudinal direction when under pressurization (at the time of supplying the pressurized air 355), and the fixed portion 384 expands in the radial direction and can be used for fixing.

FIG. 74A and FIG. 74B illustrate the article shown in FIGS. 67A and 67B forming a moving portion 383, and further forming a fixing portion 384 by integrally connecting an expandable cylinder thereto.

Also, FIG. 75A and FIG. 75B illustrate the article shown in FIGS. 68A and 68B forming a moving portion 383, and further forming a fixing portion 384 by integrally connecting an expandable cylinder thereto.

Also, FIG. 76A and FIG. 76B illustrate the article shown in FIGS. 69A and 69B forming a moving portion 383, and further forming a fixing portion 384 by integrally connecting an expandable cylinder thereto.

Fifteenth Embodiment

FIG. 77A illustrates the structure at the tip side of an optical scanning probe 305D according to the fifteenth embodiment. Note that FIG. 77B is a cross-sectional view at the balloon portion in FIG. 77A.

The optical scanning probe 305D shown in FIG. 77A and FIG. 77B uses a multi-lumen tube 387 as a sheath. The multi-lumen tube 387 has a center lumen 385e, and besides this, multiple, specifically four lumens 385a through 385d formed around, with the lumens 385a through 385d each communicating with balloons 386a through 386d provided on the perimeter position through holes around the tip of the tube 387.

The operating side of the lumens 385a through 385d is connected to a pressure variation device 262 (see FIG. 65), so that the balloons 386j (j=a through d) can each be independently expanded by supplying pressurized air 355. The optical scanning probe 305D can be inserted through the channel 343 of the endoscope 342 shown in FIG. 61, and also, can be fixed to the inner wall of the channel 343 by expanding the balloons 386a through 386d, thereby enabling optical scanning images to be obtained.

FIG. 78A through FIG. 78D illustrate states of the respective balloons 386a through 386d being expanded within the channel 343. Note that FIG. 78A through FIG. 78D only show reference numerals for the primary components.

Also, as shown in FIG. 77A, an optical scanning optical system 350' for two-dimensional scanning is disposed on the tip frame 351 to the side of the probe 305D with the present embodiment. That is to say, with the optical scanning optical system 350', the optical axis O of the condenser lens 327 is to the side of being orthogonal to the longitudinal direction of the probe 305. Also, an optical fiber 313 and signal line 360 are inserted through the lumen 385e at the center.

Controlling the expansion of the balloon 386a and 386c as shown in FIG. 78A and FIG. 78B for example allows the observation point 326 to be moved in the depth-wise direction of the object of observation 325, thus obtaining a two-dimensional observation image at each depth.

Also, controlling the expansion of the balloons 386b and 386d as shown in FIG. 78C and FIG. 78D allows the observation point 326 to be moved in the sideways direction, thus obtaining a two-dimensional observation image at a different position.

With the present embodiment, the vicinity of the probe tip can be moved by the expansion of the balloons 386a through 386d, so that the observation point 326 can be moved in the optical axis direction of the condenser lens 327, and also the observation point 326 can be moved in the sideways direction orthogonal to the optical axis direction.

That is to say, according to the present embodiment, even in the event that the surface of the object of observation 325 is generally parallel to the longitudinal direction of the probe, an optical scanning image of the depth-wise direction can be obtained in approximately the same manner as the first embodiment, and also the observation range can be changed.

Sixteenth Embodiment

FIG. 79A illustrates the structure at the tip side of an optical scanning probe 305E according to a sixteenth embodiment of the present invention. FIG. 79B is a cross-sectional view of FIG. 79A at the portion which expands and becomes a moving member.

With the optical scanning probe 305E according to the present embodiment, balloons 386a through 386d are not provided to the circumferential face at the tip side of the multi-lumen tube 387 shown in FIG. 77A, instead, an even softer and expandable multi-lumen tube 389 is connected via a joint 388, and the base of the tip frame 351 is connected to the tip of the multi-lumen tube 389.

The multi-lumen tube 389 is expanded by pressurized air 355 and fixed on the inner wall of the channel 343 of the endoscope 342, and the tip frame 351 of the tip side is moved in the longitudinal direction of the tube 389, thereby enabling scanning of the optical scanning optical system 350 disposed on the inside of the tip frame 351 in the optical axis direction of the condenser lens 327.

The present embodiment has approximately the same advantages as the thirteenth embodiment.

Also, in the above-described embodiments, water or other fluids may be supplied and discharged instead of the pressurized air 355 to expand the balloons 353 and 386, the elastic member 381, and the tube 389 and the like, thereby moving the elastic cylinder 352 and so forth.

Seventeenth Embodiment

FIG. 80 illustrates the structure at the tip side of an optical scanning probe 305F according to a seventeenth embodiment of the present invention. The present embodiment does not use pressurized air, and instead extends and compacts the elastic cylinder 352 in the longitudinal direction by rotating a flexible shaft with a motor.

The optical scanning probe 305F according to the present embodiment is not provided with the ring-shaped balloon 353 in FIG. 70, the tip of the sheath 341 is connected to the elastic cylinder 352 by a connecting frame 391, and the tip of the rotable flexible shaft 392 inserted through the sheath 341 is rotably supported by a cam bearing 393 provided to the connecting frame 391, thereby linking to a cam 394.

An inclined face is formed to the tip face of the cam 394, such that the end portion of a rod-shaped protruding piece 395 provided on the connecting frame 376 and extending in the longitudinal direction of the probe 305F comes in contact with this inclined face.

In this case, the elastic cylinder 352 attempts to shrink due to the elastic force thereof, but is restricted by the protruding piece 395 coming into contact with the cam 394. Upon the cam 394 rotating, the elastic cylinder 352 becomes a length according to the rotating position thereof.

Note that the close side of the flexible shaft 392 is connected to an unshown motor, so that the rotational angle of the motor can be changed by a switch. With the present embodiment, instead of using pressurized air, adjustment of the rotational angle of the flexible shaft 392 by the motor or constant rotation thereof allows the observation point 326 from the optical scanning optical system 350 to be moved in the depth-wise direction of the object of observation.

FIG. 81 illustrates an optical scanning probe 305G according to a first modification. This optical scanning probe 305G uses double cylinders 396a and 396b instead of the elastic cylinder 352 in FIG. 80.

That is, the connecting frame 391 is connected to the outer cylinder 396a by a thin tube 397 for ensuring watertightness, and the connecting frame 391 fits with the outer cylinder 396a and is connected with the sliding inner cylinder 396b. In this case, more linear sliding movement can be made.

The other configurations are the same as with those in FIG. 80, and the advantages thereof are approximately the same as the arrangement in FIG. 80.

FIG. 82 is a modification of the fixing means in the above-described embodiment, wherein an optical scanning probe 305H does not use the expanding ring-shaped balloon 353 in FIG. 64 but instead is connected to the elastic cylinder 352 by the connecting frame 349a at the tip of the sheath 341, and also stores an o-ring 398 in a groove provided on the perimeter of the connecting frame 349a, whereby the o-ring 398 forms the fixing means.

Figure 83:
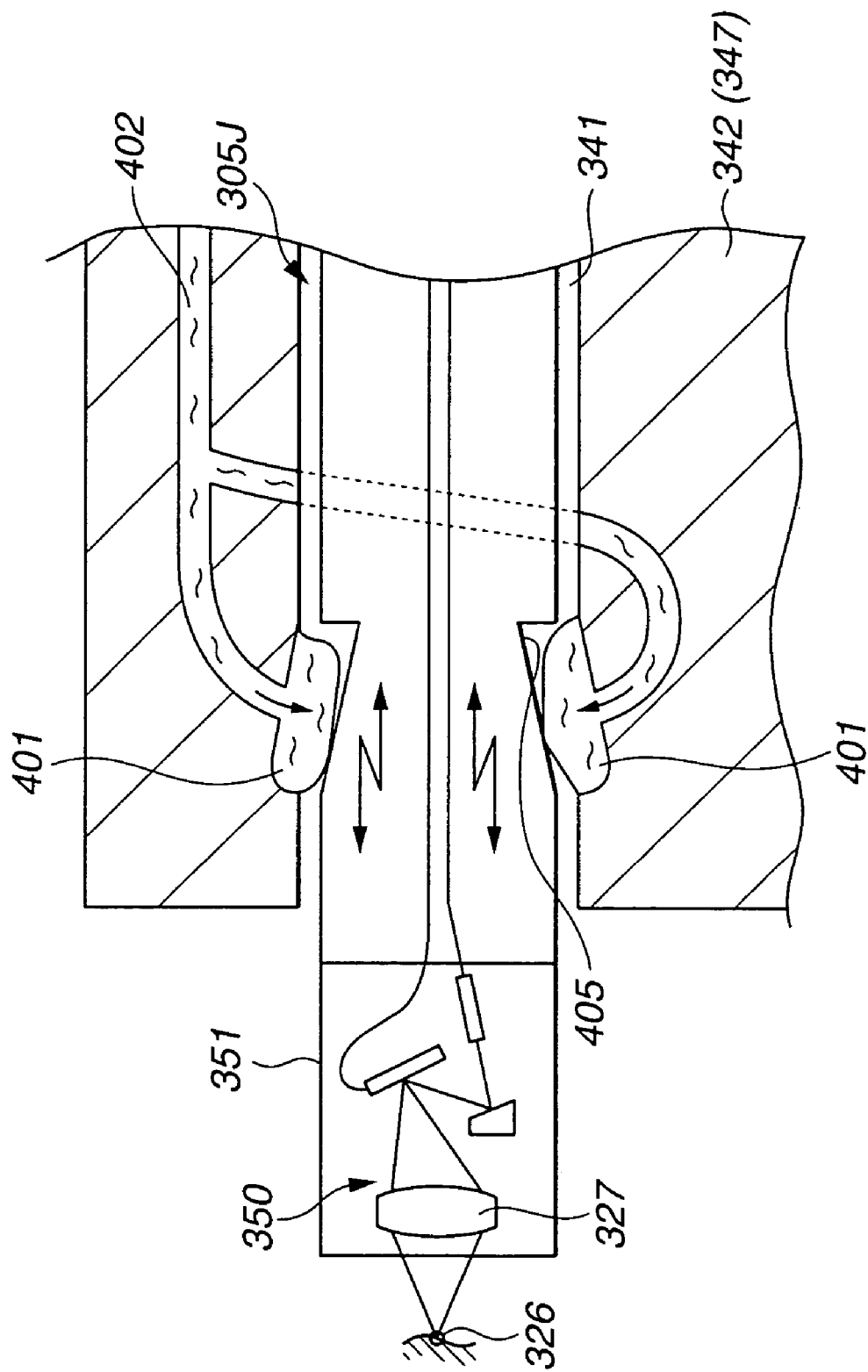
FIG. 83 is a diagram illustrating the configuration at the tip portion of the channel of an endoscope and near the tip portion of the optical scanning probe according to an eighteenth embodiment of the present invention.

In the above-described embodiments and the like, the moving means have been formed on the side of the optical scanning probe 305 and so forth, but FIG. 83 and subsequent arrangements have the moving means provided on the endoscope side.

Eighteenth Embodiment

FIG. 83 shows a channel of an endoscope according to an eighteenth embodiment of the present invention, and the configuration at the tip side of an optical scanning probe 305J inserted therethrough.

A recess enlarged in a tapered manner is formed near the tip of the channel 343 of the endoscope tip portion 347, with a balloon 401 positioned in the recess, and also with a tapered recess 405 on the tip side of the sheath 341 at the optical scanning probe 305J side as well, such that in the event that the balloon 401 expands, the tip frame 351 of the optical scanning probe 305J is pressed and moved forwards by pressing the tapered recess 405, thereby enabling the observation point 326 from the condenser lens 327 to be moved in the depth-wise direction.

With the optical scanning probe 305J according to the present embodiment, the observation point 326 from the condenser lens 327 can be moved in the depth-wise direction with a simple structure, thereby providing a slender optical scanning probe 305J which can be realized at low costs.

Also, a tapered recess 405 is provided on the optical scanning probe 305J side and a tapered recess is also provided on with the channel 343 side, but an arrangement may be made wherein, instead of these, a recess is formed in the longitudinal direction so as to store an o-ring 403 formed long in the longitudinal direction so that in the event that balloons 401 are expanded, the o-ring 403 is shrunk in the longitudinal direction, thereby moving the tip frame 351 of the optical scanning probe 305J forwards.

Nineteenth Embodiment

Figure 84:
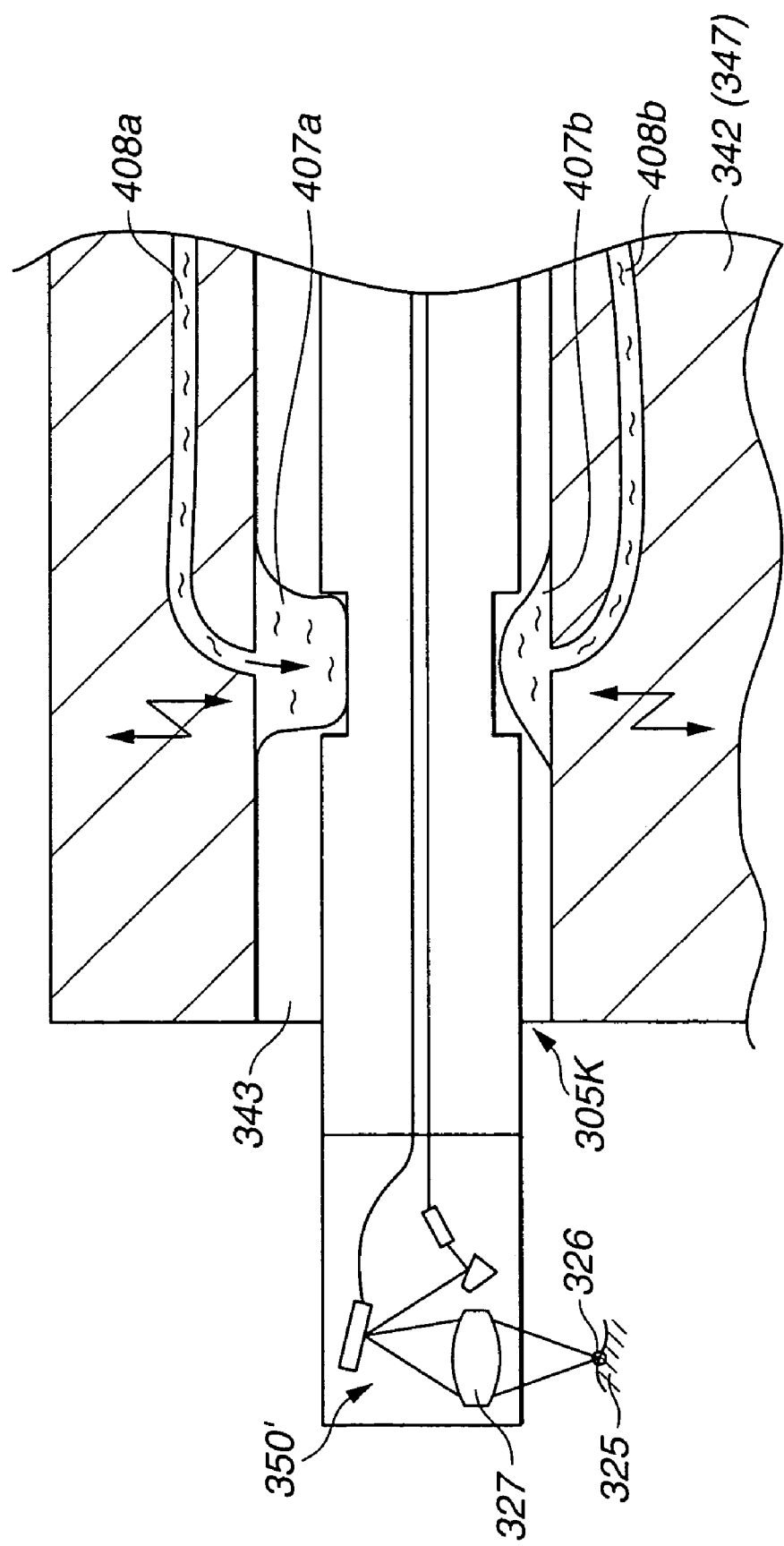
FIG. 84 is a diagram illustrating the configuration at the tip portion of the channel of an endoscope and near the tip portion of the optical scanning probe according to an nineteenth embodiment of the present invention.

FIG. 84 shows a channel of an endoscope according to a nineteenth embodiment of the present invention, and the configuration at the tip side of an optical scanning probe 305K inserted therethrough.

With the present embodiment, around the tip of the channel 343, balloons 407a and 407b are disposed at multiple positions in the circumferential direction of the inner cavity forming the channel 343, at least two positions, each communicating with fluid channels 408a and 408b.

The near side of the fluid channels 408a and 408b are connected to the pressure variation device 362, and operating a switch 356 independently supplies and discharges pressurized air, so as to independently expand the balloons 407a and 407b, pressing and moving the recesses provided on the optical scanning probe 305K by the expansion.

That is to say, adjusting the amount of expansion for expanding the balloons 407a and 407b forms moving means for pressing the sheath 341 part of the optical scanning probe 305K and moving in a direction orthogonal to the longitudinal direction. With this optical scanning probe 305K, the optical scanning optical system 350' shown in FIG. 77 is disposed within the tip frame 351.

Accordingly, with the present embodiment, the moving means move orthogonal to the longitudinal direction of the optical scanning probe 305K, but the optical scanning optical system 350' for emitting light to the side of the tip frame 351 inside of the optical scanning probe 305K is disposed, so the observation point 326 can be scanned in the depth-wise direction of the object of observation 325.

With the present embodiment as well, the optical scanning probe 305K can be realized with a simple structure and at low costs, and an observation image can be obtained by scanning in the depth direction.

FIG. 85A through FIG. 85D are diagrams summarizing the relation between the converging means and the moving direction by the moving means, according to the thirteenth through nineteenth embodiments.

Figure 85C:
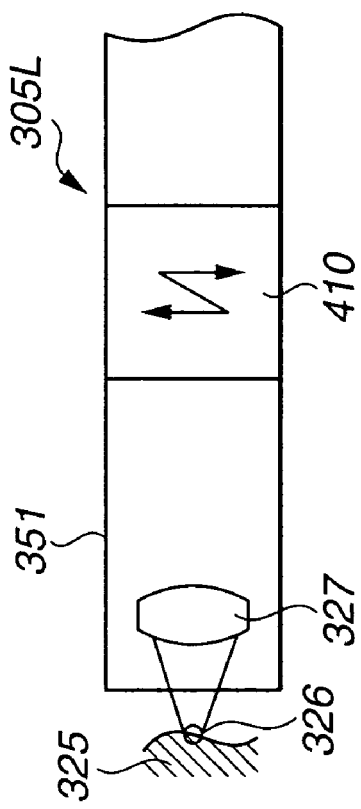
FIG. 85A through FIG. 85D are explanatory diagrams summarizing the relation between the moving direction of the moving means and the converging means in the thirteenth through nineteenth embodiments of the present invention.
Figure 85D:
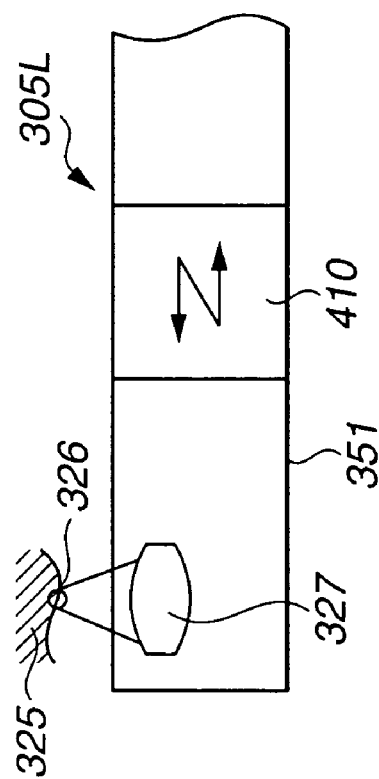
Figure 85A:
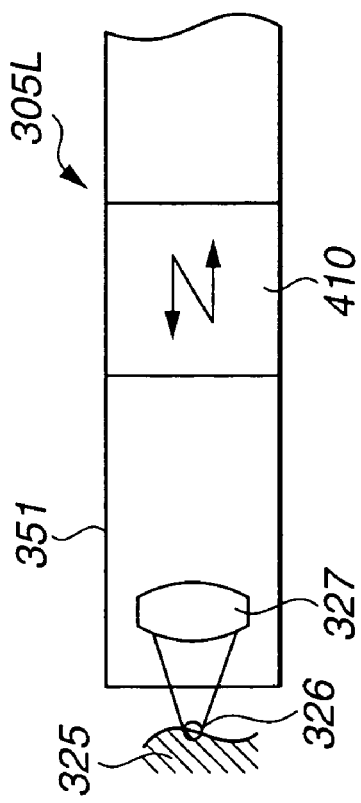
Figure 85B:
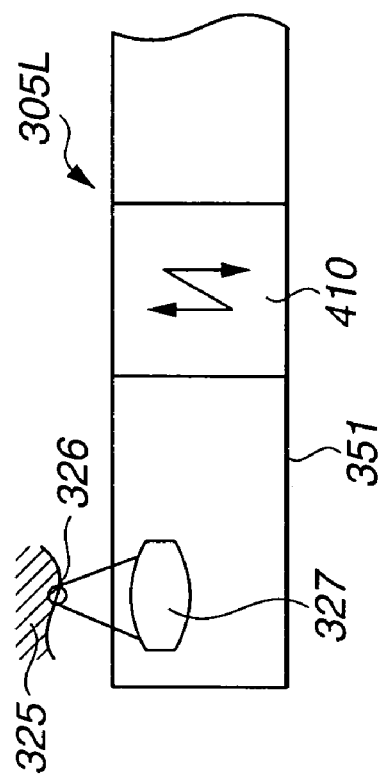

With FIG. 85A and FIG. 85B, moving means on the probe side or the endoscope side move the portion to be moved, indicated by reference numeral 410, on the optical scanning probe 305L, in the direction indicated by the arrow, and this movement enables changing the observation point 326 of the condenser lens 327 in the depth-wise direction of the object of observation 325.

On the other hand, with FIG. 85C and FIG. 85D, moving means on the probe side or the endoscope side move the portion to be moved, indicated by reference numeral 410, on the optical scanning probe 305L, in the direction indicated by the arrow, and this movement enables changing the direction of the observation point 326 of the condenser lens 327 along the surface or orthogonal to the optical axis of the object of observation 325, thereby enlarging the scanning range.

Twentieth Embodiment

Figure 86:
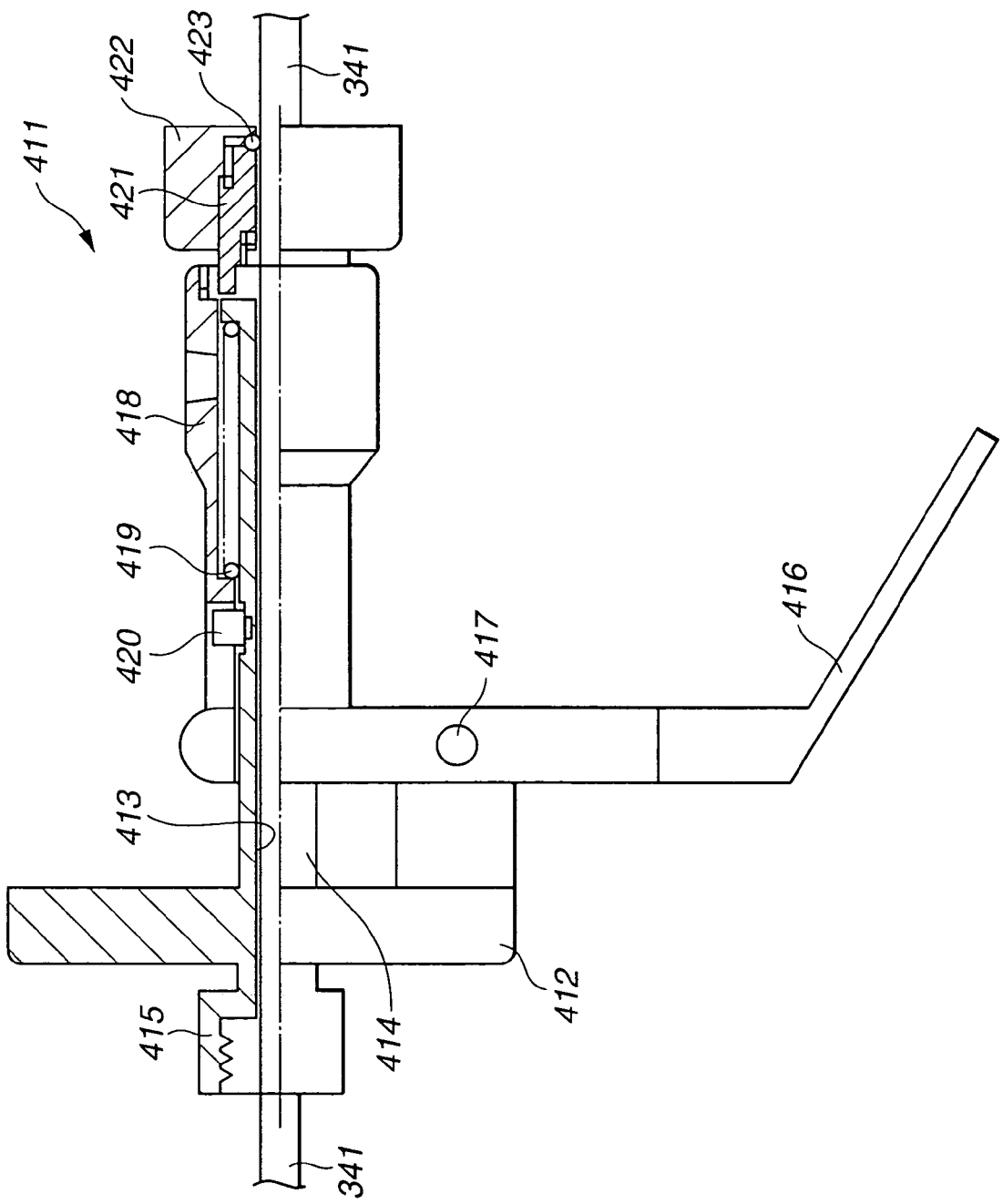
FIG. 86 is a diagram illustrating the configuration of a moving amount reducing mechanism for moving with reduced moving operational amount, according to a twentieth embodiment of the present invention.

FIG. 86 illustrates a movement amount reducing mechanism 411 according to a twentieth embodiment. With this movement amount reducing mechanism 411, a guide member 414 provided with an insertion hole 413 permitting insertion of the sheath 341 (of the optical scanning probe 305) is extended horizontally on the main unit 412, with an attachment portion 415 provided on the tip thereof, and a forceps opening 346 (see FIG. 61) of the endoscope 342 detachably mounted to the attachment portion 415.

Also, an operating lever 416 which the user grips and operates is rotably connected to the main unit 412 so as to rotate on a fulcrum 417. Also, a slide member 418 movable in the horizontal direction as to the guide member 414 is connected on the upper end of the operating lever 417, so that the slide member 418 moves in the horizontal direction by rotational operating of the operating lever 417.

Also, a spring 419 is disposed in the space between the guide member 414 and the slide member 418, pressing in the opposite direction moved by the operating lever 418 with the spring 419.

Note that a pin 420 is erected on the slide member 418 side from the guide member 414 at the portion adjacent to the spring 419, so that there is no rotation.

Also, an inner ring 421 with a hollow structure for fixing the probe is connected to the rear end of the slide member 418, and an outer ring 422 is further connected to the inner side ring 421 by screwing, with an o-ring 423 inserted in a groove provided on the inner circumference thereof.

Tightening the outer ring 422 as to the inner ring 421 presses and deforms the o-ring 423, so as to be pressed against the sheath 341 inserted through the inner side thereof, and using the friction thereof to fix the sheath 341 as to the slide member 418.

With this movement amount reducing mechanism 411, the operating portion of the operating lever 416 which the user grips and rotates is at a position distanced downwards from the fulcrum 417, and on the other hand, the distance from the fulcrum 417 to the connecting portion as to the slide member 418 near the upper end of the operating lever 416 is shorter than the above-described distance.

Accordingly, rotating the operating portion on the lower end of the operating lever 416 moves the slide member 418 forwards according to a rotational amount wherein the rotational amount thereof has been reduced, and the sheath 641 fixed by the o-ring 423 also moves forward with the movement.

Due to such a configuration, the optical scanning probe 305 can be linearly advanced or retreated with the amount of operations made by the user reduced.

Figure 87:
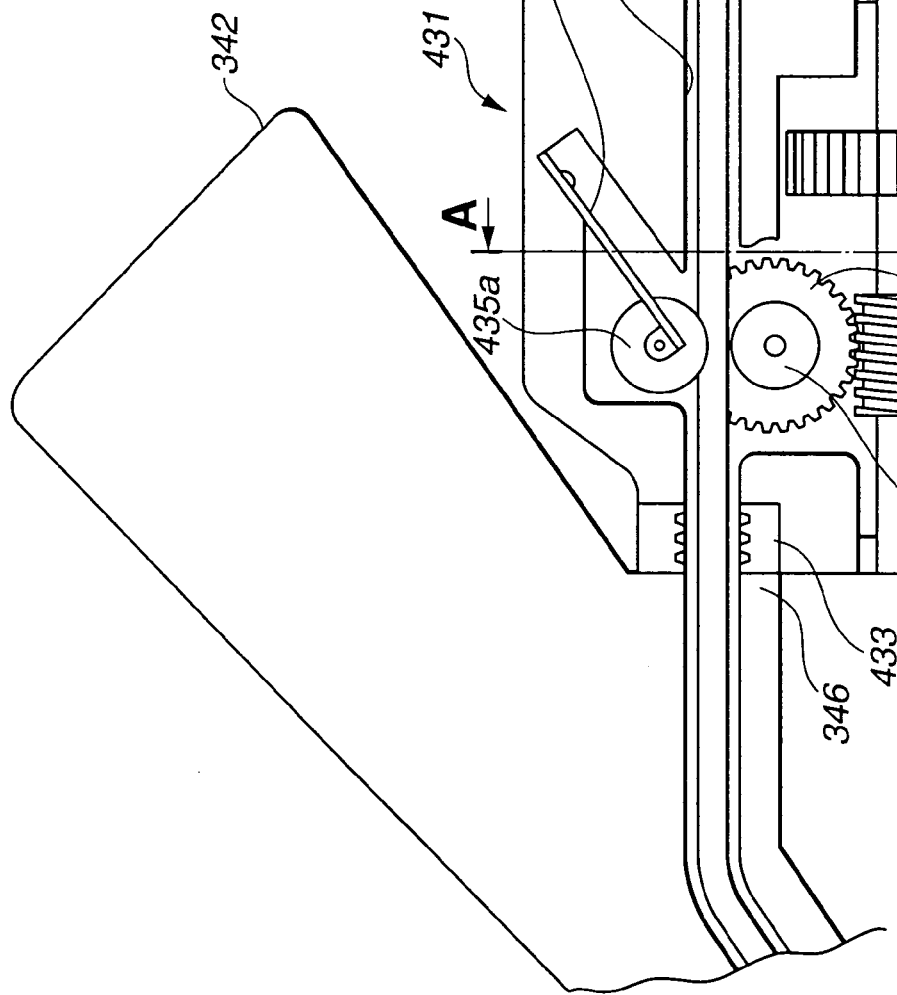
FIG. 87A is a diagram illustrating the configuration of the moving amount reducing mechanism according to a modification.
FIG. 87B is a cross-sectional diagram along A—A in FIG. 87A.

FIG. 87A illustrates an movement amount reducing mechanism 431 using a worm gear, which is a modification of the twentieth embodiment, and FIG. 87B is a cross-section along A—A thereof. The movement amount reducing mechanism 431 has an attachment portion 433 provided on the tip of a main unit 432 attached to a forceps opening 346 of the endoscope 342, with an insertion hole 434 provided behind this, and the sheath 341 of the optical scanning probe 305, for example, is inserted through this insertion hole 434.

A pair of rollers 435a and 435b are disposed partway along the insertion hole 434, with the roller 435a pressed to the insertion hole 434 side by a leaf spring 436, so as to nip and hold the sheath 341 against the other roller 435b. Also, a gear 437 is attached to the rotating shaft of the other roller 435b, as shown in FIG. 87B as well, with the gear 437 meshing with a worm gear 438, and the worm gear 438 provided on the shaft of a dial 439.

The user rotates the dial 439 so as to rotate the roller 435b, which enables advancement and retreat of the sheath 341. In this case, the worm gear is introduced therein, so the amount of rotating operations of the user can be reduced to change the amount of rotations by the roller 435b.

That is to say, operations and advantages almost the same as those in FIG. 86 can be obtained.

Figure 88:
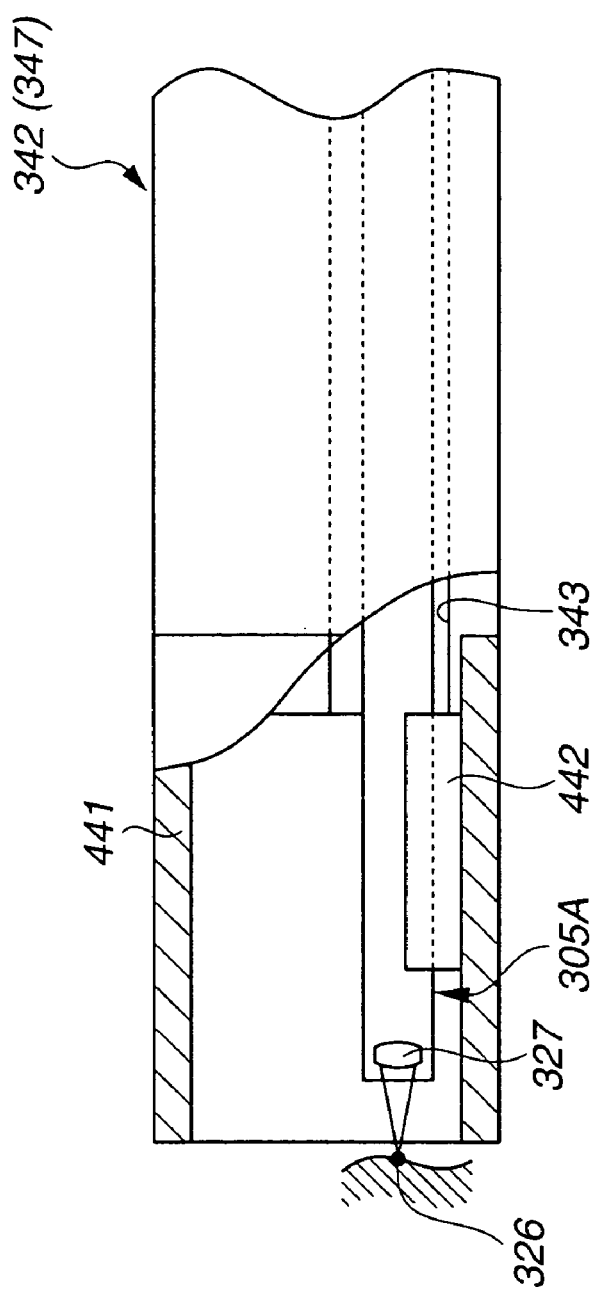
FIG. 88A and FIG. 88B are diagrams illustrating the structure of a transparent cap attached to the tip portion of an endoscope.

Also, the structure of the tip side of the endoscope 342 is shown in FIG. 88A. FIG. 88B illustrates a frontal view thereof.

A circular ring transparent cap 441 is attached to the tip portion 347 of the endoscope 342, and a guide member 442 for linearly guiding the optical scanning probe 305 for example, protruding from the exit of the forceps channel 343, in the protruding direction thereof, is attached at a position facing the exit of the forceps channel 343 within the transparent cap 441.

Such a structure facilities smooth guiding of the tip side of the optical scanning probe 305 for linear advancing and retracting.

Twenty-first Embodiment

Figure 89:
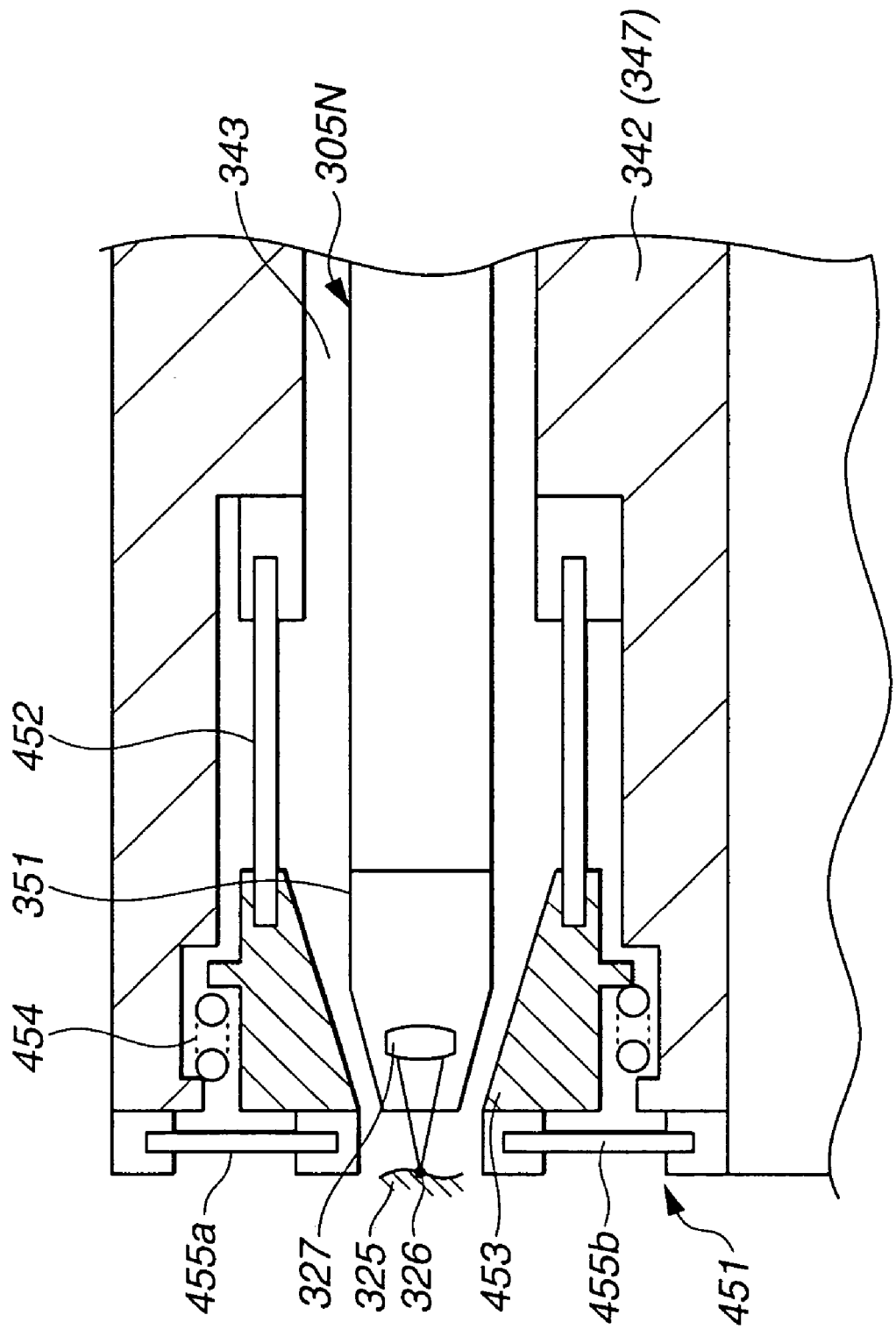
FIG. 89 is a diagram illustrating the configuration of a tapered chuck mechanism according to a twenty-first embodiment of the present invention.

FIG. 89 illustrates a tapered chuck mechanism 451 according to a twenty-first embodiment. The tip portion of the channel 343 at the endoscope tip portion 347 has an inner cavity portion forming the channel 343 widened to form a recess, and a tube 452 capable of stretching is disposed around the channel 343 in the longitudinal direction with the tip of the tube 452 holding a chuck member 453 tapered on the inner circumference so as to stretch in the longitudinal direction, with the chuck member 453 pressed backwards in the longitudinal direction by the coil spring 454.

Also, the chuck member 453 is disposed generally parallel to the tip face of the tip member 347, and connected to the end portion of the outer circumference of the tip face by stretchable elastic pieces 455a and 455b, respectively.

Also, an optical scanning probe 305N has the tip outer circumference of the tip frame 351 at the tip thereof notched out in a tapered form, so as to be capable of being in generally close contact with the tapered chuck member 453. Due to such a configuration, in the event that the optical scanning probe 305N is advanced or retreated, this is held in generally close contact by the tapered chuck member 453, so the positioning state can be set so as to be held in a stable manner.

Twenty-second Embodiment

Figure 90:
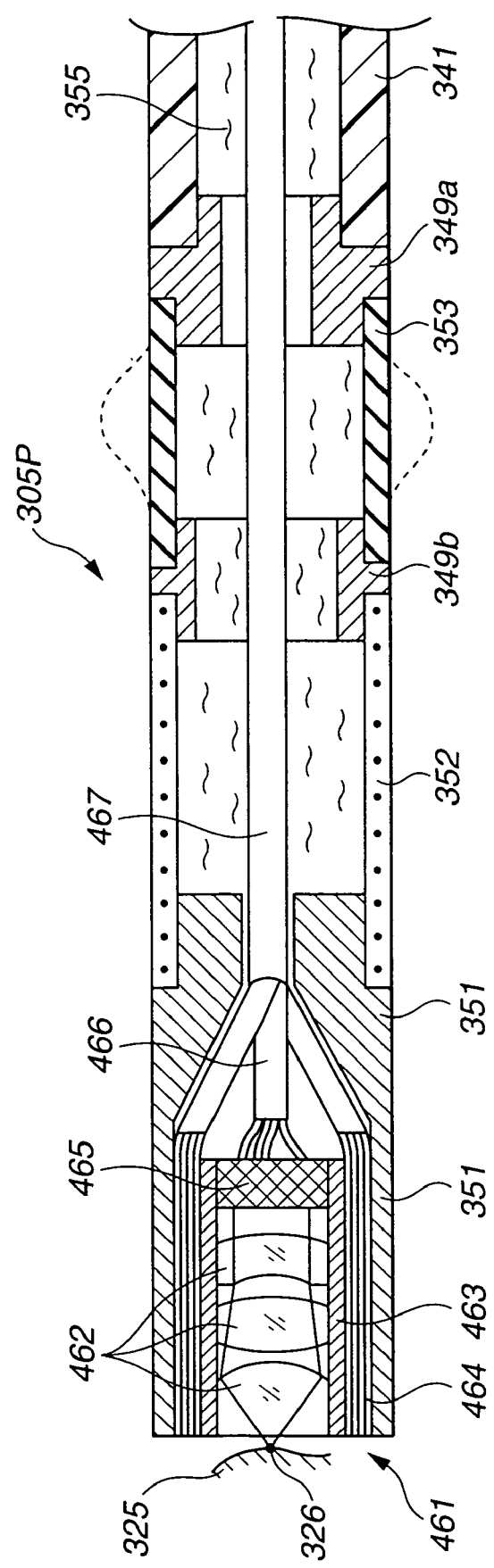
FIG. 90 is a cross-sectional diagram illustrating the configuration of the tip side of the optical scanning probe according to a twenty-second embodiment of the present invention.

FIG. 90 illustrates an optical probe 305P according to a twenty-second embodiment of the present invention. This optical probe 305P has a high-magnification observation optical system 461 described below instead of the optical scanning optical system 350 within the tip frame 351 shown in FIG. 64, for example.

With the present embodiment, the object of observation 325 side which is to be observed is dyed with a coloring agent generally used with endoscope observation such as methylene blue for example, and then washed, and observed by bringing in contact with the tip of the optical probe 305P capable of being inserted through the forceps channel of an endoscope, and so forth. In this case, cellular and glandular structures can be observed at magnification of 500 to 1000 times.

As shown in FIG. 90, provided on the inner side of the tip frame 351 is a lens frame 463 to which is attached a high-magnification object lens 462 with a large numerical aperture and a short focal distance, and a light guide 464 disposed around the lens frame 463. Also, a CCD 465 is disposed at the imaging position of the object lens 462, whereby high-magnification observation means are formed.

The CCD 465 is connected with a CCD cable 466, and the CCD cable 466 is stored within a tube 467 shared with the light guide 464 near the base of the tip frame 351.

The rear end of the light guide 464 is connected to an unshown light source device, to transmit illumination light supplied from the light source device and emit the light from the tip face thereof, thus illuminating the opposing object of observation 325 side.

Also, the rear end of the CCD cable 466 is connected to a video processor (or camera control unit) with an unshown driving circuit and picture signal processing circuit, and the images are taken of the illuminated object of observation 325, via the object lens 462.

In this case, the numerical aperture of the object lens 462 is great and forms an image at a high magnification, so images focused only around the observation point 326 at the focal position of the object lens 462 can be taken.

Other configurations are the same as those described with FIG. 64. Accordingly to the present embodiment, even in the event that two-dimensional scanning means are not provided in particular, dyeing the object of observation 325 side and using high-magnification observation means allows a high-magnification observation image to be obtained in the same manner as with the depth-wise direction scanning of the optical scanning probe 305 having optical scanning means for performing two-dimensional scanning according to the thirteenth embodiment and others.

Note that embodiments and the like formed by partially combining the above-described embodiments also belong to the present invention.

INDUSTRIAL APPLICABILITY

According to the optical scanning observation apparatus described above, an optical scanning observation apparatus can be provided wherein optical capabilities are set to a suitable state to obtain optical scanning observation images, and the tip portion can be reduced in length or outer diameter to expand usage.

The invention claimed is:

1. A scanning observation apparatus comprising:
a low-coherence light source;
light separating means for separating light emitted from the low-coherence light source into an observation light and a reference light;
an observation light optical path for transmitting the observation light;
a reference light optical path for transmitting the reference light;
optical path length variation means provided on at least one of either the observation light optical path or the reference light optical path;
converging means provided at a proximal end of the light separating means;
a light-receiving optical system for photo-reception of light, emitted from the converging means and irradiated on an object of measurement, which has been reflected or scattered;
an observation light return optical path for transmitting light received by the light-receiving optical system;
light joining means for joining the observation light return optical path and the reference light optical path;
light detecting means for converting light from the light joining means into electric signals;
image-forming means for generating an image of the object to be observed from the signals detected by the light detecting means;
display means for displaying an image;
optical scanning means for scanning light on the object to be measured;
light transmission state changing means provided on the reference light optical path, for changing the transmission efficiency of the reference light of the reference light optical path;
a reference member capable of changing a distance from a position where irradiation of light is received from the converging means;
focal position detecting means for determining a position relating to the reference member and the converging means, based on signals detected by the light detecting means, in a state wherein the light transmission state changing means is operated and the transmission efficiency of the reference light optical path is reduced; and
optical path length adjusting means for operating the optical path length variation means based on signals detected by the light detecting means, in a state wherein the light transmission state changing means is operated and interference occurs at the light joining means, such that the optical length of the optical path from the light separating means and passing through the observation light optical path, the converging means, the reference member position determined by the focal position detecting means, the light-receiving optical system, the observation light return optical path, and the light joining means, and that of the reference light optical path, substantially accord.

2. A scanning observation apparatus according to claim 1, wherein signals detected with the light detecting means used by the focal position detecting means are light intensity or contrast information.

3. A scanning observation apparatus according to claim 1, wherein signals detected with the light detecting means used by the optical path length adjusting means are light intensity or detection information.

4. The scanning observation apparatus according to claim 1, further comprising distance changing means for adjusting the position of the reference member in relation to the converging means at a position where the value of the intensity information or the contrast information of light detected with the light detecting means is maximal.

5. The scanning observation apparatus according to claim 4, wherein the optical path length adjusting means are means for adjusting the optical path length variation means such that the value of the intensity information or the contrast information of light detected with the light detecting means is maximal.

6. The scanning observation apparatus according to claim 4, wherein the distance changing means is means for substantially placing in accord a surface position of the reference member and a focal position of the converging means.

7. The scanning observation apparatus according to claim 4, wherein the distance changing means is means for substantially placing in accord a surface position of the reference member for a focal position of the converging means within a depth of field of the converging means.

8. The scanning observation apparatus according to claim 1, wherein, with the optical length of the optical path from the light separating means and passing through the observation light optical path, the converging means, the position relating to the reference member determined by the focal position detecting means, the light-receiving optical system, the observation light return optical path, and the light joining means, as optical path A in a state wherein the light transmission state changing means are operated and interference occurs at the light joining means, the optical path length adjusting means operate the optical path length variation means based on signals detected at the light detecting means, and the difference between the optical path A and the optical length of the reference light optical path is compacted into a range narrower than the longer of a depth of field of the converging means and a coherence length of the low-coherence light source.

9. A scanning observation apparatus according to claim 1, wherein the light transmission state changing means are movable shielding or light reducing means.

10. A scanning observation apparatus according to claim 1, wherein the light transmission state changing means are means for shifting an optical axis of the reference light optical path.

11. A scanning observation apparatus according to claim 1, further comprising a probe portion configured such that the observation light optical path, the converging means, the light-receiving optical system, and at least part of the observation light return optical path, are detachable from the light separating means.

12. A scanning observation apparatus according to claim 1, further comprising a probe wherein at least a part of at least one of the observation light optical path, the converging means, the light-receiving optical system, and the observation light return optical path, is configured of a flexible light transmitting means.

13. A scanning observation apparatus according to claim 11, wherein the probe portion is provided within an endoscope.

14. A scanning observation apparatus according to claim 11, wherein the probe portion is insertable through an endoscope.

15. A scanning observation apparatus according to claim 1, wherein the converging means and the light-receiving optical system are the same.

16. A scanning observation apparatus according to claim 1, wherein the converging means and the light-receiving optical system are the same, and generally form a confocal optical system.

17. The scanning observation apparatus according to claim 1, wherein the reference member is provided on an adjusting jig detachably provided on at least one of either the converging means or the light-receiving optical system.

18. The scanning observation apparatus according to claim 17, wherein the adjusting jig has a distance changing means for changing the distance between the converging means, and the light-receiving optical system and a reflection scattering member.

19. The scanning observation apparatus according to claim 18, wherein the distance changing means is provided with an actuator and is operated with the focal position detecting means.

20. The scanning observation apparatus according to claim 11, wherein the reference member is integrally configured with the probe portion, and comprises a depth scanning means for changing a distance between the reference member and the converging means.

21. The scanning observation apparatus according to claim 20, wherein the depth scanning means is provided with an actuator and is operated with the focal position detecting means.

22. A scanning observation apparatus according to claim 1, wherein the light detecting means have at least two or more outputs.

23. A method for setting a scanning observation apparatus comprising:
providing a low-coherence light source;
providing a light separating means for separating light emitted from the low-coherence light source into an observation light and a reference light;
providing an observation light optical path for transmitting the observation light;
providing a reference light optical path for transmitting the reference light;
providing an optical path length variation means provided on at least one of either the observation light optical path or the reference light optical path;
providing a converging means provided at a proximal end of the light separating means;
providing a light-receiving optical system for photo-reception of light, emitted from the converging means and irradiated on an object of measurement, which has been reflected or scattered;
providing a light joining means for joining an observation light return optical path for transmitting light received by the light-receiving optical system, the observation light return optical path, and the reference light optical path;

providing a light detecting means for converting light from the light joining means into electric signals;

providing an image-forming means for generating an image of the object to be observed from the signals detected by the light detecting means;

providing a display means for displaying an image; and providing an optical scanning means for scanning light on the object to be measured;

a first step for reducing the transmission efficiency of the reference light optical path;

a second step for making reference to the output of the light detecting means with regard to the reference member, and positioning the reference member near the focal position of the converging means;

a third step for restoring the transmission efficiency of the reference light optical path; and a fourth step wherein, with an optical length of the optical path from the light separating means and passing through the observation light optical path, the converging means, the reference member position determined by the focus position detecting means, the light-receiving optical system, the observation light return optical path, and the light joining means, as an optical path A in a state wherein positioning of the reference member is determined in the second step, the electric signals detected by the light detecting means are referred to, the optical path variation means are operated, and the optical length of the optical path A and the reference light optical path are substantially in accord.

\* \* \* \* \*

UNITED STATES PATENT AND TRADEMARK OFFICE
CERTIFICATE OF CORRECTION

PATENT NO. : 7,158,234 B2  Page 1 of 1
APPLICATION NO. : 10/808857
DATED : January 2, 2007
INVENTOR(S) : Akio Uchiyama et al.

It is certified that error appears in the above-identified patent and that said Letters Patent is hereby corrected as shown below:

<u>On Title Page:</u> Priority information is missing should read

Item (30) Foreign Application Priority Data

October 31, 2001 (JP)................................2001-335035
       May 13, 2002 (JP)................................2002-137677
       October 07, 2002 (JP)................................2002-293959

Signed and Sealed this

Twenty-ninth Day of May, 2007

JON W. DUDAS
*Director of the United States Patent and Trademark Office*